(12) United States Patent
Hartsel et al.

(10) Patent No.: US 8,026,349 B2
(45) Date of Patent: Sep. 27, 2011

(54) POLYNUCLEOTIDE SYNTHESIS LABELING CHEMISTRY

(75) Inventors: Stephanie A. Hartsel, Berthoud, CO (US); Robert J. Kaiser, Broomfield, CO (US); Michael O. Delaney, Firestone, CO (US)

(73) Assignee: Dharmacon, Inc., Lafayette, CO (US)

( * ) Notice: Subject to any disclaimer, the term of this patent is extended or adjusted under 35 U.S.C. 154(b) by 1226 days.

(21) Appl. No.: 11/660,589

(22) PCT Filed: Aug. 18, 2005

(86) PCT No.: PCT/US2005/029374
§ 371 (c)(1),
(2), (4) Date: Feb. 16, 2007

(87) PCT Pub. No.: WO2006/033730
PCT Pub. Date: Mar. 30, 2006

(65) Prior Publication Data
US 2008/0009612 A1  Jan. 10, 2008

Related U.S. Application Data

(60) Provisional application No. 60/603,472, filed on Aug. 20, 2004.

(51) Int. Cl.
*C07H 21/00* (2006.01)
*C07H 21/04* (2006.01)
(52) U.S. Cl. ................ 536/23.1; 536/25.3; 560/190
(58) Field of Classification Search .................. None
See application file for complete search history.

(56) References Cited

U.S. PATENT DOCUMENTS

| | | | |
|---|---|---|---|
| 4,849,513 A | | 7/1989 | Smith et al. |
| 5,367,066 A | * | 11/1994 | Urdea et al. ............... 536/24.3 |
| 5,580,731 A | * | 12/1996 | Chang et al. ............... 435/6 |
| 5,889,136 A | | 3/1999 | Scaringe et al. |
| 6,008,400 A | | 12/1999 | Scaringe et al. |
| 6,313,284 B1 | * | 11/2001 | Kwiatkowski et al. ...... 536/25.3 |
| 6,403,779 B1 | | 6/2002 | Kawasaki et al. |
| 6,500,217 B1 | | 12/2002 | Starz et al. |
| 6,613,215 B2 | | 9/2003 | Molter et al. |

OTHER PUBLICATIONS

International Search Report for PCT/US05/29374.
Written Opinion for PCT/US05/29374.
Wen, K., Chow, S., Sanghvi, Y. S., and Theodorakis, E. A. (2002) "Synthesis of 2'-O-Methoxyethylguanosine Using a Novel Silicon-Based Protecting Group"J. Org. Chem. 67, 7887-7889.
Jin, S., Miduturu, C. V., McKinney, D. C., and Silverman, S. (2005) "Synthesis of Amine- and Thiol-Modified Nucleoside Phosphoramidites for Site-Specific Introduction of Biophysical Probes into RNA" J. Org. Chem. 70, 4284-4200.
Dobson, N., McDowell, D. G., French, D. J., Brown, L. J., Mellor, J. M., and Brown, T. (2003) "Synthesis of HyBeacons and dual-labeled probes containing 2'-fluorescent groups for use in genetic analysis" Chem. Commun., 1234-1235.
Legorburu, U. Reese, C. B., and Song, Q. (1999) "Conversion of Uridine into 2'-O-(2-Methoxyethyl)-uridine and 2'-O-(2-Methoxyethyl) cytidine" Tetrahedron 55, 5635-5640.
Hartsel, S. A., Kitchen, D. E., Scaringe, S. A. And Marshall, W. S. (2005) "RNA Oligonucleotide Synthesis Via 5'-Silyl-2'-Orthoester Chemistry" Methods in Molecular Biology, vol. 288 (Oligonucleotide Synthesis: Methods and Applications)(P. Herdewijn, ed.), 33-49.
Preparation of 5'-Sily1-2'-Orthoester Ribonucleosides for Use in Oligoribonucleotide Synthesis Current Protocols in Nucleic Acid Chemistry, 2004, 2.10.1-2.10.16.
International Preliminary Report on Patentability (Chapter 1 of the Patent Cooperation Treaty). Mar. 1, 2007.

* cited by examiner

*Primary Examiner* — Traviss C McIntosh, III
(74) *Attorney, Agent, or Firm* — Kalow & Springut, LLP; Scott D. Locke, Esq.

(57) ABSTRACT

Methods and compositions for making nucleoside phosphoramidites and nucleic acids, including mono-, di-, and polynucleotides, comprising a linker covalently attached to a levulinyl moiety are provided. A levulinyl-protected linking moiety affords an orthogonal approach to modifying a polynucleotide during or after solid phase synthesis with a molecule of interest, for example, a conjugate or a dye.

14 Claims, 29 Drawing Sheets

SEQUENCE LISTING

<160> NUMBER OF SEQ ID NOS: 16

<210> SEQ ID NO 1
<211> LENGTH: 23
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (13)...(13)
<223> OTHER INFORMATION: linker covalently attached to a fluorescein
      label
<220> FEATURE:
<221> NAME/KEY: misc_feature
<222> LOCATION: (23)...(23)
<223> OTHER INFORMATION: deoxythymidine; RNA molecule with one
      deoxythymidine

<400> SEQUENCE: 1
cagaucgaau gaccgcuugu cat                                           23

<210> SEQ ID NO 2
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)...(1)
<223> OTHER INFORMATION: Cy3 label
<220> FEATURE:
<221> NAME/KEY: misc_feature
<222> LOCATION: (20)...(20)
<223> OTHER INFORMATION: linker covalently attached to a fluorescein
      label -continued

```
<400> SEQUENCE: 2
ccgguauaac cucaauaaua gguuugaggg ugucuaccag gaaccguaaa auccugauua      60
ccgg                                                                  64

<210> SEQ ID NO 3
<211> LENGTH: 25
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (2)...(2)
<223> OTHER INFORMATION: linker covalently attached to a fluorescein
      label
<220> FEATURE:
<221> NAME/KEY: misc_feature
<222> LOCATION: (5)...(5)
<223> OTHER INFORMATION: linker covalently attached to a dabcyl label

<400> SEQUENCE: 3
aagcuuugga cuacgauagg cauua                                           25

<210> SEQ ID NO 4
<211> LENGTH: 25
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)...(15)
<223> OTHER INFORMATION: linker covalently attached to a fluorescein
      label
<220> FEATURE:
<221> NAME/KEY: misc_feature
<222> LOCATION: (23)...(23)
<223> OTHER INFORMATION: linker covalently attached to a Cy3 label

<400> SEQUENCE: 4
ccauuugaua cacuauuauc aaagg                                           25

<210> SEQ ID NO 5
<211> LENGTH: 24
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (24)...(24)
<223> OTHER INFORMATION: linker covalently attached to a Cy3 label

<400> SEQUENCE: 5
agaucgaaug acuacgcuug ucau                                            24

<210> SEQ ID NO 6
<211> LENGTH: 9
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (4)...(4)
<223> OTHER INFORMATION: (5 and 6)-carboxyfluorescein-aminohexyl label
      attached through a linker to 2' carbon
```

```
<220> FEATURE:
<221> NAME/KEY: misc_feature
<222> LOCATION: (9)...(9)
<223> OTHER INFORMATION: deoxythymidine; RNA molecule with one
      deoxythymidine

<400> SEQUENCE: 6 gaucaucgt                                                                   9

<210> SEQ ID NO 7
<211> LENGTH: 9
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (4)...(4)
<223> OTHER INFORMATION: (5 and 6)-carboxyfluorescein-aminohexyl label
      attached through a linker to nitrogenous base
<220> FEATURE:
<221> NAME/KEY: misc_feature
<222> LOCATION: (9)...(9)
<223> OTHER INFORMATION: deoxythymidine; RNA molecule with one
      deoxythymidine

<400> SEQUENCE: 7 gaucaucgt                                                                   9

<210> SEQ ID NO 8
<211> LENGTH: 9
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (4)...(4)
<223> OTHER INFORMATION: (5 and 6)-carboxyfluorescein-aminohexyl label
      attached through a linker to 2' carbon
<220> FEATURE:
<221> NAME/KEY: misc_feature
<222> LOCATION: (9)...(9)
<223> OTHER INFORMATION: deoxythymidine; RNA molecule with one
      deoxythymidine

<400> SEQUENCE: 8 gaucaucgt                                                                   9

<210> SEQ ID NO 9
<211> LENGTH: 24
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (14)...(14)
<223> OTHER INFORMATION: (5 and 6)-carboxyfluorescein-aminohexyl label
      attached through a linker to 2' carbon
<220> FEATURE:
<221> NAME/KEY: misc_feature
<222> LOCATION: (24)...(24)
<223> OTHER INFORMATION: deoxythymidine; RNA molecule with one
      deoxythymidine

<400> SEQUENCE: 9
cagaucgaau gacucgcuug ucat                                                 24
```

```
<210> SEQ ID NO 10
<211> LENGTH: 24
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (14)...(14)
<223> OTHER INFORMATION: (5 and 6)-carboxyfluorescein-aminohexyl label
      attached through a linker to 2' carbon
<220> FEATURE:
<221> NAME/KEY: misc_feature
<222> LOCATION: (24)...(24)
<223> OTHER INFORMATION: deoxythymidine; RNA molecule with one
      deoxythymidine

<400> SEQUENCE: 10
cagaucgaau gacucgcuug ucat                                            24

<210> SEQ ID NO 11
<211> LENGTH: 9
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (9)...(9)
<223> OTHER INFORMATION: (5 and 6)-carboxyfluorescein-aminohexyl label
      attached through a linker to 2' carbon

<400> SEQUENCE: 11 gacguaccu                                                              9

<210> SEQ ID NO 12
<211> LENGTH: 25
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)...(1)
<223> OTHER INFORMATION: Cy3 label attached through linker to
      nitrogenous base

<400> SEQUENCE: 12
gagcgcuucc ccgaugagaa cuuuu                                           25

<210> SEQ ID NO 13
<211> LENGTH: 24
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (24)...(24)
<223> OTHER INFORMATION: Cy3 label attached through linker to
      nitrogenous base

<400> SEQUENCE: 13
ggagcgcuuc cccgaugaga acuu                                            24

<210> SEQ ID NO 14
<211> LENGTH: 15
<212> TYPE: RNA
<213> ORGANISM: Artificial Sequence
<220> FEATURE:
<223> OTHER INFORMATION: Synthetic polynucleotide
```

```
<220> FEATURE:
<221> NAME/KEY: misc_feature
<222> LOCATION: (15)...(15)
<223> OTHER INFORMATION: Cy3 label attached through linker to 2' carbon

<400> SEQUENCE: 14
agcaccguaa agacg                                                    15

<210> SEQ ID NO 15
<211> LENGTH: 15
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)...(15)
<223> OTHER INFORMATION: Cy5 label attached through linker to 2' carbon

<400> SEQUENCE: 15
agcaccguaa agacg                                                    15

<210> SEQ ID NO 16
<211> LENGTH: 8
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (4)...(4)
<223> OTHER INFORMATION: 6-carboxyfluorescein-aminohexyl label attached
      through linker to 2' carbon

<400> SEQUENCE: 16 uagcagcu                                                             8
```

POLYNUCLEOTIDE SYNTHESIS LABELING CHEMISTRY

CROSS REFERENCE TO RELATED APPLICATION

This application claims the benefit of the filing date of U.S. Provisional Patent Application Ser. No. 60/603,472, filed Aug. 20, 2004, the entire disclosure of which is hereby incorporated by reference into the present disclosure.

FIELD OF THE INVENTION

The present invention relates to phosphoramidites for use in polynucleotide synthesis comprising a linker covalently attached to a levulinyl moiety, and methods of using them. The invention also relates to 5'-protected nucleoside phosphoramidites comprising a linker covalently attached to a levulinyl moiety, and methods of using them. The invention further relates to solid supports for use in polynucleotide synthesis comprising a linker covalently attached to a levulinyl moiety and simultaneously to a solid phase, and methods of using them. The invention also relates to methods and compositions for making polynucleotides comprising a linker attached to a levulinyl moiety. The invention also relates to methods of labeling and/or conjugating polynucleotides attached to a solid support.

BACKGROUND

Labeling of synthetic polynucleotides is typically accomplished by one of two methods. One method consists of using a derivatized solid support, such as controlled pore glass or polystyrene, where a terminal label is attached to the solid support through a covalent linkage. The desired polynucleotide is synthesized off a free hydroxyl group present on the support-bound label, and the labeled polymer is then cleaved from the solid support when a desired length is achieved. Another method requires synthesizing the polynucleotide with a reactive terminal or internal linker, such as an amino or thiol linker, and attaching a label following synthesis employing a reactive derivative such as an active ester, maleimide, or iodoacetamide.

While the above methods can be productively used to produce a variety of labeled polynucleotides, they suffer from several disadvantages. Some useful labels are not stable when repeatedly exposed to the conditions required for polynucleotide synthesis, thereby limiting the number of support-bound species that can be utilized for labeling. Use of reactive terminal linkers requires a multi-step conjugation chemistry employing an excess of (often very expensive) label and requires at least one purification step to isolate the labeled biopolymer from excess of reactants. This method is often very inefficient due to competing side-reactions that cause breakdown of the reactive dye, and to the poor solubility of many dye derivatives in aqueous solution. Additionally, linker-modified supports for introducing reactive functionalities onto the 3'-terminus of a polynucleotide often result in low yield and poor quality of the cleaved polynucleotide, further exacerbating the inefficiency of this approach.

Thus, there is a need in the art for methods and compositions for making phosphoramidites and supports that bear protected linking groups; wherein the protected linking group chemistry is compatible with, or orthogonal to, other protecting groups commonly employed in nucleic acid synthesis. Such phosphoramidites and supports provide one or more unique reactive sites on the polynucleotide that enable automated labeling of the polynucleotide following chain assembly.

SUMMARY

Compositions comprising nucleic acids bearing one or more linkers covalently attached to a levulinyl moiety, or a derivative of a levulinyl moiety, are described. The invention includes phosphoramidites comprising a linker moiety covalently attached to a levulinyl moiety. The invention also includes 5'-protected nucleoside phosphoramidites comprising a linker covalently attached to a levulinyl moiety, and methods of using them. The invention further includes solid supports comprising a linker moiety covalently attached to a levulinyl moiety. The invention also includes methods for making the aforesaid compositions.

Methods for labeling nucleic acid molecules using an orthogonal levulinyl protecting strategy are described. The orthogonal levulinyl protecting strategy allows for placement of one or more linker moieties, each covalently attached to a levulinyl moiety or derivative of a levulinyl moiety, at any position in a nucleic acid or at any nucleotide position in a nucleic acid polymer. Nucleic acids, including nucleosides, nucleotides, dinucleotides, oligonucleotides and nucleic acid polymers, comprising a linker moiety covalently attached to a levulinyl moiety, are described. The levulinyl moiety covalently attached to the linker moiety can be removed at any convenient point during synthesis of a nucleic acid polymer, and a suitable moiety, such as, for example, a label, can be covalently attached to the linker moiety.

In one aspect, the invention provides a phosphoramidite comprising a linker covalently attached to a levulinyl moiety.

In another aspect, the invention provides a levulinyl modified ribonucleoside phosphoramidite, comprising a ribonucleoside comprising a phosphoramidite moiety, a linker, wherein said linker is covalently attached to the ribonucleoside, and a levulinyl moiety covalently attached to the linker.

In another aspect, the invention comprises a levulinyl modified ribonucleoside phosphoramidite comprising a ribonucleoside phosphoramidite that comprises a 3' carbon attached to a phosphoramidite moiety, a linker covalently attached to the ribonucleoside phosphoramidite, and a levulinyl moiety covalently attached to the linker.

In another aspect, the invention comprises a solid support for nucleotide or polynucleotide synthesis, wherein the solid support is covalently attached to a linker, wherein the linker comprises at least one functional group, wherein the at least one functional group is protected by a levulinyl moiety.

In another aspect, the invention comprises a ribonucleoside phosphoramidite, comprising a 3' carbon attached to a phosphoramidite moiety, a 5' carbon attached to a protecting moiety, and a 2' carbon having a linker covalently attached thereto, wherein the linker is protected by a levulinyl moiety. In some aspects, the protecting moiety comprises a 5' silyl moiety. The nucleoside phosphoramidite can comprise, for example, a uracil moiety, a cytosine moiety, an adenine moiety, a guanine moiety, or a hypoxanthine moiety, or natural or unnatural modifications thereof.

In another aspect, the invention provides a levulinyl modified nucleoside phosphoramidite, comprising: a 5'-silyl protecting group; a linker moiety covalently attached to the nitrogenous base of the nucleoside phosphoramidite; and a levulinyl moiety covalently attached to the linker moiety. The nucleoside phosphoramidite can comprise, for example, a uracil moiety, a cytosine moiety, an adenine moiety, a guanine moiety, or a hypoxanthine moiety, or natural or unnatural modifications thereof. The phrase "a 5'-silyl protecting group" includes a protecting group that comprises at least one silyl moiety, wherein the protecting group protects the oxygen atom of the 5' position of the nucleoside phosphoramidite.

In another aspect, the invention provides a composition comprising:

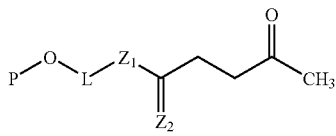

wherein L comprises a linker; $Z_1$ is an oxygen or a sulfur; $Z_2$ is an oxygen or a sulfur; and P comprises a phosphoramidite moiety.

In another aspect, the invention provides a composition comprising:

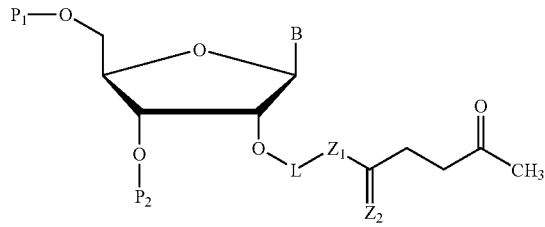

wherein B comprises a nitrogenous base that is modified or unmodified; L comprises a linker; $Z_1$ is an oxygen or a sulfur; $Z_2$ is an oxygen or a sulfur; $P_1$ comprises a blocking group; and $P_2$ comprises a phosphoramidite moiety. $P_1$ can comprise any suitable protecting moiety.

In another aspect, the invention provides a composition comprising:

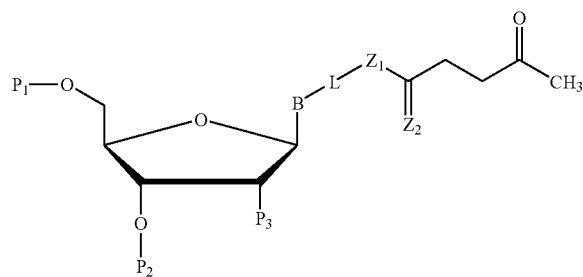

wherein B comprises a nitrogenous base that is modified or unmodified; L comprises a linker; $Z_1$ is an oxygen or a sulfur; $Z_2$ is an oxygen or a sulfur; $P_1$ comprises a blocking group; $P_2$ comprises a phosphoramidite moiety; and $P_3$ optionally comprises H, or a halogen atom, or oxygen $-Q_1$, where $Q_1$ comprises a blocking moiety, or sulfur-$Q_2$, where $Q_2$ comprises a blocking moiety, or NH-$Q_3$, where $Q_3$ comprises a blocking moiety. $P_1$ can comprise any suitable protecting moiety. $Q_1$, $Q_2$ and $Q_3$ can optionally comprise any suitable protecting group, or an alkyl group.

In another aspect, the invention provides a composition comprising:

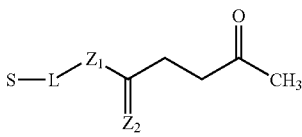

wherein L comprises a linker; $Z_1$ is an oxygen or a sulfur; $Z_2$ is an oxygen or a sulfur; and S comprises a solid support useful for the synthesis of nucleic acids.

The invention also comprises methods for making the compositions provided herein.

In another aspect, the invention provides a method for making a levulinyl modified nucleoside phosphoramidite. The method comprises: providing a nucleoside phosphoramidite comprising a protecting group on the 5'-hydroxyl and a linker moiety covalently attached to the nucleoside phosphoramidite at the 2'-hydroxyl; and covalently attaching a levulinyl moiety to the linker moiety. The 5'-protecting group can, for example, comprise a silyl moiety. The nucleoside phosphoramidite can, for example, comprise a uracil moiety, a cytosine moiety, an adenine moiety, a guanine moiety, or a hypoxanthine moiety, or natural or unnatural modifications thereof.

In another aspect, the invention provides a method for making a levulinyl modified nucleoside phosphoramidite. The method comprises: covalently attaching a linker to the nitrogenous base of a nucleoside phosphoramidite, wherein the nucleoside phosphoramidite comprises a 5'-silyl protecting group and the linker is protected by a levulinyl moiety. The nucleoside phosphoramidite can comprise, for example, a uracil moiety, a cytosine moiety, an adenine moiety, a guanine moiety, or a hypoxanthine moiety, or natural of unnatural modifications thereof.

In another aspect, the invention provides a method for making a levulinyl modified solid support for nucleotide or polynucleotide synthesis, wherein the solid support is covalently attached to a linker, and wherein the linker is protected by a levulinyl moiety. The method comprises: obtaining a compound having at least three hydroxyl groups; protecting the first hydroxyl group with a levulinyl moiety; protecting the second hydroxyl group with a protecting group suitable for removal in the first step of a polynucleotide synthesis cycle; converting the third hydroxyl group to a moiety compatible with covalent attachment to a polynucleotide synthesis support; protecting any remaining reactive groups with moieties compatible with polynucleotide synthesis; and covalently attaching the suitably protected compound to a polynucleotide synthesis support.

In another aspect, the invention provides a method for making a levulinyl modified polynucleotide bound to a solid support and having an attached linker, wherein the linker is protected by a levulinyl moiety. The method comprises: covalently attaching a protected ribonucleoside to a polynucleotide synthesis support or to a polynucleotide chain on the support; specifically removing the protecting group from the 2'-hydroxyl of the attached ribonucleoside; covalently attaching a phosphoramidite comprising a linker, wherein the linker is protected by a levulinyl moiety, to the free 2'-hydroxyl; and completing the assembly of the polynucleotide chain.

In another aspect, the invention provides a method for making a levulinyl modified polynucleotide bound to a solid support and having an attached linker, wherein the linker is protected by a levulinyl moiety. The method comprises providing a nucleoside phosphoramidite comprising a protecting group on the 5'-hydroxyl and a linker moiety covalently attached to the nucleoside phosphoramidite at the 2'-hydroxyl, wherein the linker moiety is protected by a levulinyl moiety; and covalently attaching the ribonucleoside phosphoramidite to a nucleotide or polynucleotide on the solid support.

In another aspect, the invention provides a method for making a levulinyl modified polynucleotide bound to a solid support and having an attached linker, wherein the linker is protected by a levulinyl moiety. The method comprises providing a nucleoside phosphoramidite having a linker covalently attached to the nitrogenous base, wherein the nucleoside phosphoramidite comprises a 5'-silyl protecting group and the linker is protected by a levulinyl moiety; and covalently attaching the nucleoside phosphoramidite to a nucleotide or polynucleotide on the solid support.

In another aspect, the invention provides a method for making a levulinyl modified polynucleotide bound to a solid support and having an attached linker, wherein the linker is protected by a levulinyl moiety. The method comprises assembling a polynucleotide chain on a solid support comprising a linker protected by a levulinyl moiety.

For a better understanding of the present invention together with other and further advantages and embodiments, reference is made to the following description taken in conjunction with the examples, the scope of the which is set forth in the appended claims.

BRIEF DESCRIPTION OF THE FIGURES

The preferred embodiments of the present invention have been chosen for purposes of illustration and description but are not intended to restrict the scope of the invention in any way. The benefits of the preferred embodiments of certain aspects of the invention are shown in the accompanying figures, wherein:

FIG. 17 is a schematic representation of the synthesis of a dinucleotide. $R_1$=a 5' protecting group; $R_2$ and $R_2'$=a 2'-moiety including a protected —OH (for example, —O-TBDMS, —O-TOM, or —O-ACE), —H, —O-alkyl, —F, a protected —NH$_2$ (for example, NH-trifluoroacetyl or N-phthalimidyl) and the like; $R_3$=a nucleobase protecting group including acetyl, isobutyryl, benzoyl, phenoxyacetyl, dimethylformamidine and the like; $R_4$=a phosphate protecting group such as methyl or 2-cyanoethyl; $R_2''$ and $R_2'''$=a 2'-moiety such as —OH, —H, —O-alkyl, —F, —NH$_2$ and the like.

Figure 26:
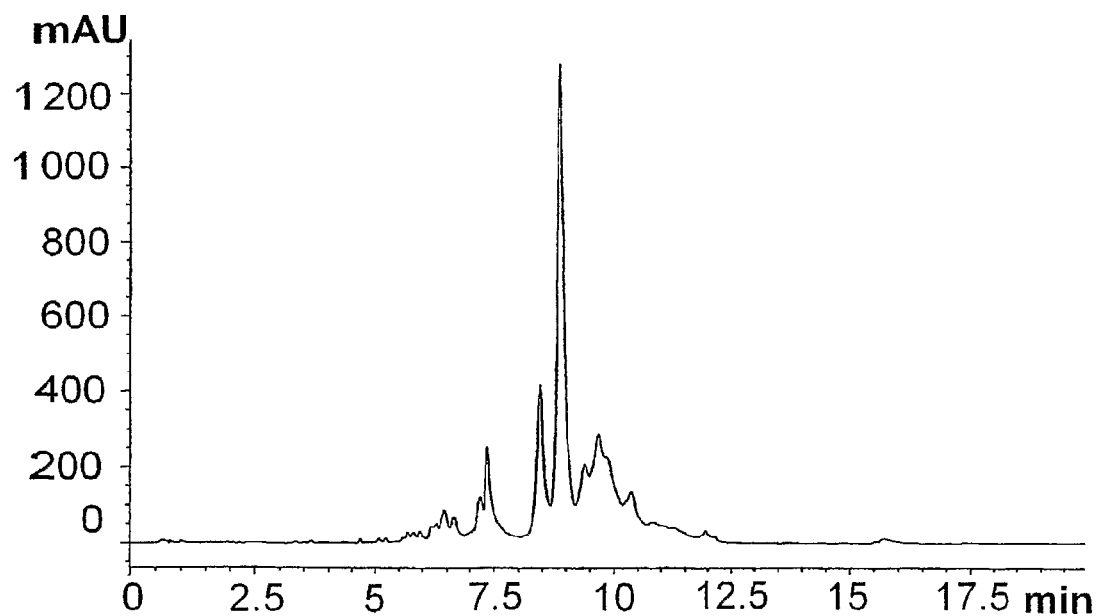

FIG. 26 is a reverse phase HPLC chromatogram of a crude labeled polynucleotide prepared using the methods of the invention. Compound 35 is used to introduce the linker to which the label is attached. The two major peaks at 8.4 and 8.9 minutes correspond to the two positional isomers of the label attached to the polynucleotide. The polynucleotide sequence is given in Table I.

Figure 27:
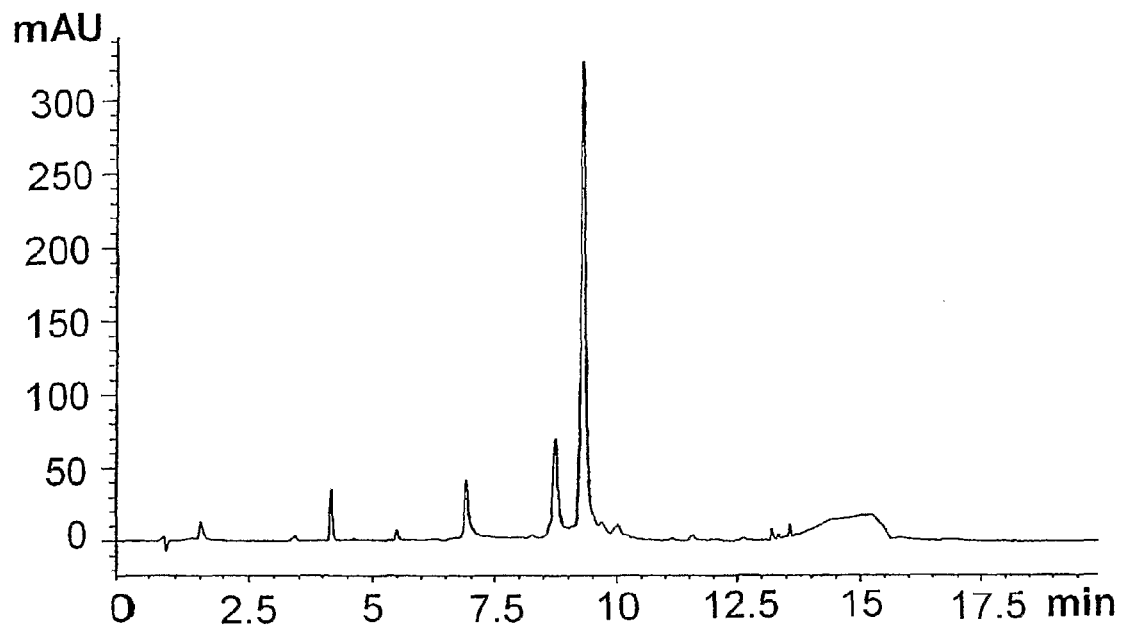

FIG. 27 is a reverse phase HPLC chromatogram of a crude labeled polynucleotide prepared using the methods of the invention. Compound 35 is used to introduce the linker to which the label is attached. The two major peaks at 8.7 and 9.3 minutes correspond to the two positional isomers of the label attached to the polynucleotide. The polynucleotide sequence is given in Table I.

Figure 28:
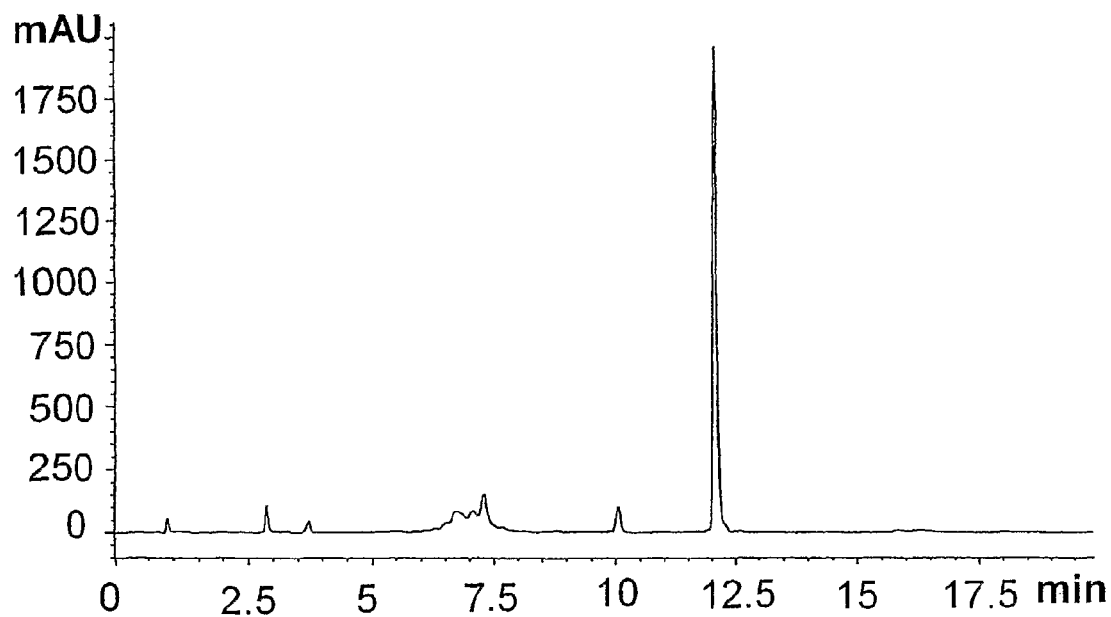

FIG. 28 is a reverse phase HPLC chromatogram of a crude labeled polynucleotide prepared using the methods of the invention. Compound 77 is used to introduce the linker to which the label is attached. The major peak at 12.0 minutes corresponds to the labeled polynucleotide. The polynucleotide sequence is given in Table I.

Figure 29:
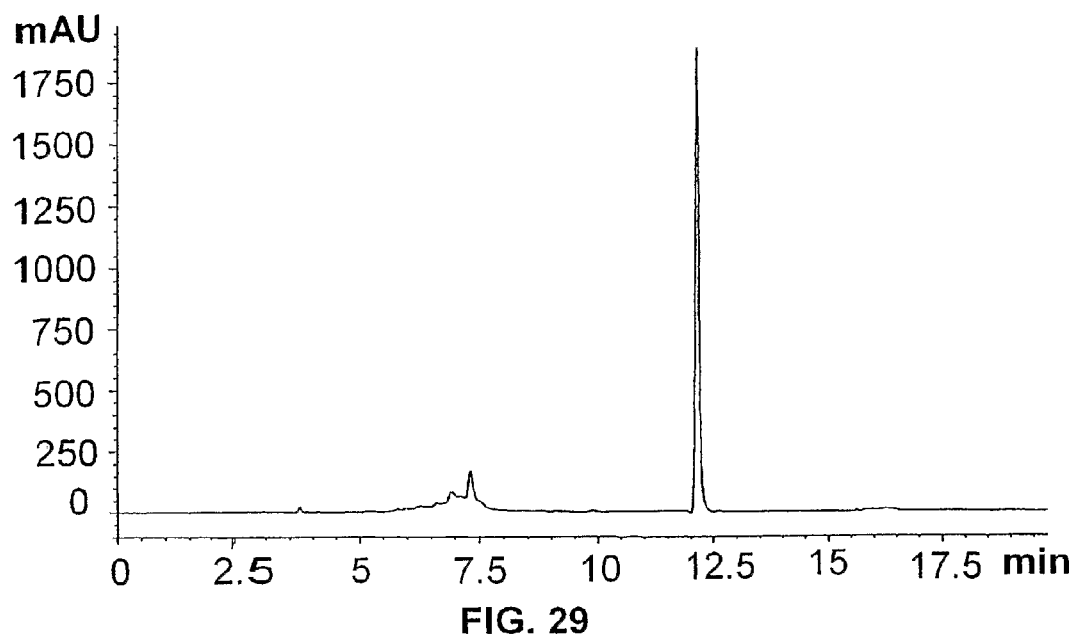

FIG. 29 is a reverse phase HPLC chromatogram of a crude labeled polynucleotide prepared using the methods of the invention. Compound 77 is used to introduce the linker to which the label is attached. The major peak at 12.1 minutes corresponds to the labeled polynucleotide. The polynucleotide sequence is given in Table I.

Figure 30:
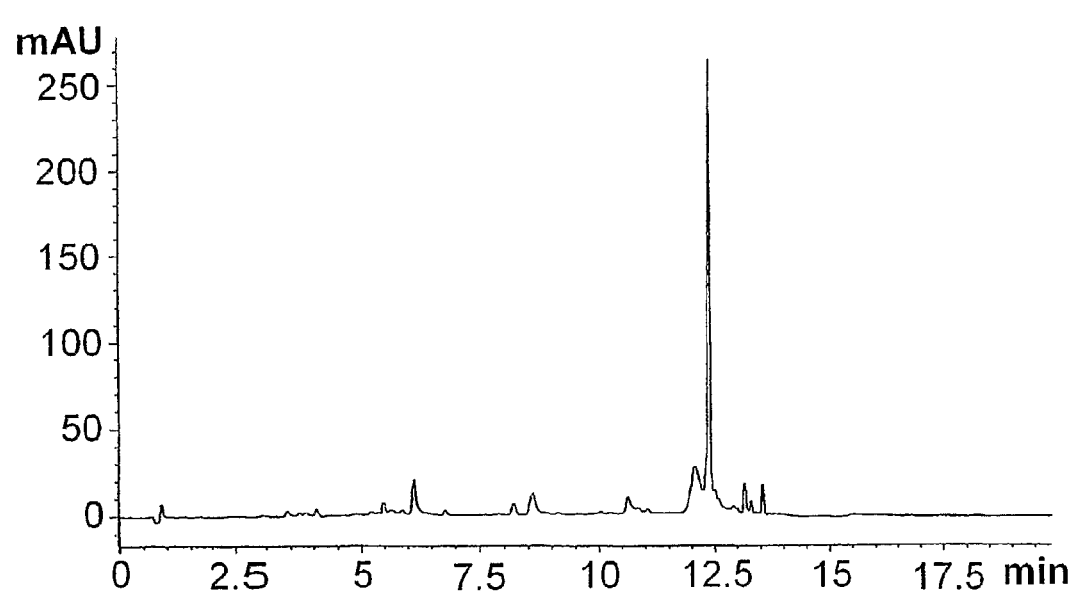

FIG. 30 is a reverse phase HPLC chromatogram of a crude labeled phosphorylated mononucleotide prepared using the methods of the invention. Compound 35 is used to introduce the linker to which the label is attached. The major peak at 12.3 minutes corresponds to the labeled mononucleotide. The mononucleotide is given in Table I.

Figure 31:
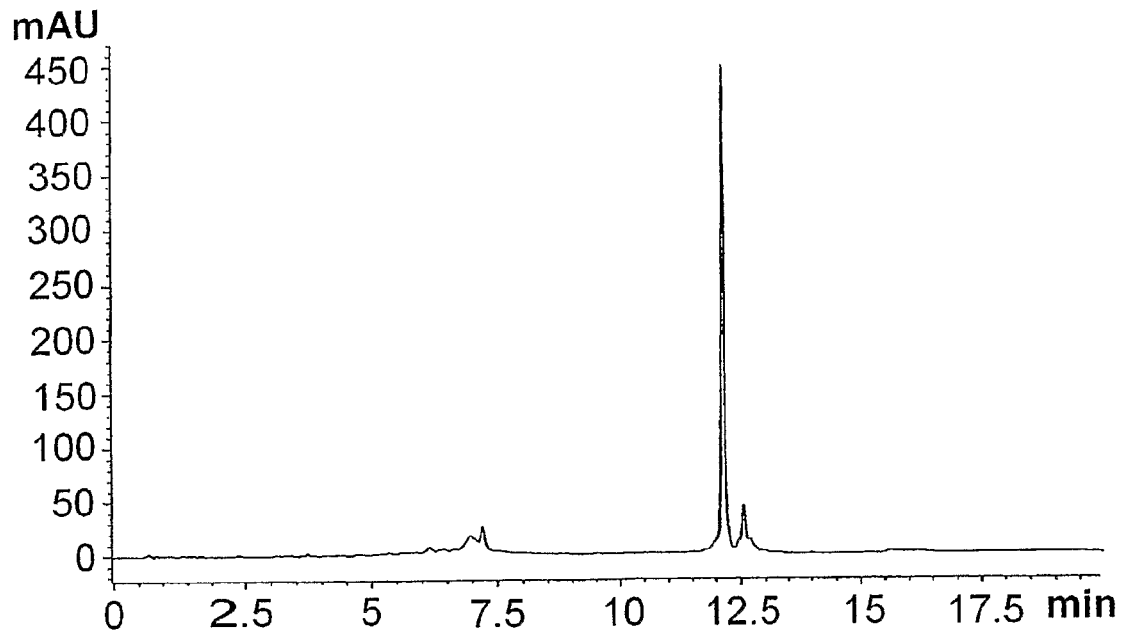

FIG. 31 is a reverse phase HPLC chromatogram of a crude labeled polynucleotide prepared using the methods of the invention. Compound 17 is used to introduce the linker to which the label is attached. The major peak at 12.2 minutes corresponds to the labeled polynucleotide. The polynucleotide sequence is given in Table I.

Figure 32:
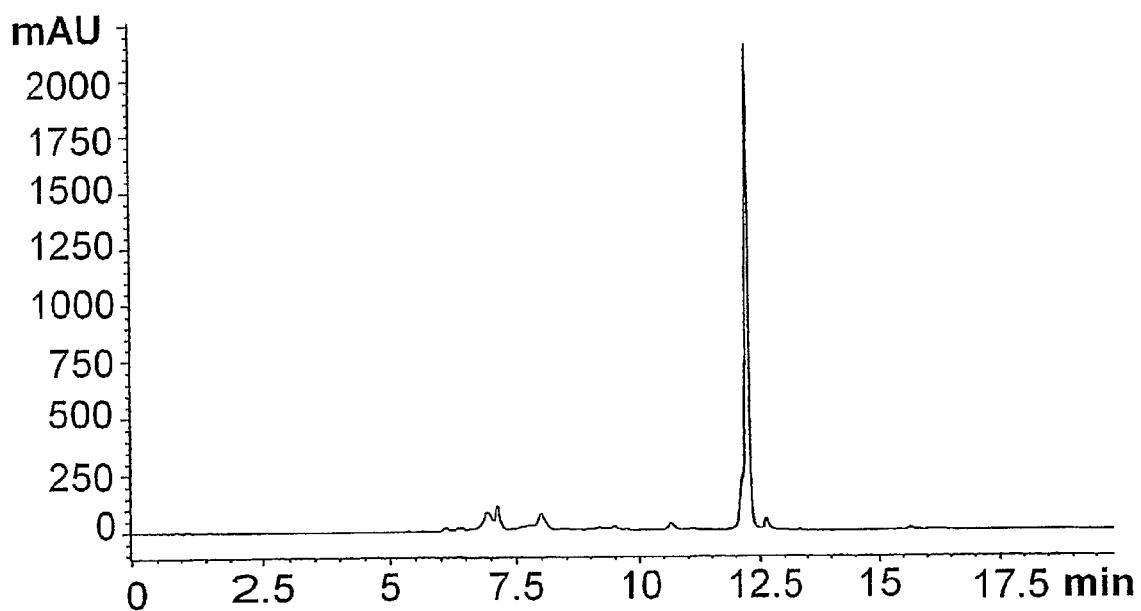

FIG. 32 is a reverse phase HPLC chromatogram of a crude labeled polynucleotide prepared using the methods of the invention. Compound 17 is used to introduce the linker to which the label is attached. The major peak at 12.2 minutes corresponds to the labeled polynucleotide. The polynucleotide sequence is given in Table I.

Figure 33:
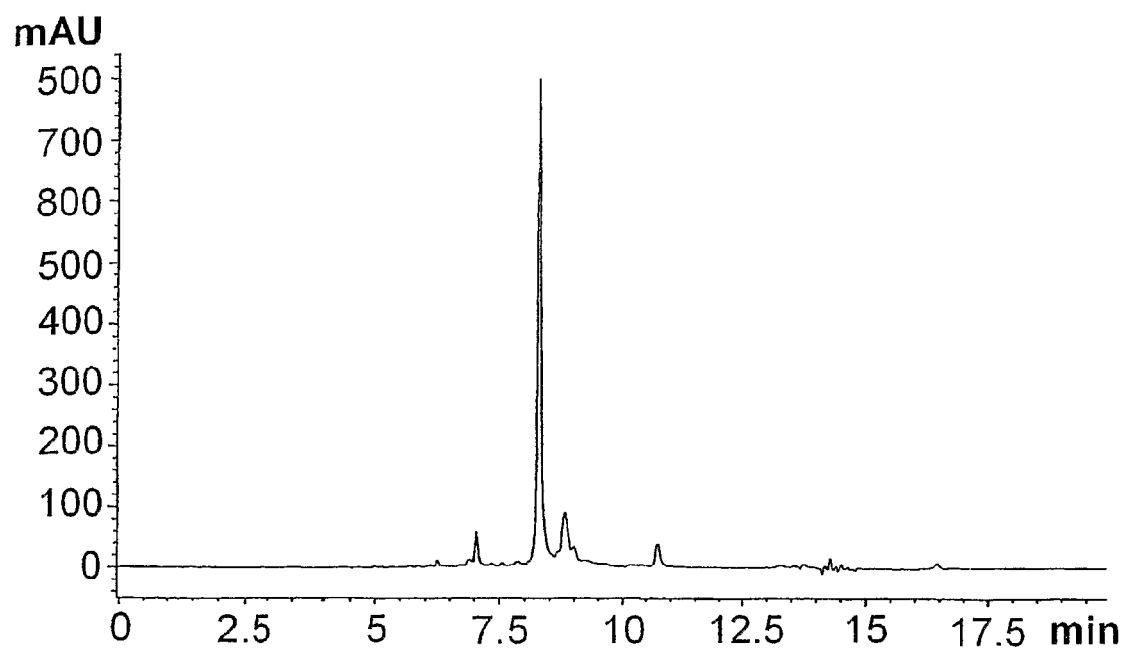

FIG. 33 is a reverse phase HPLC chromatogram of a crude labeled polynucleotide prepared using the methods of the invention. Compound 60 is used to introduce the linker to which the label is attached. The major peak at 8.3 minutes corresponds to the labeled polynucleotide. The polynucleotide sequence is given in Table I.

Figure 34:
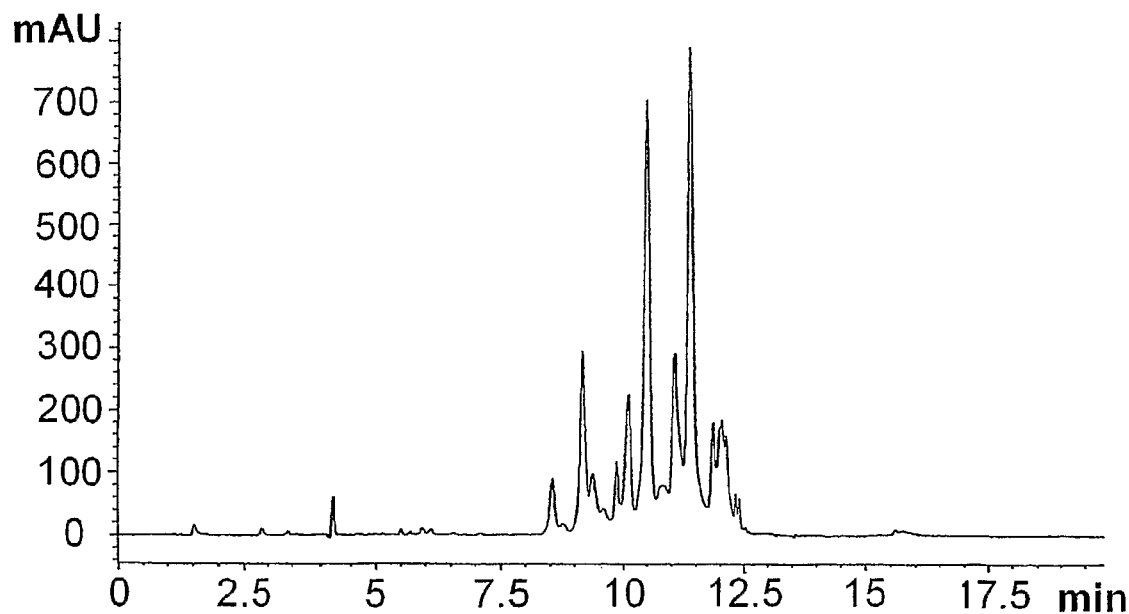

FIG. 34 is a reverse phase HPLC chromatogram of a crude polynucleotide having two different labels prepared using the methods of the invention. Compound 35 is used to introduce the linker at an internal sequence position to which one label is attached. The second label is attached to the 5'-hydroxyl. The two major peaks at 10.5 and 11.4 minutes correspond to the positional isomers of the doubly labeled polynucleotide. The polynucleotide sequence is given in the text.

Figure 35:
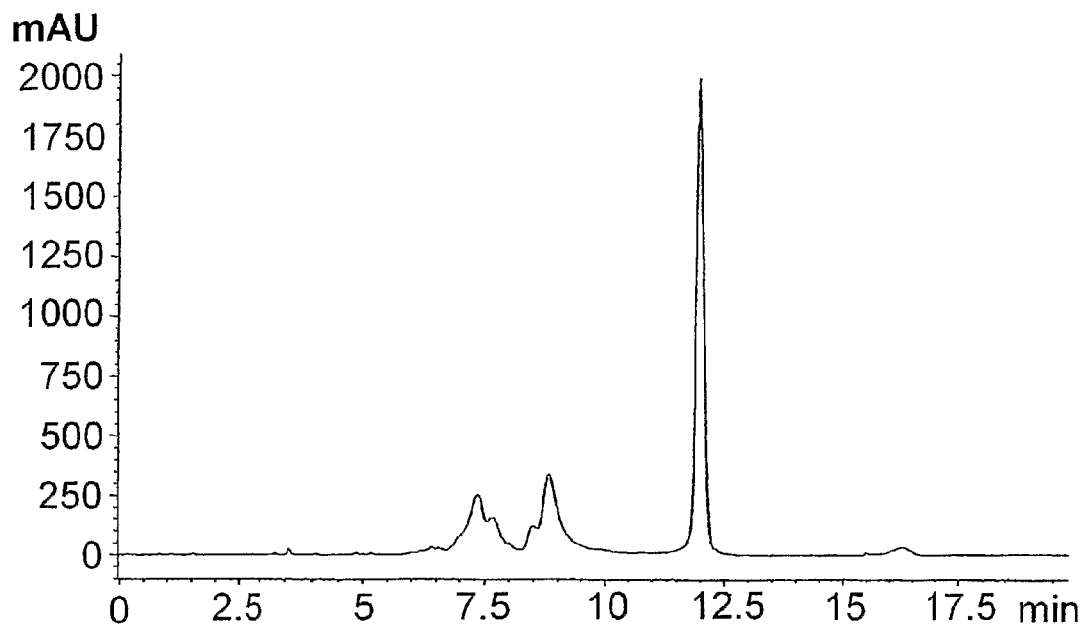

FIG. 35 is a reverse phase HPLC chromatogram of a crude polynucleotide having two different labels prepared using the methods of the invention. Compound 77 is used to introduce the linker at an internal sequence position to which one label is attached. The second label is attached to the 5'-hydroxyl. The major peak at 12.0 minutes corresponds to the doubly labeled polynucleotide. The polynucleotide sequence is given in the text.

Figure 36:
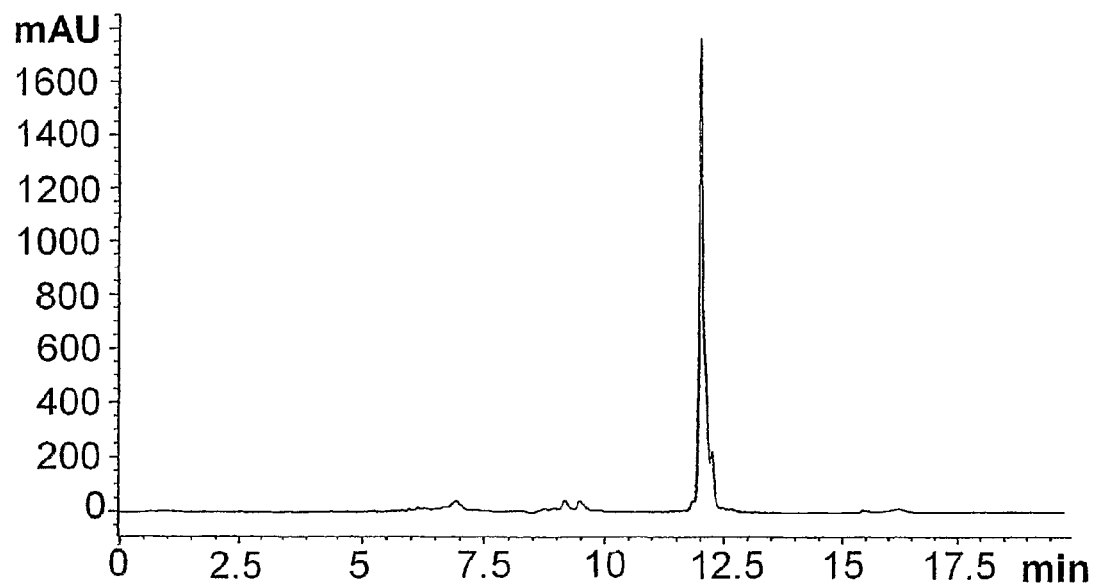

FIG. 36 is a reverse phase HPLC chromatogram of a crude polynucleotide having two different labels prepared using the methods of the invention. Compounds 77 and 35 are used to introduce linkers at two specific internal sequence positions to which the labels are attached. The major peak at 12.1 minutes corresponds to the doubly labeled polynucleotide. The polynucleotide sequence is given in the text.

Figure 37:
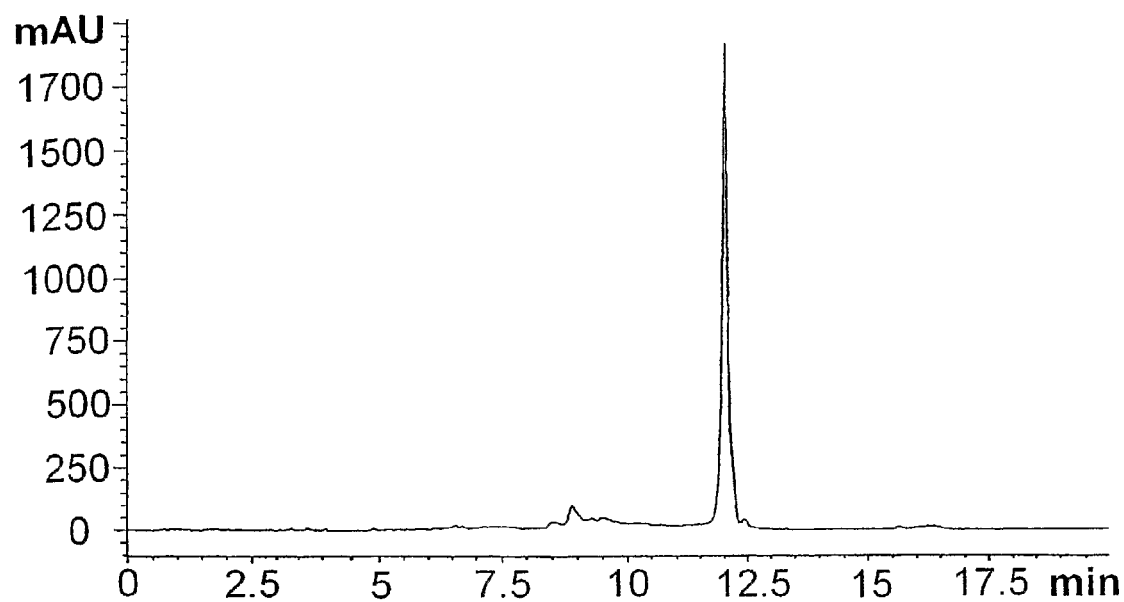

FIG. 37 is a reverse phase HPLC chromatogram of a crude polynucleotide having two different labels prepared using the methods of the invention. Compound 77 is used to introduce linkers at two specific internal sequence positions to which the labels are attached. The major peak at 12.0 minutes corresponds to the doubly labeled polynucleotide. The polynucleotide sequence is given in the text.

Figure 38:
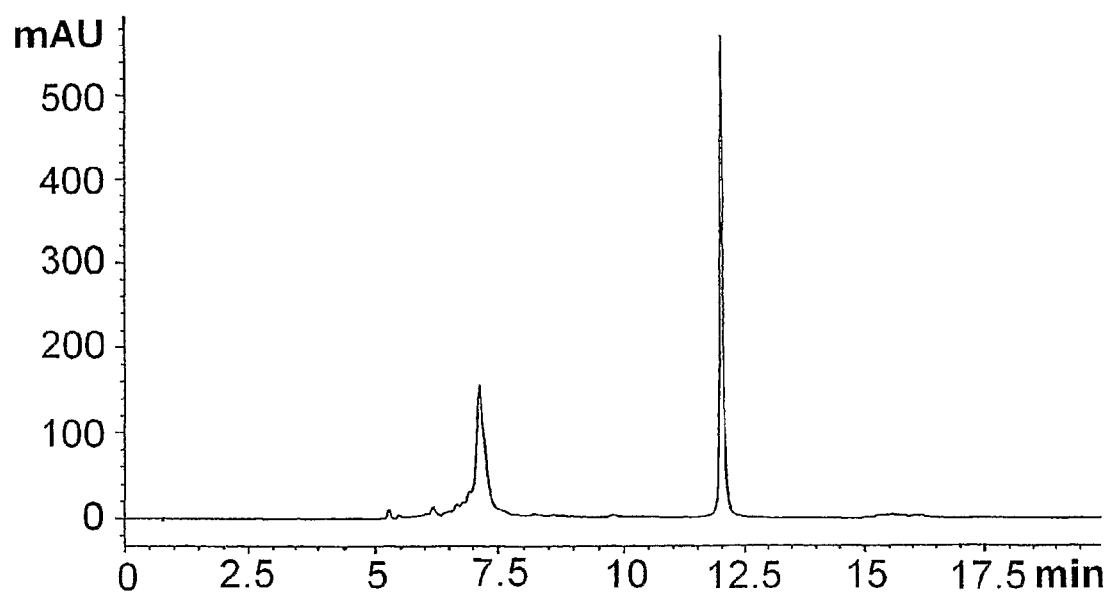

FIG. 38 is a reverse phase HPLC chromatogram of a crude labeled polynucleotide prepared using the methods of the invention. Compound 83 is used to introduce the linker to which the label is attached. The major peak at 11.5 minutes corresponds to the labeled polynucleotide. The polynucleotide sequence is given in the text.

DETAILED DESCRIPTION

The present invention will now be described in connection with the preferred embodiments. These embodiments are presented to aid in an understanding of the present invention and are not intended, and should not be construed, to limit the invention in any way. All alternatives, modifications and equivalents that may become apparent to those of ordinary skill upon reading this disclosure are included within the spirit and scope of the present invention.

This disclosure is not a primer on compositions and methods for performing polynucleotide synthesis. Basic concepts known to those skilled in the art have not been set forth in detail.

The present invention is directed to compositions, and methods for making said compositions, comprising a linking moiety protected by a levulinyl moiety or a derivative thereof. The compositions include phosphoramidites arid solid supports. The compositions further include nucleic acids and polynucleotides. In various embodiments, the nucleic acids include deoxyribonucleic acids and modified deoxyribonucleic acids, ribonucleic acids, and modified ribonucleic acids. Additionally, in various embodiments the compositions comprise DNA or RNA molecules, wherein the DNA or RNA molecules comprise at least one linker moiety covalently attached to a levulinyl moiety, or a derivative of a levulinyl moiety. DNA or RNA molecules can comprise any suitable modification known in the art. In particular, where the linker is not attached to the 2'-ribosyl position, the modified DNA or RNA molecule can comprise one or more 2'-modifications of the ribosyl moiety. Such modifications can include, for example, 2'-fluoro, 2'-O-methyl and 2'-orthoester modifications.

Unless stated otherwise, the following terms and phrases include the meanings provided below:

Alkyl

The term "alkyl" includes a hydrocarbyl moiety. A hydrocarbyl moiety is preferably saturated unless otherwise indicated, and is preferably not substituted. Thus, a hydrocarbyl moiety preferably is a hydrocarbon that is unsaturated and unsubstituted (such as, for example, a methyl, propyl, isopropyl, butyryl, isobutyryl, etc. moiety attached through a carbon bond to the moiety bearing the hydrocarbyl moiety). A hydrocarbyl moiety includes a moiety attached through a carbon bond.

Exemplary alkyl groups include but are not limited to substituted and unsubstituted groups of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl and alkyl groups of higher numbers of carbons, as well as 2-methylpropyl, 2-methyl-4-ethylbutyl, 2,4-diethylpropyl, 3-propylbutyl, 2,8-dibutyldecyl, 6,6-dimethyloctyl, 6-propyl-6-butyloctyl, 2-methylbutyl, 2-methylpentyl, 3-methylpentyl, and 2-ethylhexyl. If the exemplary alkyl group is substituted, it is described herein as a substituted alkyl group.

Substitutions within an alkyl group, if present, can include any atom or group that can be tolerated in the alkyl moiety, including but not limited to halogens, sulfur, thiols, thioethers, thioesters, amines (primary, secondary, or tertiary), amides, ethers, esters, alcohols and oxygen.

The alkyl groups can by way of example also comprise modifications such as azo groups, keto groups, aldehyde groups, carboxyl groups, nitro, nitroso or nitrile groups, heterocycles such as imidazole, hydrazine or hydroxylamino groups, isocyanate or cyanate groups, and sulfur containing groups such as sulfoxide, sulfone, sulfide, and disulfide. Alkyl groups comprising substitutions are described herein as substituted alkyl groups.

Further, alkyl groups may also comprise hetero substitutions, which are substitutions of carbon atoms by, for example, nitrogen, oxygen or sulfur. Heterocyclic substitutions refer to alkyl rings having one or more heteroatoms. Examples of heterocyclic moieties include but are not limited to morpholino, imidazolyl, and pyrrolidino. Alkyl groups comprising hetero substitutions are described herein as heteroalkyl.

Conjugate

The term "conjugate" includes a moiety that alters the physical properties of a nucleotide, polynucleotide or nucleic acid such as, for example, those that increase stability, facilitate uptake, enable detection or provide a handle for immunobilization. Conjugates include terminal conjugates and internal conjugates. A "terminal conjugate" may be attached directly or through a linker to the 3' and/or 5' unit of a polynucleotide or double stranded polynucleotide. The conjugate can be attached, for example, through a linker to the 3' position of the sugar ring at the 3' terminal unit of a polynucleotide, or to the 5' position of the sugar ring at the 5' terminal unit of a polynucleotide. An "internal conjugate" may be attached directly or indirectly through a linker to a nucleoside, for example, to the 2' position of the ribose sugar, or to other positions, including attachment to a nitrogenous base of a nucleotide unit. One example of a nucleoside comprising a conjugate is biotinylaminohexyl-3-acrylamido-uridine.

Conjugates may, for example, be amino acids, peptides, polypeptides, proteins, antibodies, antigens, toxins, hormones, lipids, nucleotides, nucleosides, sugars, carbohydrates, polymers such as polyethylene glycol and polypropylene glycol, as well as analogs or derivatives of all of these classes of substances. Additional examples of conjugates also include sterols, moieties comprising a steroid nucleus, steroids, such as cholesterol, phospholipids, di- and tri-acylglycerols, fatty acids, hydrocarbons that may or may not contain unsaturation or substitutions, enzyme substrates, biotin, digoxigenin, and polysaccharides. Still other examples include thioethers such as hexyl-S-tritylthiol, thiocholesterol, acyl chains such as dodecanediol or undecyl groups, phospholipids such as di-hexadecyl-rac-glycerol, triethylammonium 1,2-di-O-hexadecyl-rac-glycero-3-H-phosphonate, polyamines, polyethylene glycol, adamantane acetic acid, palmitoyl moieties, octadecylamine moieties, hexylaminocarbonyl-oxycholesterol, farnesyl, geranyl and geranylgeranyl moieties.

Certain conjugates can serve as linkers as well. For example, a polyether (such as, for example, a polyethylene glycol) can be used as a linker and protected by a levulinyl group. Once the levulinyl group is removed, the polyether then having a free hydroxyl moiety can be used to attach a label a nucleoside or polynucleotide through the free hydroxyl moiety.

Deoxyribonucleotide

The terms "deoxynucleotide," "deoxyribonucleotide," and "DNA" refer to a nucleotide or polynucleotide comprising at least one moiety that has an H substituted for the OH at the 2'-position of the ribose sugar moiety.

Label

The term "label" includes any suitable detectable moiety known in the art, or that comes to be known. Labels can include, for example, fluorophores, quenchers, chromophores, enzymes, radioisotopes and any other detectable moieties known in the art. Labels can also include, for example, moieties that can be detected by virtue of their specific interaction with a biological molecule, such as the interaction of biotin with avidin or streptavidin, or haptens such as dinitrophenol or digoxigenin with specific antibodies. Conjugates can include labels, with a distinction being that a "label" imparts a desired functionality related to detection or measurement, such as fluorophores, quenchers, chromophores, enzymes, radioisotopes, etc.

Levulinyl Moiety

The phrase "levulinyl moiety" includes a levulinic acid radical, or 4-oxapentanoic acid radical. A levulinyl moiety attached to a group R is illustrated in FIG. 1.

Figure 1:
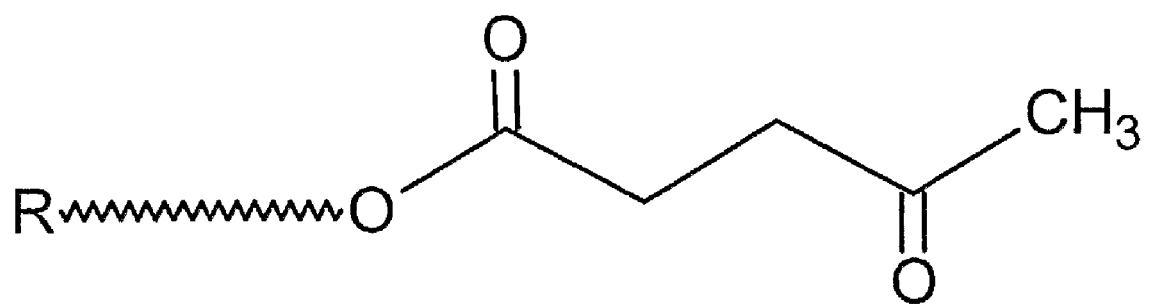
FIG. 1 is a schematic diagram of an embodiment of the invention comprising a levulinyl moiety covalently attached to a linker moiety bound to a nucleic acid. The R group represents a nucleic acid. The squiggled line between the R and the O represents a linker.

It should be noted that in the representation in FIG. 1, the levulinyl moiety is attached to the group R through an ester moiety for illustrative purposes only. The levulinyl moiety can be attached through any suitable chemistry that is orthogonal (i.e., compatible) with respect to the polynucleotide synthesis method selected. Although one suitable attachment of a levulinyl moiety for synthesis of polynucleotides is an ester linkage, an example of an alternative method of attachment is a thioester attachment. In the case of a thioester attachment, the levulinyl moiety comprises a sulfur atom between the carbonyl of the levulinyl moiety and the R group.

The phrase "levulinyl moiety or derivative thereof" includes a levulinic acid radical or a levulinic acid radical wherein one or more oxygen atoms are substituted by sulfur atoms. Additionally, it includes derivatives that produce a levulinic acid radical on deprotection such as, for example, the levulinyl dithioacetal moiety, or are modifications that do not alter the basic protection/deprotection chemistry of the levulinic acid radical but may enhance other properties, such as, for example, the 5-[3-bis(4-methoxyphenyl)hydroxymethyl phenoxy]levulinyl moiety.

Linker

A "linker" includes a moiety that attaches other moieties to each other such as, for example, a nucleotide and its conjugate, or a nucleotide and its label. A linker may be distinguished from a conjugate in that while a conjugate alters the physical properties of a nucleotide, polynucleotide or nucleic acid for some functional purpose, a linker serves to attach a conjugate to the molecule of interest.

By way of example, linkers can comprise modified or unmodified nucleotides, nucleosides, polymers, sugars and other carbohydrates, polyethers such as, for example, polyethylene glycols, polyalcohols, polypropylenes, propylene glycols, mixtures of ethylene and propylene glycols, polyalkylamines, polyamines such as spermidine, polyesters such as poly(ethyl acrylate), polyphosphodiesters, and alkylenes. An example of a conjugate and its linker is cholesterol-TEG-phosphoramidite, wherein the cholesterol is the conjugate and the tetraethyleneglycol (TEG) and phosphate serve as linkers.

Linkers typically comprise difunctionality. That is, they possess functionality (e.g., two functional groups that can be the same or different) that allows for the linker to covalently attach to two other molecules. Linkers can comprise functionalities that allow for the linker to covalently attach to more than two other molecules or entities (e.g., three functional groups that can be the same or different). For example, a linker can have a functionality that allows it to attach to: (1) a solid support; (2) a polynucleotide; and (3) a levulinic acid radical. In this way, for example, a polynucleotide can be synthesized on a support having a linker attached to it, where the linker has functionalities that allow it to attach to the support and allow it also to attach to a nucleotide unit for synthesizing a polynucleotide, while at the same time the linker has a third functionality that is protected by a levulinyl moiety. This type of linker can be employed to attach a label, for example, to the 3' position of a polynucleotide through the linker. In such a case, the polynucleotide is built on the linker rather than the support directly, and the linker typically has a functionality that allows an incoming nucleotide phosphoramidite (i.e., the eventual 3' nucleotide of a polynucleotide) to attach to it, and another functionality protected by a levulinyl moiety. The functionality protected by the levulinyl moiety can be used to attach, for example, a label.

Nucleotide

The term "nucleotide" includes a ribonucleotide or a deoxyribonucleotide or modified form thereof, as well as an analog thereof. Thus, as used herein, nucleotides include nucleosides. Nucleotides include species that comprise purines, e.g., adenine, hypoxanthine, guanine, and their derivatives and analogs, as well as pyrimidines, e.g., cytosine, uracil, thymine, and their derivatives and analogs. A preferable nucleotide has a purine, such as adenine, hypoxanthine, guanine; or a pyrimidine, such as cytosine, uracil, and thymine. For some embodiments, preferably the nucleotide is not a derivative or analog of a nucleotide.

Nucleotide analogs include nucleotides having modifications in the chemical structure of the base, sugar and/or phosphate, including, but not limited to, the 5-position pyrimidine modifications, 7- or 8-position purine modifications, modifications at cytosine exocyclic amines, and substitution of 5-bromo-uracil; and 2'-position sugar modifications, including but not limited to, sugar-modified ribonucleotides in which the 2'-OH is replaced by a group such as an H, OR, R, halo, SH, SR, $NH_2$, NHR, NR2, or CN, wherein R is an alkyl moiety as defined herein. Nucleotide analogs are also meant to include nucleotides with bases such as inosine, queuosine, xanthine, sugars such as 2'-methyl ribose, and non-natural phosphodiester linkages such as methylphosphonates, phosphorothioates and phosphoramidates. Nucleotide analogs are also meant to include non-phosphodiester linkages, such as peptide nucleic acids (PNAs), and non-natural nucleotide modifications, such as locked nucleic acids (LNAs).

The phrase "modified bases" refers to common nucleotide bases such as, for example, adenine, guanine, cytosine, thymine, uracil, and xanthine, that have been modified by the replacement or addition of one or more atoms or groups. Some examples of types of modifications that can comprise nucleotides that are modified with respect to the base moieties, include but are not limited to, alkylated, halogenated, thiolated, aminated, amidated, or acetylated bases, in various combinations. More specific modified bases include, for example, 5-aminoallyluridine, 5-aminoallylcytidine, 5-carboxyvinyluridine, 5-carboxyvinylcytidine, 5-propynyluridine, 5-propynylcytidine, 5-methylcytidine, 5-methyluridine, 5-hydroxymethyluridine, 5-(2-amino)propyl uridine, 5-halocytidine, 5-halouridine, 5-methylaminoethyluridine, 5-methyloxyuridine and other pyrimidine nucleotides having a modification at the 5 position, 6-methyladenine, 6-methylguanine, N,N-dimethyladenine, 2-propyladenine, 2-propylguanine, 2-aminoadenine, 1-methylinosine, 3-methyluridine, 4-acetylcytidine, 1-methyladenosine, 2-methyladenosine, 3-methylcytidine, 6-methyluridine, 2-methylguanosine, 7-methylguanosine, 2,2-dimethylguanosine, deazanucleotides such as 7-deaza-adenosine, 6-azauridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. Modified nucleotides also include those nucleotides that are modified with respect to the sugar moiety, as well as nucleotides having sugars or analogs thereof that are not β-D-ribose. For example, the sugar moieties may be, or be based on, α-D-ribose, mannoses, arabinoses, glucopyranoses, galactopyranoses, 4-thioribose, and other sugars, heterocycles, or carbocycles such as those known in the art as abasic modifications. The term nucleotide is also meant to include what are known in the art as universal bases. By way of example, universal bases include but are not limited to 3-nitropyrrole, 5-nitroindole, or nebularine.

The nitrogenous base moiety can also be modified with a linker, wherein the linker is protected by a levulinyl moiety.

The sugar moiety can also be modified with a linker, wherein the linker is protected by a levulinyl moiety.

Nucleotide Unit

The phrase "nucleotide unit" includes a single nucleotide residue and is comprised of a modified or unmodified nitrogenous base, a modified or unmodified sugar, and a modified or unmodified moiety that allows for linking of two nucleotides together or a conjugate that precludes further linkage. In some embodiments, preferably the nucleotide unit is a single nucleotide residue that is not a nucleotide derivative or a nucleotide analog.

Orthoester

The term "orthoester protected" or "orthoester modified" includes modification of a sugar moiety in a nucleotide unit with an orthoester. Preferably, the sugar moiety is a ribosyl moiety. In general, orthoesters have the structure $RC(OR')_3$ wherein each R' can be the same or different and each R' can be an alkyl group of 1 two about 12 carbon atoms or a substituted alkyl group; R can be an H, an alkyl group of 1 to about 12 carbon atoms, an aryl group, a substituted alkyl group, or a substituted aryl group; and wherein the underscored C is the central carbon of the orthoester. Orthoesters can be employed in a nucleic acid, wherein a carbon of a sugar moiety in a nucleotide unit is bonded to an oxygen, which is in turn bonded to the central carbon of the orthoester. To the central carbon of the orthoester is, in turn, bonded two oxygens, such that in total three oxygens bond to the central carbon of the orthoester. Two oxygens bonded to the central carbon (neither of which is bonded to the carbon of the sugar moiety) in turn, bond to carbon atoms that comprise two moieties that can be the same or different. For example, one of the oxygens can be bound to an ethyl moiety, and the other to an isopropyl moiety. In one example, R can be an H, one R' can be a ribosyl moiety, and the other two R' can be two 2-hydroxyethyl moieties. Orthoesters can be placed at any position on the sugar moiety, such as, for example, on the 2',3' and/or 5' positions. Preferred orthoesters, and methods of making orthoester protected polynucleotides, are described in U.S. Pat. No. 5,889,136 at columns 4-18 and 23-28, incorporated by reference herein, and U.S. Pat. No. 6,008,400 at columns 4-18 and 23-26, incorporated by reference herein.

Polynucleotide

The term "polynucleotide" includes polymers of nucleotides, and includes but is not limited to DNA, RNA, DNA/RNA hybrids including polynucleotide chains of regularly or irregularly alternating deoxyribosyl moieties and ribosyl moieties (for example, wherein alternate nucleotide units have an —OH, then and —H, then an —OH, then an —H, and so on at the 2' position of a sugar moiety). Polynucleotides can have any suitable modified nucleotide units, such as 2'-O-methyl modifications, 2'-halogen modifications, 2'-amine modifications, modified internucleotide linkages, 2'-orthoesters, and the like. Preferably, the polynucleotide comprises unmodified nucleotides (i.e., preferably a polynucleotide comprises ribo- or deoxyribonucleotides of adenine, guanine, thymine, cytosine, hypoxanthine, and uracil, wherein the nitrogenous bases, the sugar moieties, and the internucleotide linkages are unmodified). Where modified, a preferable modification is a 2'-O-alkyl moiety at at least one 2' position of a ribosyl moiety, such as, for example, a 2'-O-methyl modification.

Polyribonucleotide

The term "polyribonucleotide" includes a polynucleotide comprising two or more modified or unmodified ribonucleotides and/or their analogs. Preferably, for most purposes, the polyribonucleotide does not include modified ribonucleotides and/or their analogs (i.e., preferably a polyribonucleotide comprises ribo- or deoxyribonucleotides of adenine, guanine, thymine, cytosine, hypoxanthine, and uracil, wherein the nitrogenous bases, the sugar moieties, and the internucleotide linkages are unmodified). Where modified, a preferable modification is a 2'-O-alkyl moiety at at least one 2' position of a ribosyl moiety, such as, for example, a 2'-O-methyl modification.

Ribonucleotide and Ribonucleic Acid

The term "ribonucleotide" and the phrase "ribonucleic acid" (RNA), include a modified or unmodified nucleotide or polynucleotide comprising at least one ribonucleotide unit. A ribonucleotide unit comprises an OH group attached to the 2'-position of a ribosyl moiety having a nitrogenous base attached in an N-glycosidic linkage in a β-configuration at the 1'-position of a ribosyl moiety, and a moiety that either allows for linkage to another nucleotide or precludes linkage. In some embodiments, preferably the ribonucleotides or RNA do not include modified ribonucleotides and/or their analogs (i.e., preferably a ribonucleotide or RNA comprises ribonucleotides wherein the nitrogenous bases, the sugar moieties, and the internucleotide linkages are unmodified). Additionally, in some embodiments, preferably all nucleotides within the RNA are ribonucleotides. Where modified, a preferable modification is a 2'-O-alkyl moiety at at least one 2' position of a ribosyl moiety, such as, for example, a 2'-O-methyl modification.

siRNA or Short Interfering RNA

The term "siRNA" and the phrase "short interfering RNA" refer to a double stranded nucleic acid that is capable of performing RNA interference (RNAi) and that is 18 to 30 base pairs in length. Additionally, the term siRNA and the phrase "short interfering RNA" include nucleic acids that also contain moieties other than ribonucleotide moieties, including, but not limited to, modified nucleotides, modified internucleotide linkages, non-nucleotides, deoxyribonucleotides and the like. Preferably, for most purposes, the siRNA do not include modified ribonucleotides and/or their analogs (i.e., preferably an siRNA comprises ribonucleotides wherein the nitrogenous bases, the sugar moieties, and the internucleotide linkages are unmodified). Where modified, a preferable modification is a 2'-O-alkyl moiety at at least one 2' position of a ribosyl moiety in an siRNA, such as, for example, a 2'-O-methyl modification.

siRNAs can comprise duplexes of single RNA strands, short hairpin RNAs, RNAs with loops as long as, for example, 4 to 23 or more nucleotides, RNAs with stem-loop bulges, micro-RNAs, and short temporal RNAs. RNAs having loops or hairpin loops can include structures where the loops are connected to the stem by linkers such as flexible linkers. Flexible linkers can be comprised of a wide variety of chemical structures, as long as they are of sufficient length and materials to enable effective intramolecular hybridization of the stem elements. Typically, the length to be spanned is at least about 10-24 atoms.

Compositions comprising nucleic acids bearing one or more linkers covalently attached to a levulinyl moiety, or a derivative of a levulinyl moiety, are described below. Methods for labeling nucleic acid molecules using an orthogonal levulinyl protecting strategy are also described below. The orthogonal levulinyl protecting strategy allows for placement of a linker moiety, covalently attached to a levulinyl moiety or derivative of a levulinyl moiety, at any position in a nucleic acid or at any nucleotide position in a polynucleotide. Nucleic acids, including dinucleotides and polynucleotides, comprising a linker moiety covalently attached to a levulinyl moiety are described. The levulinyl moiety covalently attached to the linker moiety can be removed at any convenient point during synthesis of a nucleic acid polymer, and a suitable moiety, such as, for example, a conjugate or a label, can be covalently attached to the linker moiety.

The present invention improves the ability to efficiently incorporate a conjugate or label at any desirable position in a polynucleotide, at any suitable point during the synthesis of a polynucleotide. This is achieved either by using a phosphoramidite that comprises a linker protected by a levulinyl moiety or derivative thereof, or by using a solid support-bound linker protected by a levulinyl moiety or derivative thereof. Where the linker is covalently attached to the nitrogenous base of the nucleoside phosphoramidite, preferably a 5'-silyl protecting group is used and 2'-orthoester synthesis chemistry is used. Where the linker is attached to the ribosyl moiety of the nucleoside phosphoramidite, for example, at the 2'-position of a ribosyl moiety, any suitable protecting group and synthesis chemistry can be used.

A significant advantage of the invention is the use of the levulinyl moiety to protect the linker. This protecting group is stable to acid, non-aqueous base, and fluoride ion treatment, thus rendering this protection chemistry orthogonal to (compatible with) a variety of solid phase synthesis methods for making polynucleotides. A preferred orthogonal polynucleotide synthesis chemistry for making a polynucleotide comprising a linker protected by a levulinyl moiety is the 2'-orthoester method, disclosed in U.S. Pat. No. 5,889,136 at columns 4-18 and 23-28, incorporated by reference herein, and U.S. Pat. No. 6,008,400 at columns 4-18 and 23-26, incorporated by reference herein. Preferred methods of synthesis using the 2'-orthoester method are disclosed herein.

In one aspect, the invention provides a phosphoramidite comprising a linker covalently attached to a levulinyl moiety.

In another aspect, the invention provides a method for making a protected phosphoramidite, comprising a linker covalently attached to a levulinyl moiety.

In another aspect, the invention provides a nucleoside phosphoramidite, comprising: a protecting group at the 5'-position; a linker moiety covalently attached to the nucleoside phosphoramidite at the 2'-position; and a levulinyl moiety covalently attached to the linker moiety. The 5'-protecting group preferably comprises a 5'-silyl group. The 5'-silyl group preferably comprises a silyl ether.

In another aspect, the invention provides a method for making a levulinyl modified nucleoside phosphoramidite, comprising: covalently attaching a linker to a nucleoside phosphoramidite at the 2'-position, wherein the linker is protected by a levulinyl moiety. The nucleoside phosphoramidite can comprise a thymine moiety, a uracil moiety, an adenine moiety, a guanine moiety, a cytosine moiety, or a hypoxanthine moiety. The nucleoside phosphoramidite can also comprise a 5'-silyl group at its 5'-position.

In another aspect, the invention provides a nucleoside phosphoraridite, comprising: a 5'-silyl protecting group; a linker moiety covalently attached to the nitrogenous base of nucleoside phosphoramidite; and a levulinyl moiety covalently attached to the linker moiety. The 5'-silyl group preferably comprises a silyl ether.

In another aspect, the invention provides a method for making a levulinyl modified nucleoside phosphoramidite. The method comprises: covalently attaching a linker to a nucleoside phosphoramidite, wherein the nucleoside phosphoramidite comprises a 5'-silyl protecting group and the linker is protected by a levulinyl moiety. The silyl protecting group at the 5'-position preferably comprises a silyl ether.

In another aspect, the invention provides a linker covalently attached to a levulinyl moiety and simultaneously attached to a solid support. The mode of attachment to the solid support is preferably through a succinate, glutarate, or oxalate linkage.

In another aspect, the invention provides a method for making a linker covalently attached to a levulinyl moiety and simultaneously attached to a solid support. The mode of attachment to the solid support is preferably through a succinate, glutarate, or oxalate linkage.

In another aspect, the invention provides a method for making a polynucleotide bound to a solid support, comprising: covalently attaching a phosphoramidite comprising a linker protected by a levulinyl moiety to a free 2'-hydroxyl on a nucleotide or polynucleotide on the solid support.

In another aspect, the invention provides a method for making a polynucleotide bound to a solid support, comprising: covalently attaching a linker to a nucleoside phosphoramidite at the 2'-position, wherein the nucleoside phosphoramidite comprises a 5'-protecting group and the linker is protected by a levulinyl moiety; and covalently attaching the nucleoside phosphoramidite to a nucleotide or polynucleotide on the solid support. The silyl protecting group at the 5'-position preferably comprises a silyl ether.

In another aspect, the invention provides a method for making a polynucleotide bound to a solid support, comprising: covalently attaching a linker to a nucleoside phosphoramidite, wherein the nucleoside phosphoramidite comprises a 5'-silyl protecting group and the linker is protected by a levulinyl moiety; and covalently attaching the nucleoside phosphoramidite to a nucleotide or polynucleotide on the solid support. The silyl protecting group at the 5'-position preferably comprises a silyl ether.

In another aspect, the invention provides a method for making a polynucleotide bound to a solid support, wherein the solid support comprises a linker protected by a levulinyl moiety.

Any suitable linker known in the art can be used, as long as the chemistry of the linkage to the nucleoside phosphoramidite is compatible with respect to the method used to synthesize the polynucleotide. Suitable linkers include, for example, polyalcohols, polyethers, substituted or unsubstituted alkyl groups, and substituted or unsubstituted alkenyl groups. The linker preferably comprises an oxygen or a sulfur at one end, wherein the oxygen or the sulfur is capable of being covalently attached to a levulinyl moiety or derivative of a levulinyl moiety. Thus, upon removal of the levulinyl moiety or derivative thereof, the oxygen or sulfur functionality can be used to attach a suitable moiety, for example, a conjugate or label.

A polynucleotide comprising a linking group covalently attached to a levulinyl moiety can be prepared in one of three ways: (1) by adding a linker phosphoramidite with a levulinyl moiety covalently attached thereto to a free 2'-hydroxyl within a growing polynucleotide chain during solid phase synthesis; (2) by adding a nucleoside phosphoramidite comprising a linker with a levulinyl moiety covalently attached thereto, to a growing polynucleotide chain during solid phase synthesis; or (3) by growing a polynucleotide chain using solid phase synthesis on a solid support comprising a linker with a levulinyl moiety covalently attached thereto. The levulinyl moiety can be removed and a desired species, for example a conjugate or a label, can be attached to the linker at any suitable point in time while the polynucleotide (completed or still being synthesized) remains on the support. Preferably, the method of attaching the conjugate or label to the linking group employs a phosphoramidite derivative of the conjugate or label. In this way, the attachment of the conjugate or label takes advantage of highly efficient attachment chemistry as well as the automation afforded by the solid phase methodology. The ability to remove the levulinyl moiety at a precise point in the polynucleotide synthesis enables complete assembly of the polynucleotide chain followed by conjugation or labeling, obviating the repeated exposure of sensitive conjugates or labels to the polynucleotide synthesis chemistry. The invention further provides methods of incorporating two or more different labels or conjugates or combinations thereof at specific sites in a polynucleotide chain during synthesis. This is accomplished by assembling the chain to the desired point of incorporation of the first label or conjugate; incorporating a nucleotide comprising a linker with a levulinyl moiety covalently attached thereto; removing the levulinyl moiety and attaching the first label or conjugate; continuing assembly of the polynucleotide chain to the desired point of incorporation of the second label or conjugate; incorporating a nucleotide comprising a linker with a levulinyl moiety covalently attached thereto; removing the levulinyl moiety and attaching the second label or conjugate; and continuing in this manner until all labels or conjugates are incorporated and the full length polynucleotide chain is obtained. Alternatively, the first label or conjugate may be incorporated at the 3'-terminus of the polynucleotide using a solid support comprising a linker with a levulinyl moiety covalently attached thereto. Additionally, the final label or conjugate may be incorporated at the 5'-terminus of the polynucleotide using the deprotected 5'-hydroxyl of the full length polynucleotide chain.

The invention also provides a method of adding a linker phosphoramidite with a levulinyl moiety covalently attached thereto to a free 2'-hydroxyl within a growing polynucleotide chain during solid phase synthesis. Preferably, the free 2'-hydroxyl will be present on the 3'-terminal nucleotide of the polynucleotide. The free 2'-hydroxyl may be generated in any manner that is compatible with maintaining the integrity of the other protecting groups present on the polynucleotide at that point in the synthesis, as well as with maintaining the linkage between the polynucleotide and the solid support. By way of example, a ribonucleoside phosphoramidite protected with a 5'-silyl group (preferably a silyl ether) and a 2'-orthoester may be coupled with a universal solid support (a support known to those in the art), oxidized to provide a phosphodiester linkage, and the orthoester removed using non-aqueous acid under conditions that provide a free 2'-hydroxyl and that do not degrade the 5'-silyl protection. Alternatively, a solid support modified with a ribonucleoside protected with a 5'-DMT group and a 2'-TBDMS group can be treated with fluoride ion under conditions that provide a free 2'-hydroxyl and that do not degrade the 5'-DMT protection. Those skilled in the art will understand that this approach can be used to add a linker with a levulinyl moiety to one or more free 2'-hydroxyl sites in a polynucleotide containing other 2'-modifications such as 2'-O-methyl, 2'-fluoro, or 2'-deoxy.

The invention further provides a method of adding a nucleoside phosphoramidite comprising a linker with a levulinyl moiety covalently attached thereto, to a growing polynucleotide chain during solid phase synthesis. Standard methods of polynucleotide synthesis, well known to those versed in the art, are used to accomplish this. Multiple nucleosides with levulinyl-protected linkers can be incorporated into a polynucleotide in specific sites as desired.

The invention also provides a solid support comprising a linker protected by a levulinyl moiety. In this aspect, the levulinyl moiety can be attached to any convenient linker, for example, a linker comprising a branched alkyl group. The branched alkyl group can comprise a branch to which a protecting group such as, for example, a dimethoxytrityl group (DMT) or silyl group (such as, for example, a silyl ether) can be attached. In this aspect, the invention allows a first nucleoside phosphoramidite to be added to the linker comprising the protected group, such as the DMT or silyl group, thus allowing a convenient and orthogonal method for attaching a molecule of interest, for example a conjugate or label, to the 3'-most unit of a polynucleotide.

In another aspect, the invention provides a composition, comprising:

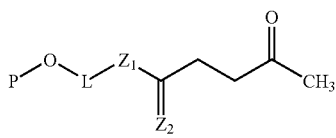

wherein L comprises a linker; $Z_1$ is an oxygen or a sulfur; $Z_2$ is an oxygen or a sulfur; and P comprises a phosphoramidite moiety. Preferably, $Z_1$ and $Z_2$ are each oxygen. Preferred phosphoramidite moieties for P are methyl N,N(diisopropyl)amino phosphoramidite and 2-cyanoethyl N,N(diisopropyl) amino phosphoramidite.

In another aspect, the invention provides a composition, comprising:

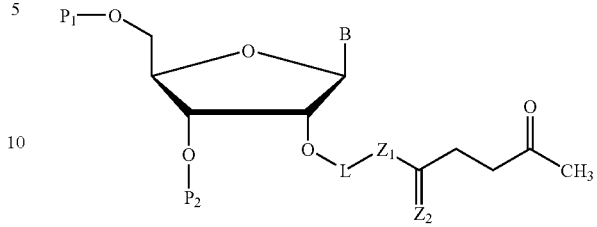

wherein B comprises a nitrogenous base that is modified or unmodified; L comprises a linker; $Z_1$ is an oxygen or a sulfur; $Z_2$ is an oxygen or a sulfur; $P_1$ comprises a blocking group; and $P_2$ comprises a phosphoramidite moiety. $P_1$ can comprise any suitable protecting moiety. $P_1$ preferably comprises a dimethoxytrityl moiety or a silyl ether moiety. Preferably, $Z_1$ and $Z_2$ are each oxygen. Preferred phosphoramidite moieties for $P_2$ are methyl N,N(diisopropyl)amino phosphoramidite and 2-cyanoethyl N,N(diisopropyl)amino phosphoramidite. B preferably comprises a protected nitrogenous base.

In another aspect, the invention provides a composition, comprising:

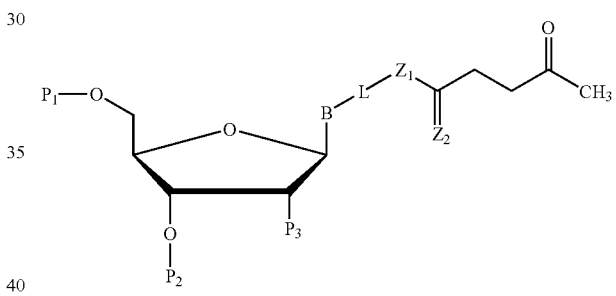

wherein B comprises a nitrogenous base that is modified or unmodified; L comprises a linker; $Z_1$ is an oxygen or a sulfur; $Z_2$ is an oxygen or a sulfur; $P_1$ comprises a blocking group; $P_2$ comprises a phosphoramidite moiety; and $P_3$ comprises H, or a halogen atom, or oxygen-$Q_1$, where Q, comprises a blocking moiety, or sulfur-$Q_2$, where $Q_2$ comprises a blocking moiety, or NH-$Q_3$, where $Q_3$ comprises a blocking moiety. $P_1$ can comprise any suitable protecting moiety. $P_1$ preferably comprises a dimethoxytrityl moiety or a silyl ether moiety. Preferred phosphoramidite moieties for $P_2$ are methyl N,N (diisopropyl)amino phosphoramidite and 2-cyanoethyl N,N (diisopropyl)amino phosphoramidite. $Q_1$, $Q_2$ and $Q_3$ comprise any suitable protecting group, or an alkyl group. $Q_1$ preferably comprises a silyl ether, most preferably t-butyldimethylsilyl ether (TBDMS), or a silyl oxymethyl ether, most preferably triisopropylsilyl oxymethyl ether (TOM), when $P_1$ is dimethoxytrityl; $Q_1$ preferably comprises an orthoester, most preferably bis(acetoxyethyl)orthoester (ACE), when $P_1$ is a silyl ether. $Q_2$ preferably comprises a thioacetal or thioether. $Q_3$ preferably comprises trifluoroacetyl or phthalimido. Preferably, $Z_1$ and $Z_2$ are each oxygen. B preferably comprises a protected nitrogenous base.

In another aspect, the invention provides a composition, comprising:

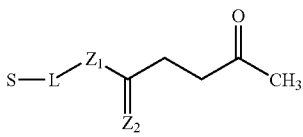

wherein L comprises a linker; $Z_1$ is an oxygen or a sulfur; $Z_2$ is an oxygen or a sulfur; and S comprises a solid support useful for the synthesis of nucleic acids. Preferably, $Z_1$ and $Z_2$ are each oxygen. S is preferably controlled pore glass or cross-linked polystyrene.

An advantage of the present invention includes the ability to efficiently prepare an RNA, for example, an siRNA, wherein the RNA comprises one or more labels or conjugates.

Having described the invention with a degree of particularity, examples will now be provided. These examples are not intended to and should not be construed to limit the scope of the claims in any way. Although the invention may be more readily understood through reference to the following examples, they are provided by way of illustration and are not intended to limit the present invention unless specified.

EXAMPLES

All reagents and solvents used in the following examples were obtained from commercial sources and are of the highest quality available. The following abbreviations are used: DMTr-Cl, 4,4'-dimethoxytrityl chloride; DCM, dichloromethane; DCC, N,N'-dicyclohexylcarbodiimide; TEA, triethylamine; DMAP, 4-dimethylaminopyridine; TLC, thin layer chromatography; MeOH, methanol; TIPDS-$Cl_2$, 1,3-dichloro-1,1,3,3-tetraisopropyldisiloxane; BZH-Cl, benzhydryloxy-bis(trimethylsilyloxy)chlorosilane; TMS-Cl, trimethylsilyl chloride; TEMED, N,N,N',N'-tetramethylethylenediamine; DMF, N,N-dimethylformamide; THF, tetrahydrofuran; TBAF, tetrabutylammonium fluoride trihydrate; BOP, (benzotriazol-1-yloxy)this(dimethylamino)phosphonium hexafluorophosphate; HOBt, 1-hydroxybenzotriazole monohydrate; TBDMS-Cl, tert-butyldimethylsilyl chloride; CDI, N,N'-carbonyl diimidazole; DOD-Cl, cylcododecyloxy-bis(trimethylsilyloxy)chlorosilane.

Example 1

Synthesis of a Linker Phosphoramidite Protected by a Levulinyl Moiety

Phosphoramidites comprising a linker moiety protected by a levulinyl group, or derivatives thereof, were prepared in the manner described below. In general, an excess of a diol was reacted with dimethoxytrityl chloride in pyridine under conditions that provided a suitably good yield of mono-tritylated species. The free hydroxyl on the mono-tritylated diol was then esterified using levulinic anhydride in pyridine, and the trityl group was removed using anhydrous acid. Finally, the mono-levulinic ester of the diol was treated with a bis(diisopropylamino)alkoxy phosphine in the presence of a tetrazole catalyst to give the desired phosphoramidite. The method is illustrated in FIG. 2 and detailed below for the specific case of a triethylene glycol linker.

Figure 2:
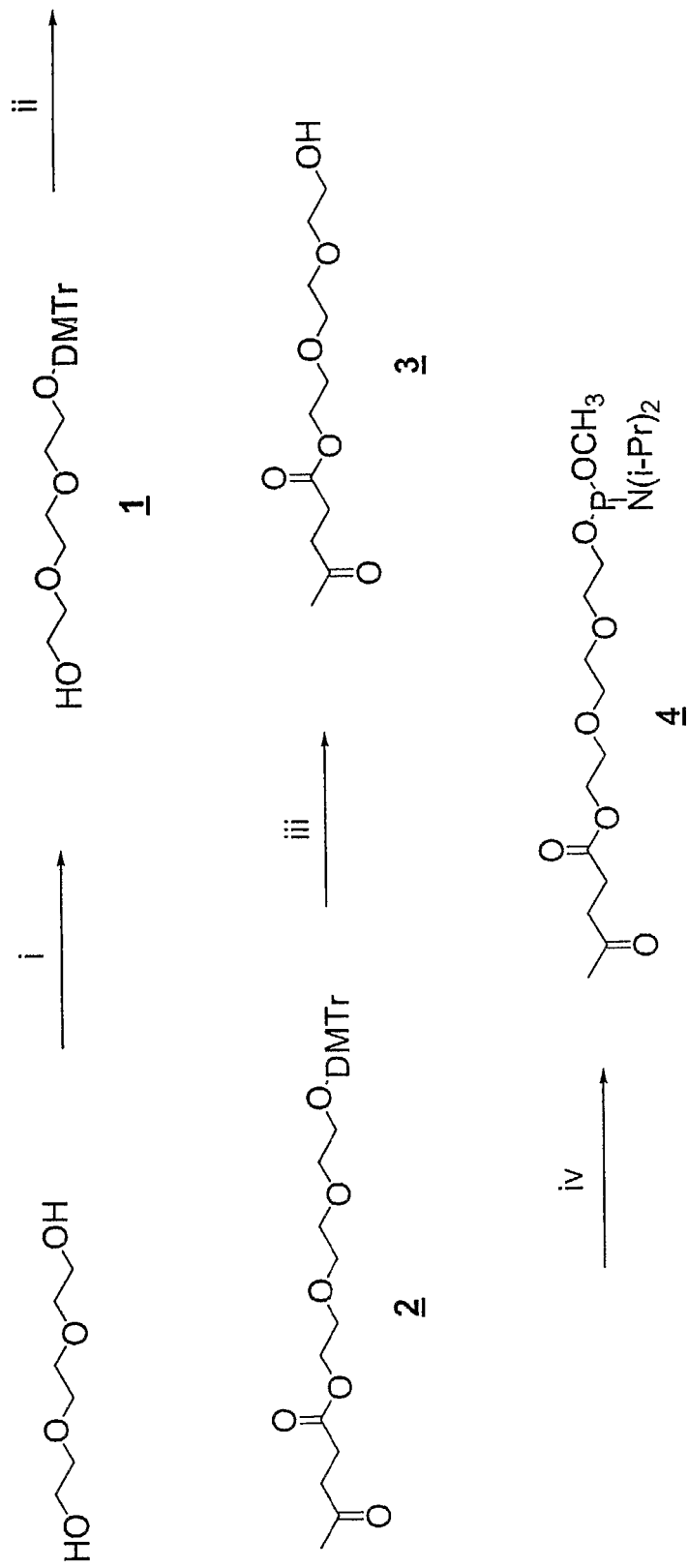
FIG. 2 is a schematic representation of the synthesis of one embodiment of a linker phosphoramidite, wherein the linker is protected by a levulinyl moiety. The reaction conditions include: (i) DMTr-Cl/TEA/pyridine; (ii) levulinic anhydride/DMAP/pyridine; (iii) trifluoroacetic acid/DCM; (iv) bis(diisopropylamino)methoxy phosphine/5-ethylthio-1H-tetrazole/diisopropylamine/DCM.

Synthesis of Triethylene Glycol Mono-Levulinic Acid Ester (N,N,-Diisopropylamino)Methoxy Phosphorammidite (4) (FIG. 2)

Triethylene glycol mono-4,4'-dimethoxytrityl Ether (1)

10.0 g (68.6 moles) of triethylene glycol was twice co-evaporated with 50 mL of dry pyridine, and was then dissolved in 100 mL of dry pyridine. 3.5 mL (25.1 mmoles) of triethylamine were added, followed by 8.0 g (23.6 mmoles) of DMTr-Cl. The mixture was stirred at room temperature overnight. The mixture became somewhat thickened from triethylammonium chloride formation. The mixture was then evaporated to a thick syrup, and dissolved in 300 mL of ethyl acetate. The mixture was washed twice with 100 mL of water, and then once with 50 mL of saturated aqueous sodium chloride. The combined aqueous washes were back extracted with 50 mL of ethyl acetate. The ethyl acetate extracts were combined and dried over anhydrous magnesium sulfate, then filtered. The filtrate was evaporated to a yellow oil. Flash chromatography was carried out on 250 mL of silica gel, using a gradient of ethyl acetate in hexanes (1:3 (v/v) to 100% ethyl acetate) containing 2% (v/v) TEA. Product fractions were combined, evaporated, and dried overnight in vacuo to give a pale yellow syrup. The yield was 7.7 g (72%)

Triethylene Glycol Mono-4,4'-Dimethoxytrityl Ether Mono-Levulinic Acid Ester (2)

23.2 g of levulinic acid (200 mmoles) was dissolved in 250 mL of DCM, and 20.6 g (100 mmoles) of DCC were added. The reaction mixture warmed and a white precipitate formed. The reaction was stirred overnight at room temperature. The mixture was then filtered, the solid was washed with DCM, and the filtrate was evaporated to dryness, yielding 23.0 g (107%) of levulinic acid anhydride. The product was contaminated with a small amount of N,N'-dicyclohexylurea.

7.6 g (16.8 mmoles) of compound 1 were co-evaporated with 50 mL of dry pyridine and then dissolved in 100 mL of dry pyridine. 0.4 g (3.4 mmoles) of DMAP was added, followed by 4.0 g (18.5 mmoles) of levulinic acid anhydride. The mixture was stirred at room temperature for two days. The mixture was evaporated to a brown oil, which was then dissolved in 300 mL of ethyl acetate. The dissolved oil was washed once with 100 mL of saturated sodium bicarbonate, then once with 100 mL of saturated sodium chloride, and the solution was dried over magnesium sulfate, filtered, and evaporated. Flash chromatography was carried out on 250 mL of silica gel, using a mixture of 1:2 (v/v) ethyl acetate in hexanes containing 2% (v/v) TEA. Product fractions were pooled and evaporated to a thick, pale yellow syrup, which was dried overnight in vacuo. The yield was 9.0 g (97%).

Triethylene Glycol Mono-Levulinic Acid Ester (3)

9.5 g (17.3 mmoles) of compound 2 were dissolved in 100 mL of DCM. 1 mL of trifluoroacetic acid was added, and the reaction mixture immediately turned orange. The mixture was stirred for 30 minutes at room temperature. TLC (1:1 (v/v)ethyl acetate:hexanes and 2% (v/v) TEA) showed the reaction was about 50% complete. An additional 1 mL of trifluoroacetic acid was performed and the reaction was stirred for 30 more minutes at room temperature. TLC indicated that the reaction was then about 90% complete. An additional 1 mL of trifluoroacetic acid was added and the mixture was stirred for 15 additional minutes at room temperature. TLC then indicated that the reaction was complete. The reaction mixture was concentrated to about 25 mL, resulting in a dark orange syrup, which was loaded directly onto a 200 mL silica gel column. Flash chromatography was carried out using a gradient of MeOH in DCM (100% DCM to 100% MeOH). Product fractions were combined, evaporated, and dried overnight in vacuo to give a tan oil. The yield was 3.6 g (84%).

Triethylene Glycol Mono-Levulinic Acid Ester (N,N,-Disopropylamino)Methoxy Phosphoramidite (4)

3.6 g (14.5 mmoles) of compound 3 were dissolved in 30 mL of DCM and 2.1 mL (14.5 mmoles) of diisopropylamine were added. The reaction flask was capped with a rubber septum and the solution was stirred at room temperature. In another flask, 4.2 g (1.1 mmoles) of bis(diisopropylamino) methoxy phosphine were dissolved in 30 mL of DCM. 2.1 mL (14.5 mmoles) of diisopropylamine were added, followed by 16.2 mL of a 0.45 M solution of 5-ethylthio-1H-tetrazole in anhydrous acetonitrile (7.3 mmoles). The container was sealed and the reaction was mixed well by swirling. After 5 minutes-at room temperature, the activated phosphine solution was added to the solution of 3 and the reaction was stirred for 6 hours. 8.5 mL of anhydrous ethanol were added, and the reaction mixture was evaporated to a thick oil. Flash chromatography was carried out on 150 mL of silica gel, using a gradient of ethyl acetate in hexanes (100% hexanes to 1:3 (v/v)) containing 1% (v/v) TEA. Product fractions were pooled and 50 mL of toluene were added. The solvent was evaporated and the resulting clear liquid was coevaporated twice with 50 mL portions of anhydrous acetonitrile. The product was then dried overnight in vacuo to give a clear, colorless viscous liquid. The yield was 3.3 g (55%).

Example 2

Synthesis of a Nucleoside Phosphoramidite with a Linker Protected by a Levulinyl Moiety at the 2'-Position of the Ribosyl Moiety—Method 1

A nucleoside phosphoramidite comprising a linker protected by a levulinyl moiety, or derivative thereof, attached to the 2'-position of the ribosyl moiety was prepared in the manner described below.

In general, a ribonucleoside was first prepared having a linker covalently attached to the 2'-hydroxyl through an ether bond. The 2'-modified nucleoside was then simultaneously protected at its 3'- and 5'-hydroxyl groups. The nucleoside was next protected at the nitrogenous base as necessary using standard procedures (for example, adenosine and guanosine with isobutyryl, or cytidine with acetyl). The linker was modified with a levulinyl moiety. The protecting groups on the 3'- and 5'-hydroxyl groups were removed and the 5'-hydroxyl was protected in a manner appropriate to the polynucleotide synthesis chemistry to be employed (for example, with DMTr-Cl in pyridine or with benzhydryloxy-bis(trimethylsilyloxy)chlorosilane in dichloromethane and diisopropylamine). Finally, the free 3'-hydroxyl was reacted with an appropriate phosphine (for example, bis(diisopropylamino) methoxy phosphine in the presence of a tetrazole catalyst) to produce the desired nucleoside phosphoramidite. The methods are illustrated in FIGS. 3, 4, 5, 6, 7, 8, 9 and 10, and detailed below for the particular examples given.

Figure 3:
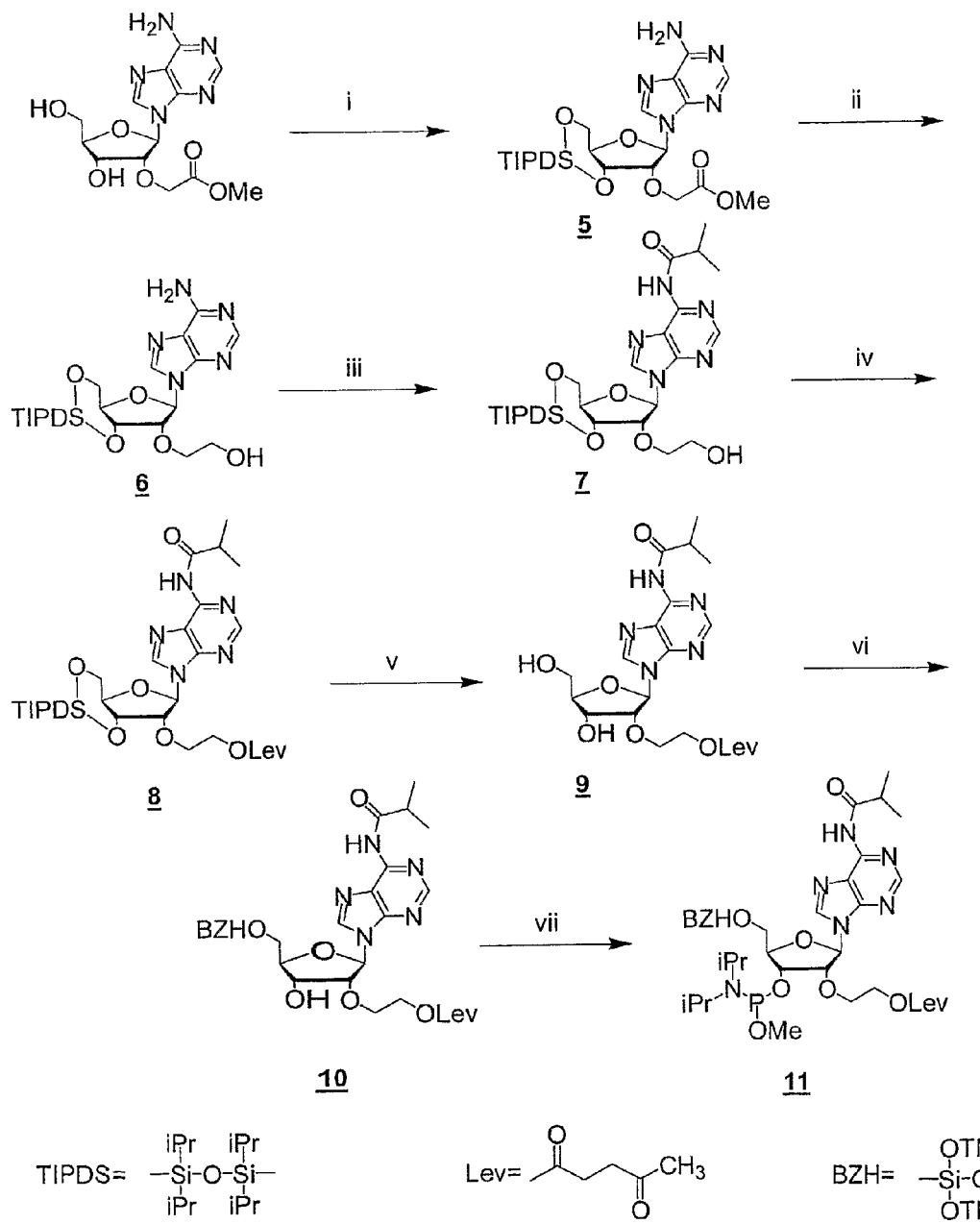
FIG. 3 is a schematic representation of the synthesis of one embodiment of a protected nucleoside phosphoramidite having a linker protected by a levulinyl moiety. In this case the nucleotide base is adenine, and the linker is attached to the 2'-hydroxyl by an ether linkage. The reaction conditions include: (i) TIPDS-Cl$_2$/pyridine; (ii) sodium borohydride/ethanol/DCM; (iii) a) TMS-Cl/pyridine; b) isobutyryl chloride; c) ammonium hydroxide; (iv) levulinic anhydride/TEA/DMAP/DCM; (v) TEMED/hydrofluoric acid/acetonitrile; (vi) BZH-Cl/diisopropylamine/DCM; (vii) bis(diisopropylamino)methoxy phosphine/5-ethylthio-1H-tetrazole/diisopropylamine/DCM.

Synthesis of $N^6$-Isobutyryl-5'-O-[Benzhydryloxy-Bis (Trimethylsilyoxy)Silyl]-2'-O-[2-(4-Oxopentanoate) Oxyethyl)]Adenosine 3'-O-(N,N,-Diisopropylamino) Methoxy Phosphoramidite (11) (FIG. 3)

2'-O-(Methoxycarbonylmethylene)-3',5'-O-(Tetraisopropyldisiloxane-1,3-Diyl)Adenosine (5)

2'-O-(methoxycarbonylmethylene)adenosine was prepared as described in the following references: U.S. Pat. No. 6,403,779 to Kawasaki, A. M., Fraser, A. S., Manoharan, M., Cook, D. P., and Prakash, T. P.; Jin, S., Miduturu, C. V., McKinney, D. C., and Silverman, S. (2005) "Synthesis of Amine- and Thiol-Modified Nucleoside Phosphoramidites for Site-Specific Introduction of Biophysical Probes into RNA" *J. Org. Chem.* 70, 4284-4200.

To a stirred solution of 2'-O-(methoxycarbonylmethylene) adenosine (8.48 g, 25 mmoles) in pyridine 125 mL at 0° C. (ice/water bath) were dropwise added TIPDS-$Cl_2$ (8.31 g, 26.3 mmoles) over 30 minutes. After stirring for 16 hours the reaction was stopped by the addition of MeOH (30 mL) and evaporated to dryness. The resulting paste was partitioned between DCM and saturated aqueous sodium bicarbonate. The organic layer was further washed with saturated aqueous sodium chloride and dried by passage through anhydrous sodium sulfate The crude mixture was purified by flash chromatography on 400 mL silica gel using a gradient of ethyl acetate in DCM (2:8 (v/v) to 7:3 (v/v)). Product fractions were pooled and evaporated to give the product as a white foam. The yield was 7.45 g (51%). $^1$H NMR δ ($CDCl_3$, 400 MHz) 8.29 (s, 1 H), 8.09 (s, 1 H), 6.11 (s, 1 H), 5.59 (b, 2 H), 4.90 (dd, J=4.4 Hz, J=9.2 Hz, 1 H), 4.62 (d, J=16.8 Hz, 1 H), 4.44-4.43, (m, 1 H), 4.43 (d, J=16.8 Hz, 1 H), 4.23-4.17 (m, 2 H), 4.02 (dd, J=2.8 Hz, J=13.4 Hz, 1 H), 3.73, (s, 1 H), 1.22-0.97 (m, 28 H).

2'-O-(Hydroxyethyl)-3',5'-O-(Tetraisopropyldisiloxane-1,3-Diyl)Adenosine (6)

Compound 5 (5.61 g, 9.7 mmoles) was dissolved in 30 mL of DCM and diluted with 70 mL of absolute ethanol. This solution was cooled to 0° C. (ice/water bath) and sodium borohydride (0.73 g, 19.3 mmoles) was added. The reaction was allowed to warm to ambient temperature and after 16 hours a second portion of sodium borohydride (0.40 g, 10.4 mmoles) was added. The reaction was evaporated to dryness after a total reaction time of 40 hours, and the resulting paste was partitioned between ethyl acetate and water. The organic solution was dried by passage through anhydrous sodium sulfate and concentrated. The crude material was purified by flash chromatography on 400 mL silica gel, using a gradient of ethyl acetate and acetone in hexanes (0:2:8 (v/v) to 2:6:2 (v/v) containing 3% (v/v) MeOH). Product fractions were pooled and evaporated to afford the product as a white solid. The yield was 3.81 g or 71%. $^1$H NMR δ ($CDCl_3$, 400 MHz) 8.32 (s, 1 H), 8.18 (s, 1 H), 6.08 (b, 2 H), 4.61 (dd, J=3.6 Hz, J=7.2 Hz, 1 H), 4.28-4.26 (m, 2 H), 4.17 (m, 1 H), 4.05-3.95 (m, 3 H), 3.82-3.78 (m, 2 H), 1.10-0.96 (m, 28 H); ESMS: (M+H) calculated 554.28, observed 554.24.

2'-O-(Hydroxyethyl)-$N^6$-Isobutyryl-3',5'-O-(Tetraisopropyldisiloxsane-1,3-Diyl)Adenosine (7)

Compound 6 (3.81 g, 6.9 mmoles) was dissolved in 70 mL of pyridine, cooled to 0° C. (ice/water bath) and TMS-Cl (1.50 g, 13.8 mmoles) was added. After 1 hour, isobutyryl chloride (1.47 g, 13.8 mmoles) was added and the solution was warmed to ambient temperature. The mixture was stirred overnight, then cooled to 0° C. (ice/water bath) and water (40 mL) was added. After stirring for 20 minutes, concentrated ammonium hydroxide (30 mL) was added and the mixture was stirred for an additional 30 minutes. The solution was then evaporated to dryness and purified by flash chromatography. Product fractions were pooled and evaporated to leave a white solid. The yield was 4.18 g (97%). $^1$H NMR δ (CDCl$_3$, 400 MHz) 8.96 (b, 1 H), 8.69 (s, 1 H), 8.33 (s, 1 H), 6.10 (s, 1 H), 4.62 (dd, J=4.4 Hz, J=9.4 Hz, 1 H), 4.28-4.20 (m, 2 H), 4.17-4.16 (m, 1 H), 4.04-3.96 (m, 3 H), 3.81-3.78 (m, 2 H), 3.20-3.14 (m, 1 H), 2.46-2.38 (m, 1 H), 1.17 (d, J=4.0 Hz, 6 H), 1.10-0.98 (m, 28H); ESMS (M+H): calculated 624.33, observed 624.34.

N$^6$-Isobutyryl-2'-O-[2-(4-Oxopentanoate)Oxyethyl)]-3',5'-O-(Tetraisopropyldisiloxane-1,3-Diyl) Adenosine (8)

To a solution of DCC (0.50 g, 2.45 mmoles) in 25 mL of DCM were added levulinic acid (0.57 g, 4.90 mmoles). After 30 minutes the white precipitate was filtered away and the clear solution was evaporated to dryness. To this flask was added compound 7 (1.02 g, 1.63 mmoles) in 30 mL of DCM, TEA (0.66 g, 6.52 mmoles), and DMAP (0.04 g, 0.33 mmoles). After 1 hour the mixture was diluted with DCM and washed with saturated aqueous sodium bicarbonate. The organic phase was further washed with saturated aqueous sodium chloride and dried by passage through anhydrous sodium sulfate. Evaporation of the solvent left a light brown paste (8) that was used in the next reaction without further purification.

N$^6$-Isobutyryl-2'-O-[2-(4-Oxopentanoate)Oxyethyl)] Adenosine (9)

To a solution of TEMED (1.3 mL, 8.2 mmoles) in 10 mL of acetonitrile at 0° C. (ice/water bath), 48% aqueous hydrofluoric acid (0.2 mL, 5.7 mmoles) was added dropwise. This solution was allowed to stir for 5 minutes and was then added to compound 8 (1.18 g, 1.63 mmoles) in a separate flask. The reaction was stirred for 2.5 hours and concentrated to dryness. The crude material was purified by flash chromatography on 50 mL of silica gel using a gradient of MeOH in ethyl acetate (0 to 4% (v/v)) containing 0.1% TEMED (v/v). Product fractions were pooled and evaporated to afford a white foam after drying in vacuo. The yield was 0.64 g (81%).

N$^6$-Isobutyryl-5'-O-[Benzhydryloxy-Bis(Trimethylsilyloxy)Silyl]-2'-O-[2-(4-Oxopentanoate)Oxyethyl)] Adenosine (10)

To a solution of compound 9 (0.64 g, 1.33 mmoles) in 10 mL of DCM, diisopropylamine (0.13 g, 1.33 mmoles) was added. The solution was cooled to 0° C. (ice/water bath). In a separate flask, BZH-CL (1.14 g, 2.66 mmoles) was dissolved in 10 mL of DCM. Diisopropylamine (0.32 g, 3.19 mmoles) was added this solution dropwise over 1 minute. The silylation solution was then added dropwise to the solution of compound 9 at 0° C. and the reaction is continued until TLC analysis showed complete consumption of starting material. The reaction was stopped by the addition of 5 mL of MeOH and evaporated to dryness. The crude material was purified by flash chromatography on 60 mL of silica gel using a gradient of ethyl acetate and acetone in hexanes (2:0:8 to 2:2:6 (v/v/v)) containing 0.1% (v/v) TEA. Product fractions were pooled and evaporated to afford a colorless oil. The yield was 0.87 g (75%). ESMS (M+H): calculated 868.33, observed 868.46.

N'-Isobutyryl-5'-O-[Benzhydryloxy-Bis(Trimethylsilyloxy)silyl]-2'-O-[2-(4-Oxopentanoate)Oxyethyl)] Adenosine 3'-O-(N,N,-Diisopropylamino)Methoxy Phosphoramidite (11)

Bis(diisopropylamino)methoxy phosphine (0.40 g, 1.50 mmoles) was dissolved in 5 mL of DCM and a 0.45 M solution of 5-ethylthio-1H-tetrazole in anhydrous acetonitrile (1.1 mL, 0.5 mmoles) was added. Diisopropylamine (0.10 g, 1.0 mmoles) was then added and the phosphine solution was allowed to stir for 5 minutes at ambient temperature. In a separate flask compound 10 (0.87 g, 1.0 mmoles) and diisopropylamine (0.10 g, 1.0 mmoles) were dissolved in 5 mL of DCM. The activated phosphine solution was added into the nucleoside solution and the reaction was stirred at room temperature. After 16 hours the reaction was quenched with 5 mL of absolute ethanol and concentrated to dryness. The resulting paste was purified by flash chromatography on 50 mL of silica gel using a mixture of DCM in hexanes (5:95 (v/v)) containing 1% (v/v) TEA followed by acetone in hexanes (2:8 (v/v)) containing 0.1% (v/v) TEA. Product fractions were pooled and evaporated to afford a colorless oil. The yield was 0.79 g (77%). ESMS: (M+Na) calculated 1164.42, observed 1164.56.

Figure 4:
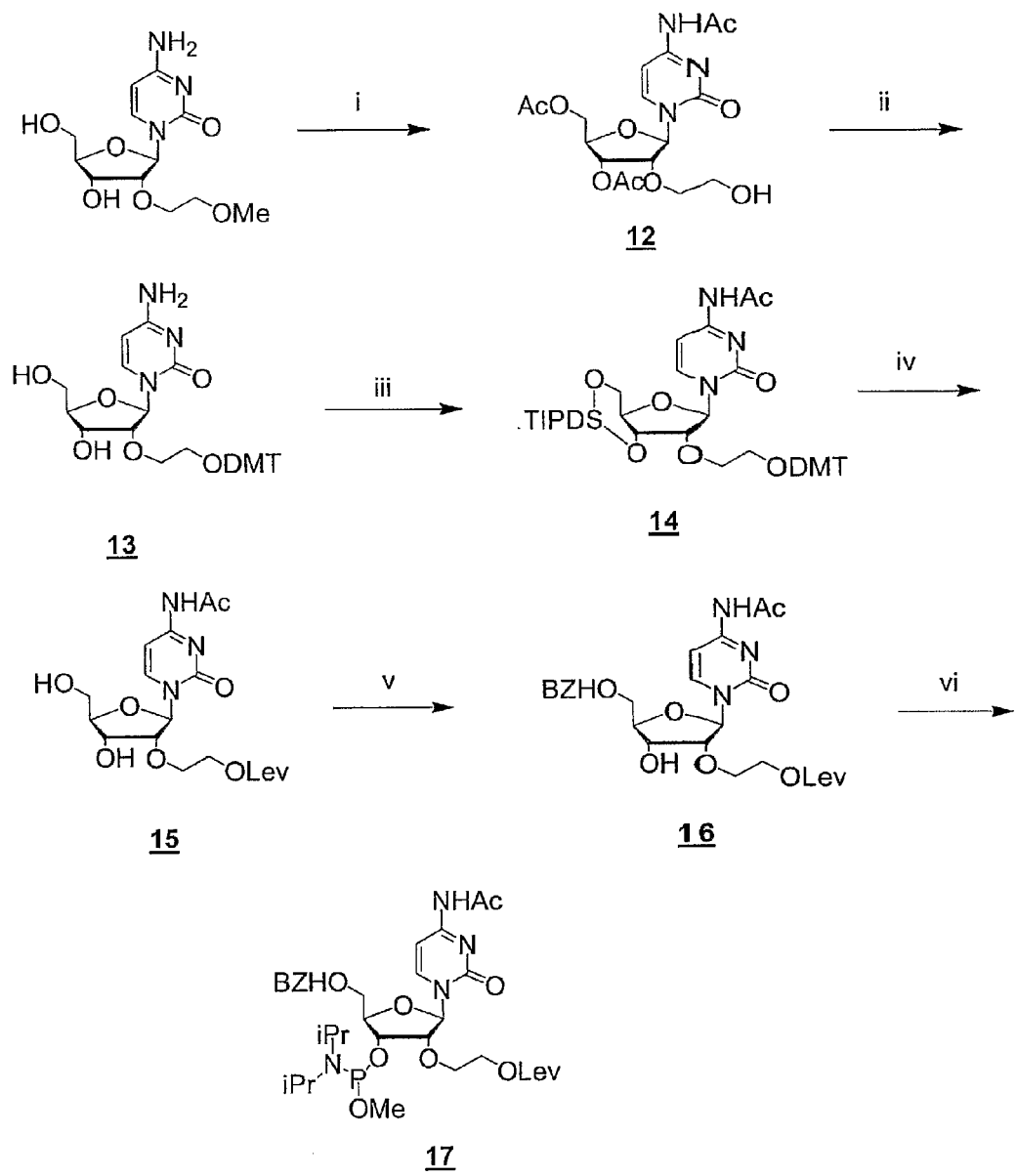
FIG. 4 is a schematic representation of the synthesis of one embodiment of a protected nucleoside phosphoramidite having a linker protected by a levulinyl moiety. In this case the nucleotide base is cytosine, and the linker is attached to the 2'-hydroxyl by an ether linkage. The reaction conditions include: (i) a) acetic anhydride/pyridine/DMAP; b) trimethylsilyl iodide/acetonitrile; (ii) a) DMTr-Cl/pyridine; b) potassium carbonate/MeOH; (iii) a) TIPDS-Cl$_2$/pyridine; b) acetic anhydride; (iv) a) ammonium cerium(IV) nitrate/2-propanol; b) levulinic anhydride/TEA/DMAP/DCM; c) TEMED/hydrofluoric acid/acetonitrile; (v) BZH-Cl/diisopropylamine/DCM; (vi) bis(diisopropylamino)methoxy phosphine/5-ethylthio-1H-tetrazole/diisopropylamine/DCM.
Figure 5:
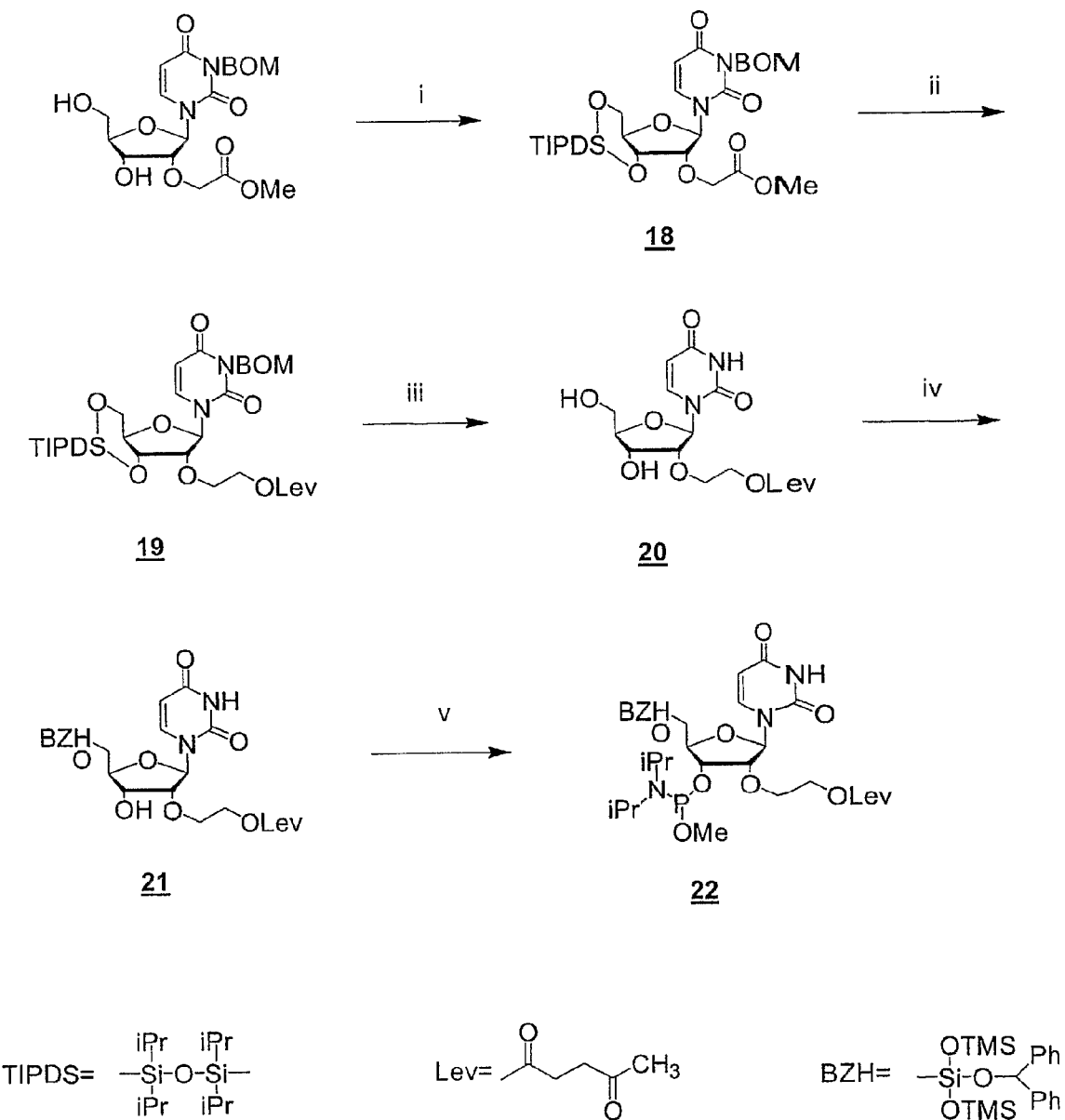
FIG. 5 is a schematic representation of the synthesis of one embodiment of a protected nucleoside phosphoramidite having a linker protected by a levulinyl moiety. In this case the nucleotide base is uracil, and the linker is attached to the 2'-hydroxyl by an ether linkage. The reaction conditions include: (i) TIPDS-Cl$_2$/pyridine; (ii) a) sodium borohydride/ethanol; b) levulinic anhydride/TEA/DMAP/DCM; (iii) a) 10% Pd/C/H$_2$/MeOH; b) TEMED/hydrofluoric acid/acetonitrile; (iv) BZH-Cl/diisopropylamine/DCM; (v) bis(diisopropylamino)methoxy phosphine/5-ethylthio-1H-tetrazole/diisopropylamine/DCM.
Figure 6:
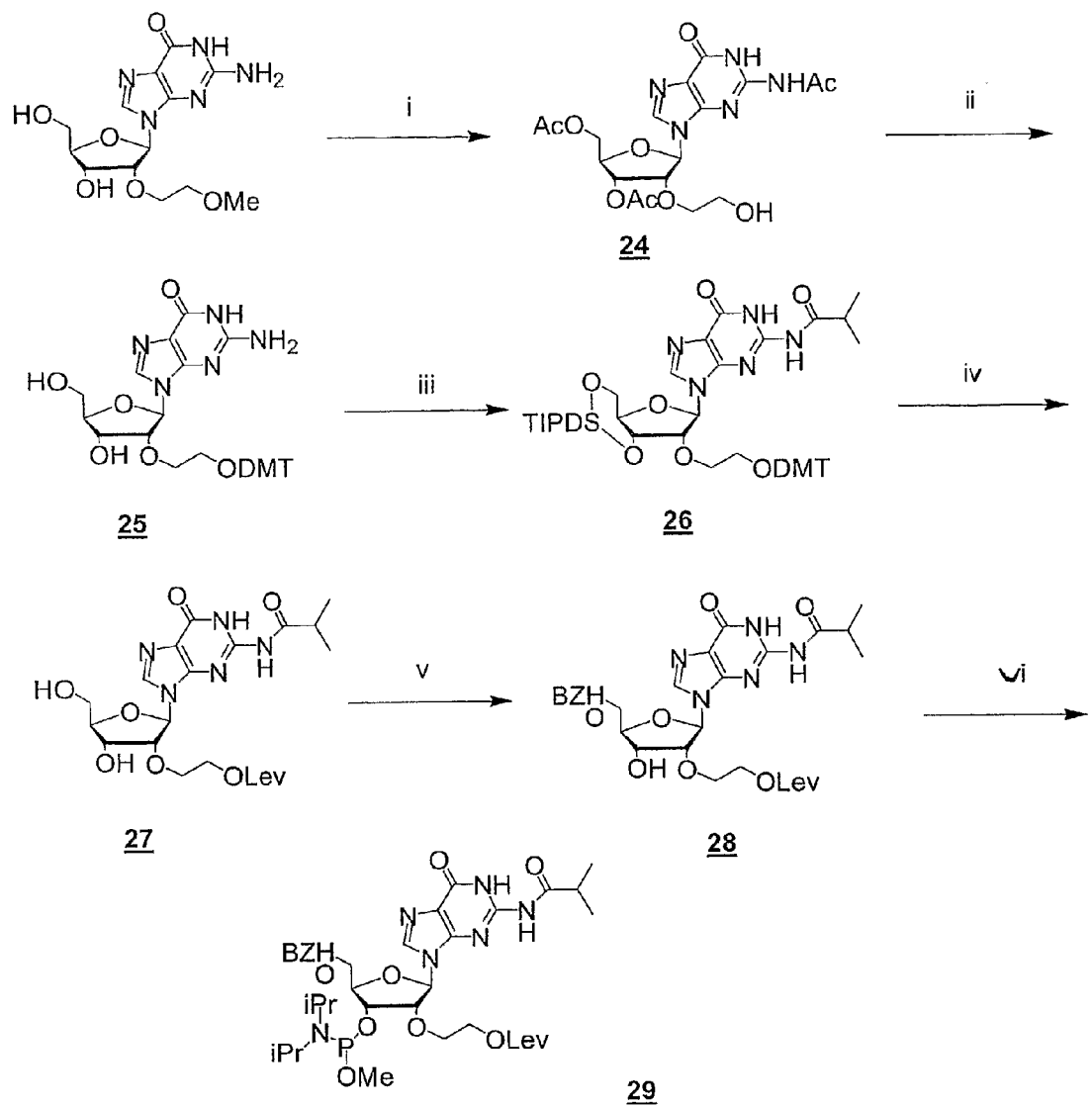
FIG. 6 is a schematic representation of the synthesis of one embodiment of a protected nucleoside phosphoramidite having a linker protected by a levulinyl moiety. In this case the nucleotide base is guanine, and the linker is attached to the 2'-hydroxyl by an ether linkage. The reaction conditions include: (i) a) acetic anhydride/pyridine/DMAP; b) trimethylsilyl iodide/acetonitrile; (ii) a) DMTr-Cl/pyridine; b) potassium carbonate/MeOH; (iii) a) TIPDS-Cl$_2$/pyridine; b) isobutyric anhydride; (iv) a) ammonium cerium(IV) nitrate/2-propanol; b) levulinic anhydride/TEA/DMAP/DCM; c) TEMED/hydrofluoric acid/acetonitrile; (v) BZH-Cl/diisopropylamine/DCM; (vi) bis(diisopropylamino)methoxy phosphine/5-ethylthio-1H-tetrazole/diisopropylamine/DCM.
Figure 6:
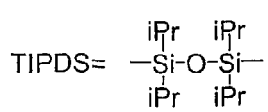
Figure 6:
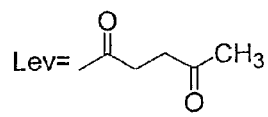
Figure 6:
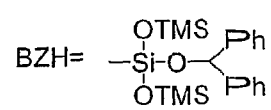

Synthesis of N$^4$-Acetyl-5'-O-[Benzhydryloxy-Bis(Trimethylsilyloxy)Silyl]-2'-O-[2-(4-Oxopentanoate) Oxyethyl)]Cytidine 3'-O-(N,N,-Diisopropylamino) Methoxy Phosphoramidite (17) (FIG. 4)

2'-O-(Hydroxyethyl)-N$^4$,3',5'-O-Triacetylcytidine (12)

2'-O-(Methoxyethyl)cytidine was prepared as described in the following reference: Legorburu, U., Reese, C. B., and Song, Q. (1999) "Conversion of Uridine into 2'-O-(2-Methoxyethyl)-uridine and 2'-O-(2-Methoxyethyl) cytidine" *Tetrahedron* 55, 5635-5640.

Acetic anhydride (11.45 g, 112.3 mmoles) was added to a solution of (2'-O-methoxyethyl)cytidine (5.64 g, 18.7 mmoles) in 47 mL of pyridine. The mixture was stirred for 14 hours and quenched with MeOH (20 mL). The solution was evaporated to dryness and partitioned between DCM and saturated aqueous sodium bicarbonate. The organic phase was further washed with saturated aqueous sodium chloride and dried by passage through anhydrous sodium sulfate. Evaporation of the solvent left an off-white foam. ESMS: (M+H) calculated 428.17, observed 428.25.

A portion of the above intermediate material (4.3 g, 10.1 mmoles) was dried by evaporation two times with dry acetonitrile (100 mL portions) and then dissolved in 100 mL of acetonitrile. The solution was cooled to 0° C. (ice/water bath). Trimethylsilyl iodide (4.04 g, 20.1 mmoles) was added dropwise and the solution was allowed to gradually warm to ambient temperature. At 6 hours and 30 hours, another equivalent of trimethylsilyl iodide (2.10 g, 10.5 mmoles) was added, and the reaction is stirred overnight after each addition. The reaction was stopped by the addition of MeOH and the volume was reduced under vacuum to 10 mL. The solution was diluted with ethyl acetate and washed with saturated aqueous sodium thiosulfate. The aqueous phase was back extracted three times with ethyl acetate, and the combined organic extracts were washed with saturated aqueous sodium bicarbonate. The organic layer was further washed with saturated aqueous sodium chloride and dried by passage through anhydrous sodium sulfate. Evaporation to dryness gave the product, which was used without any purification. The yield was 1.56 g (38%). ESMS: (M+TEA-H) calculated 515.27, observed 515.36.

2'-O-(2-(4,4'-Dimethoxytrityl)Oxyethyl)Cytidine
(13)

Crude compound 12 (1.56 g, 3.8 mmoles) was dissolved in 20 mL pyridine and treated with DMTr-Cl (1.90 g, 5.7 mmoles). After 1 hour the reaction was quenched with MeOH (10 mL) and evaporated to dryness. The crude material was treated with 50 mL of 0.1 M anhydrous potassium carbonate in MeOH for 16 hours and purified by flash chromatography on 100 mL of silica gel using a gradient of MeOH in DCM (0% to 5% (v/v)) containing 0.1% (v/v) TEA. Product fractions were pooled and evaporated to afford the product as a colorless oil. The yield was 1.96 g (87%).

$N^4$-Acetyl-2'-O-(2-(4,4'-Dimethoxytrityl)Oxyethyl)-3',5'-O-(Tetraisopropyldisiloxane-1,3-Diyl)Cytidine
(14)

TIPDS-Cl$_2$ (1.58 g, 5.0 mmoles) was added to a solution of compound 13 (1.96 g, 3.30 mmoles) in 33 mL of pyridine at room temperature. After 3 hours, acetic anhydride (0.67 g, 6.6 mmoles) was added to the reaction mixture. The reaction was quenched with MeOH (5 mL) after 20 minutes and evaporated to dryness. The crude material was partitioned between DCM and saturated aqueous sodium bicarbonate and the aqueous phase was back extracted two times with DCM. The combined organic phases dried by passage over anhydrous sodium sulfate and evaporated to dryness. The resulting paste was purified by flash chromatography on 100 mL of silica gel using a gradient of MeOH in DCM (0% to 2% (v/v)) containing 0.1% (v/v) TEA. Product fractions were pooled and evaporated to afford the product as a colorless oil. The yield was 2.18 g (76%).

N-Acetyl-2'-O-[2-(4-Oxopentanoate)Oxyethyl)]Cytidine (5)

To a solution of the above compound 14 (2.18 g, 2.5 mmoles) in 20 mL of 2-propanol was added ammonium cerium(IV) nitrate (0.62 g, 1.13 mmoles). After 1.5 hours, more ammonium cerium(IV) nitrate (0.30 g, 0.55 mmoles) was added and the reaction was stirred for an additional 2 hours. The reaction was diluted with MeOH and concentrated to dryness. The resulting orange paste was purified by flash chromatography on 70 mL of silica gel using a gradient of MeOH in DCM (0% to 3% (v/v)). Product fractions were pooled and evaporated to afford a colorless oil. The yield was 1.07 g (75%). ESMS: (M+Na) calculated 594.26, observed 594.39.

To a solution of DCC (0.58 g, 2.81 mmoles) in 25 mL of DCM was added levulinic acid (0.65 g, 5.62 mmoles). After 30 minutes the white precipitate was filtered away and the clear solution was evaporated to dryness. To this flask was added the material from the above reaction (1.07 g, 1.87 mmoles) in DCM (30 mL), TEA (0.76 g, 7.48 mmoles), and DMAP (0.05 g, 0.37 mmoles). After 3 hours the mixture was diluted with DCM and washed with saturated aqueous sodium bicarbonate. The organic layer was further washed with saturated aqueous sodium chloride and dried by passage through anhydrous sodium sulfate Evaporation to dryness gave a light brown paste, which was used without further purification.

To a solution of TEMED (1.4 mL, 9.35 mmoles) in 10 mL of acetonitrile at 0° C. (ice/water bath) was added dropwise 48% aqueous hydrofluoric acid (0.24 mL, 6.55 mmoles). This solution was allowed to stir for 5 minutes and was then added to the product of the above reaction (1.87 mmoles) in a separate flask. The reaction was stirred for 3 hours and concentrated to dryness. The crude material was purified by flash chromatography on 50 mL of silica gel using a gradient of MeOH in ethyl acetate (0 to 4% (v/v)) containing 0.1% (v/v) TEMED. Evaporation to dryness afforded a colorless glass. The yield was 0.74 g (92%). $^1$H NMR δ (CDCl$_3$, 400 MHz) 9.64 (s, 1H), 8.47 (d, J=7.6 Hz, 1 H), 7.42 (d, J=7.6 Hz, 1 H), 5.82 (s, 1 H), 4.36-4.29 (m, 3 H), 4.23-4.19 (m, 1H), 4.12-4.06 (m, 3H), 2.78-2.75 (m, 2 H), 2.58-2.55 (m, 2 H), 2.24 (s, 3 H), 2.21 (s, 3 H).

$N^4$-Acetyl-5'-O-[Benzhydryloxy-Bis(Trimethylsilyloxy)Silyl]-2'-O-[2-(4-Oxopentanoate)Oxyethyl)]
Cytidine (16)

To a solution of compound 15 (0.92 g, 2.16 mmoles) in 15 mL of DCM was added diisopropylamine (0.22 g, 2.16 mmoles) and the reaction mixture was cooled to 0° C. (ice/water bath). In a separate flask, BZH-Cl (1.40 g, 3.24 mmoles) was dissolved in 10 mL of DCM. Diisopropylamine (0.39 g, 3.90 mmoles) was added dropwise to the silylating solution over 1 minute. The silylating solution was then added dropwise to the starting material at 0° C. until TLC analysis showed complete consumption of starting material. The reaction was stopped by the addition of 5 mL of MeOH and evaporated to dryness. The crude material was purified by flash chromatography on 100 mL of silica gel using a gradient of ethyl acetate and acetone in hexanes (2:0:8 to 2:2:6 (v/v/v)) containing 0.1% (v/v) TEA. Product fractions were pooled and evaporated to afford a colorless oil. The yield was 1.32 g (75%). $^1$H NMR δ (CDCl$_3$, 400 MHz) 9.26 (s, 1 H), 8.37 (d, J=7.6 Hz, 1 H), 7.37-7.18 (m, 11 H), 5.94 (s, 1 H), 5.89 (s, 1 H), 4.34-4.28 (m, 3 H), 4.06-4.03 (m, 2 H), 3.97-3.92 (m, 2 H), 3.88-3.85 (m, 1 H), 3.82-3.80 (m, 1 H), 2.83 (d, J=9.6 Hz, 1 H), 2.78-2.75 (m, 2 H), 2.60-2.57 (m, 2 H), 2.26 (s, 3 H), 2.18 (s, 3 H), 0.09 (s, 9 H), 0.08 (s, 9 H); ESMS: (M+Na) calculated 838.28, observed 838.17.

$N^4$-Acetyl-5'-O-[Benzhydryloxy-Bis(Trimethylsilyloxy)Silyl]-2'-O-[2-(4-Oxopentanoate)Oxyethyl)]
Cytidine 3'-O-(N,N,-Diisopropylamino)Methoxy Phosphoramidite (17)

Bis(diisopropylamino)methoxyphosphine (0.64 g, 2.43 mmoles) was dissolved in 8 mL of DCM and a 0.45 M solution of 5-ethylthio-1H-tetrazole in anhydrous acetonitrile (1.8 mL, 0.81 mmoles) was added. Diisopropylamine (0.16 g, 1.62 mmoles) was then added and the phosphine solution was allowed to stir for 5 minutes at ambient temperature. In a separate flask compound 16 (1.32 g, 1.62 mmoles) and diisopropylamine (0.16 g, 1.62 mmoles) were dissolved in 8 mL of DCM. The activated phosphine solution was added into the nucleoside solution and the reaction was stirred at room temperature. After 16 hours the reaction was quenched with 5 mL of absolute ethanol and concentrated to dryness. The resulting paste was purified by flash chromatography on 60 mL of silica gel using a mixture of DCM in hexanes (5:95 (v/v)) containing 1% (v/v) TEA followed by acetone in hexanes (3:7 (v/v))

containing 0.1% (v/v) TEA. Product fractions were pooled and evaporated to afford a colorless oil. The yield was 1.29 g (82%).

Synthesis of 5'-O-[Benzhydryloxy-Bis(Trimethylsilyloxy)Silyl]-21-O-[2-(4-Oxopentanoate)Oxyethyl] Uridine 3'-O-(N,N,-Diisopropylamino)Methoxy Phosphoramidite (2) (FIG. 5) [Prophetic]

The method for the synthesis of this compound would be similar to that for the adenosine compound described above and is illustrated in FIG. 5. The preparation of the starting material for the synthesis, $N^3$-benzyloxymethyl-2'-O-(methoxycarbonylmethylene)uridine, is given in the following reference: Dobson, N., McDowell, D. G., French, D. J., Brown, L. J., Mellor, J. M., and Brawn, T. (2003) "Synthesis of HyBeacons and dual-labeled probes containing 2'-fluorescent groups for use in genetic analysis" *Chem. Commun.*, 1234-1235.

Synthesis of $N^2$-Isobutyryl-5'-O-[Benzhydryloxy-Bis(Trimethylsilyloxy)Silyl]-2'-O-[2-(4-Oxopentanoate)Oxyethyl)]Guanosine 3'-O-(N,N,-Diisopropylamino) Methoxy Phosphoramidite (29) (FIG. 6) [Prophetic]

The method for the synthesis of this compound would be similar to that for the cytidine compound described above and is illustrated in FIG. 6. The preparation of the starting material for the synthesis, 2'-O-(methoxyethyl)guanosine, is given in the following reference: Wen, K., Chow, S., Sanghvi, Y. S., and Theodorakis, E. A. (2002) "Synthesis of 2'-O-Methoxyethylguanosine Using a Novel Silicon-Based Protecting Group" *J. Org. Chem.* 67, 7887-7889.

Figure 7:
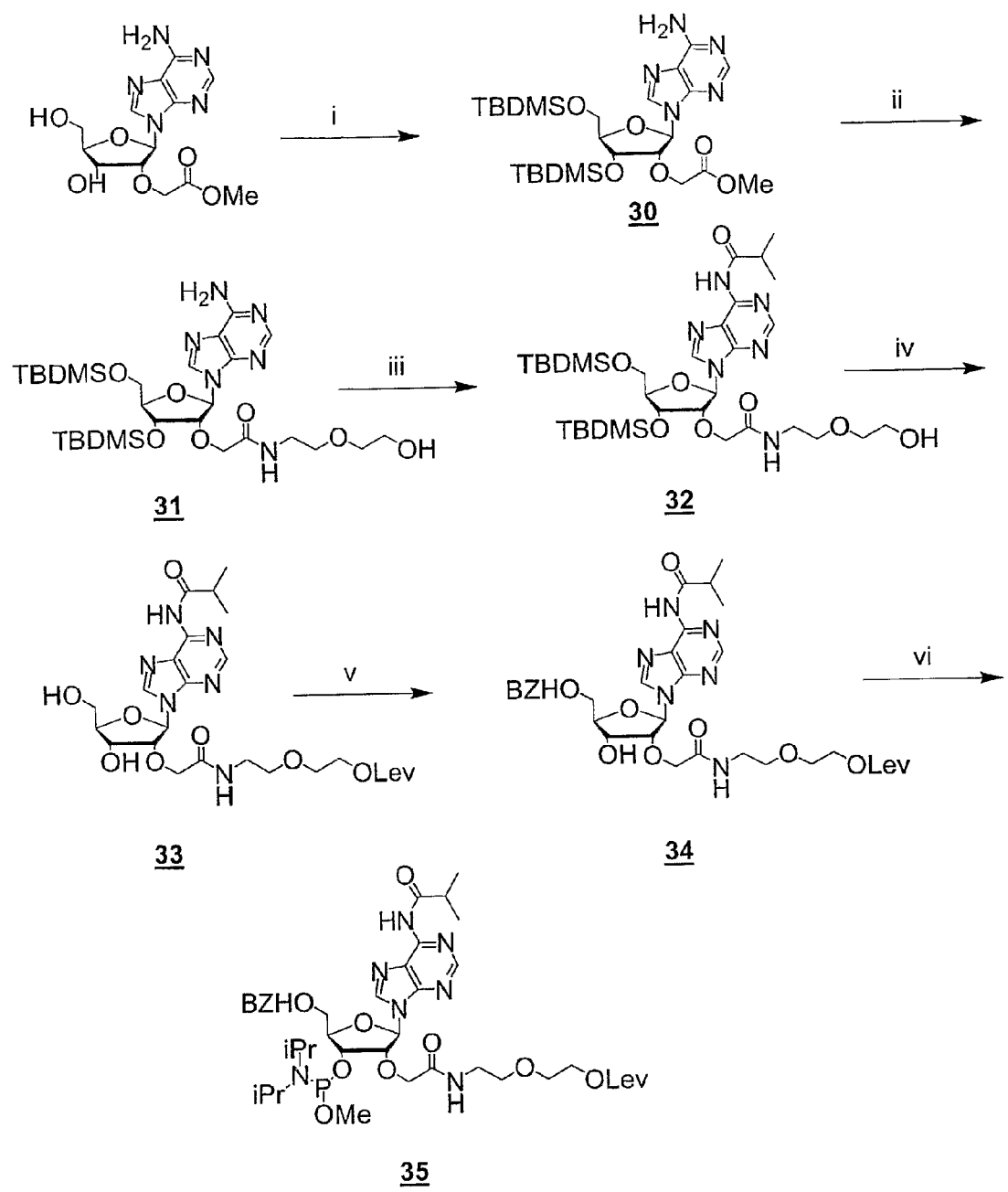
FIG. 7 is a schematic representation of the synthesis of one embodiment of a protected nucleoside phosphoramidite having a linker protected by a levulinyl moiety. In this case the nucleotide base is adenine, and the linker is attached to the 2'-hydroxyl by an ether linkage. The reaction conditions include: (i) TBDMS-Cl/imidazole/DMF; (ii) a) lithium hydroxide/THF/MeOH/water; BOP, HOBT, 2-(2-aminoethoxy)ethanol; (iii) a) TMS-Cl/pyridine; b) isobutyryl chloride; c) ammonium hydroxide; (iv) a) levulinic anhydride/TEA/DMAP/DCM; b) TBAF/THF; (v) BZH-Cl/diisopropylamine/DCM; (vi) bis(diisopropylamino)methoxy phosphine/5-ethylthio-1H-tetrazole/diisopropylamine/DCM.
Figure 8:
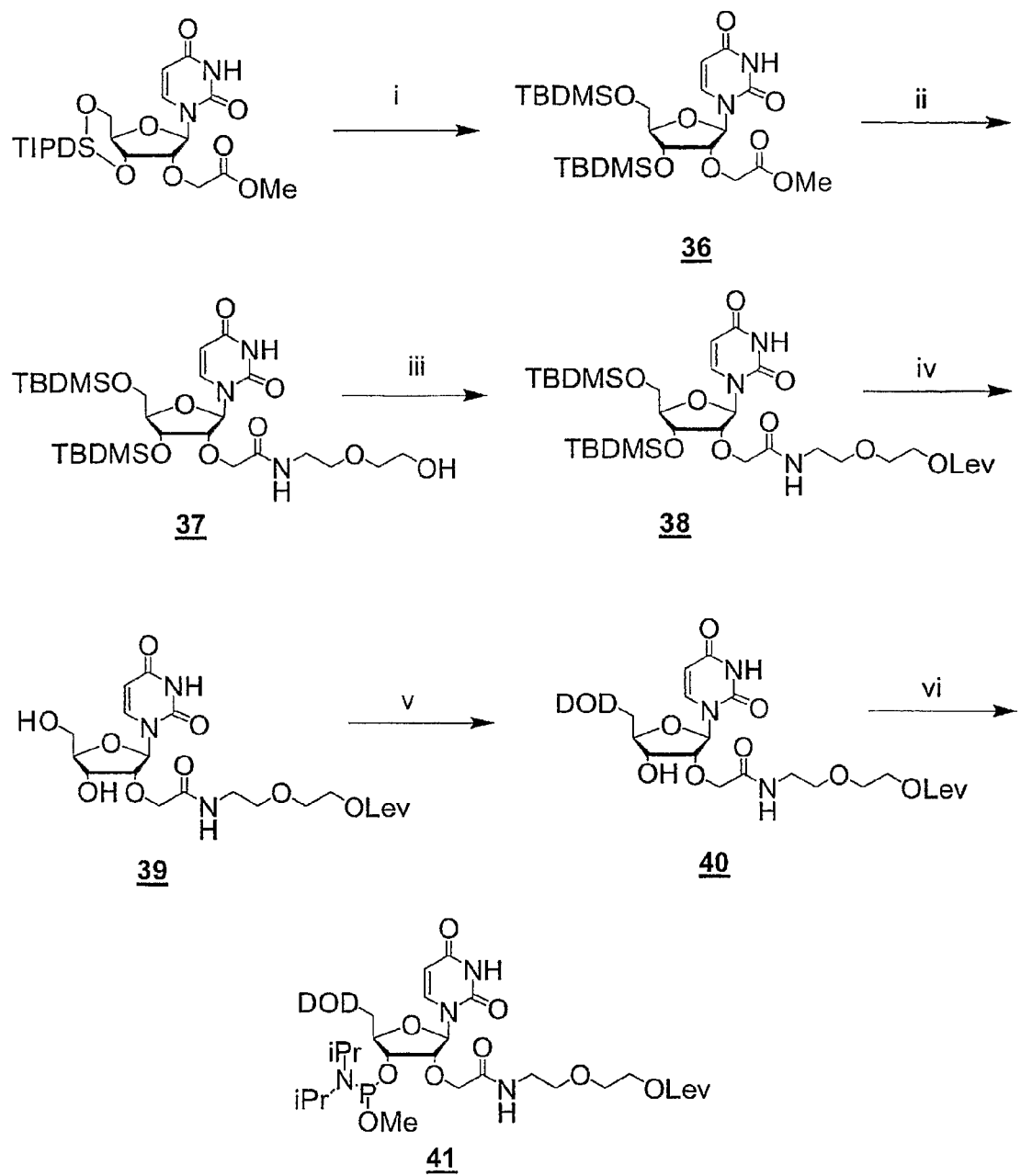
FIG. 8 is a schematic representation of the synthesis of one embodiment of a protected nucleoside phosphoramidite having a linker protected by a levulinyl moiety. In this case the nucleotide base is uracil, and the linker is attached to the 2'-hydroxyl by an ether linkage. The reaction conditions include: (i) a) TEMED/hydrofluoric acid/acetonitrile; b) TBDMS-Cl/imidazole/DMF; (ii) a) lithium hydroxide/THF/MeOH/water; b) BOP, HOBT, 2-(2-aminoethoxy)ethanol; (iii) levulinic anhydride/TEA/DMAP/DCM; (iv) TBAF/THF; (v) DOD-Cl/diisopropylamine/DCM; (vi) bis(diisopropylamino)methoxy phosphine/5-ethylthio-1H-tetrazole/diisopropylamine/DCM.
Figure 9:
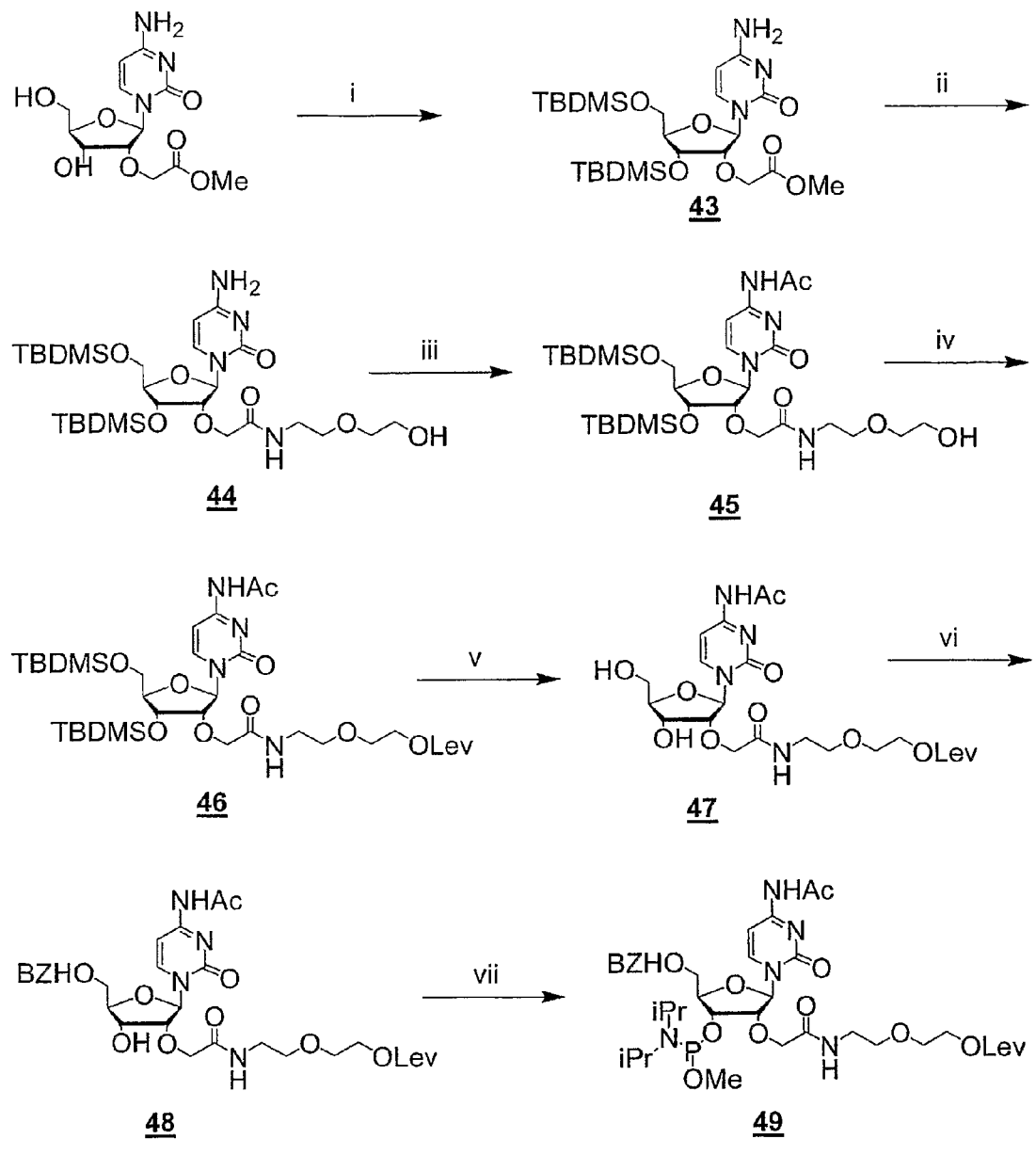
FIG. 9 is a schematic representation of the synthesis of one embodiment of a protected nucleoside phosphoramidite having a linker protected by a levulinyl moiety. In this case the nucleotide base is cytosine, and the linker is attached to the 2'-hydroxyl by an ether linkage. The reaction conditions include: (i) TBDMS-Cl/imidazole/DMW; (ii) a) lithium hydroxide/THF/MeOH/water; b) BOP/HOBt/2-(2-aminoethoxy)ethanol; (iii) a) TMS-Cl/pyridine; b) acetic anhydride; c) ammonium hydroxide; (iv) levulinic anhydride/TEA/DMAP/DCM; (v) TBAF/THF; (vi) BZH-Cl/diisopropylamine/DCM; (vii) bis(diisopropylamino)methoxy phosphine/5-ethylthio-1H-tetrazole/diispropylamine/DCM.
Figure 10:
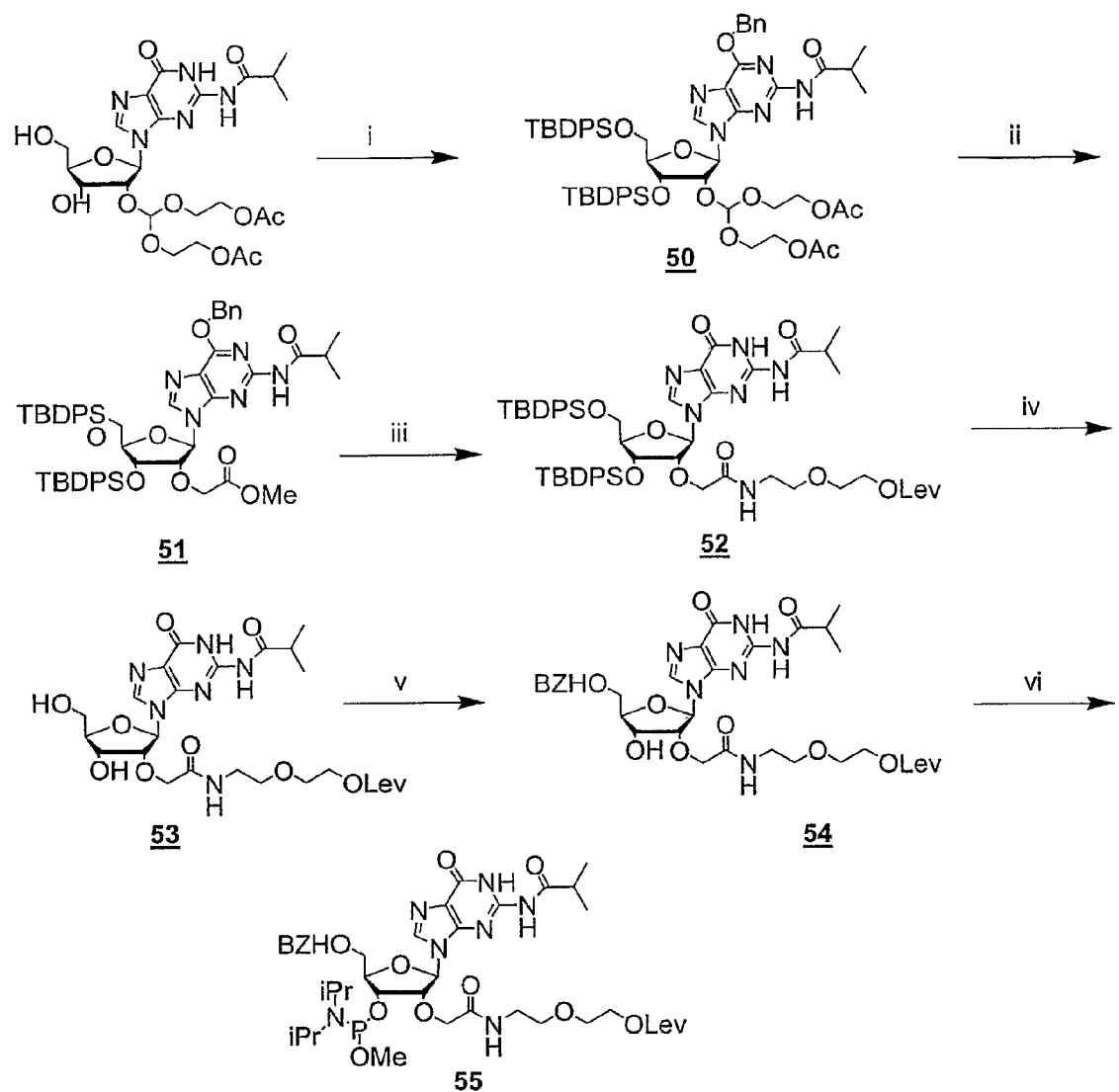
FIG. 10 is a schematic representation of the synthesis of one embodiment of a protected nucleoside phosphoramidite having a linker protected by a levulinyl moiety. In this case the nucleotide base is guanine, and the linker is attached to the 2'-hydroxyl by an ether linkage. The reaction conditions include: (i) a) TBDPS-Cl/imidazole/DMF; b) diisopropyldiazo dicarboxylate/benzyl alcohol/triphenylphosphine/dioxane; (ii) a) potassium carbonate/MeOH; b) 300 mM acetic acid-TEMED (pH 3.8)/acetonitrile; c) sodium hydride/methyl bromoacetate/DMF; (iii) a) 10% Pd/C/H$_2$/MeOH; b) lithium hydroxide/THF/MeOH/water; c) BOP/HOBt/2-(2-aminoethoxy)ethanol; d) levulinic anhydride/TEA/DMAP/DCM; (iv) TBAF/THF; (v) BZH-Cl/diisopropylamine/DCM; (vi) bis(diisopropylamino)methoxy phosphine/5-ethylthio-1H-tetrazole/diisopropylamine/DCM.
Figure 10:
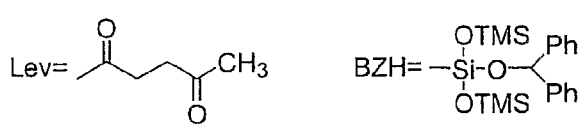

Synthesis of $N^6$-Isobutyryl-5'-O-[Benzhydryloxy-Bis(Trimethylsilyloxy)Silyl]-2'-O-[2-(2-(4-Oxopentanoate)Oxyethoxy)Ethylaminocarbonyl Methylene] Adenosine 3'-O-(N,N,-Diisopropylamino)Methoxy Phosphoramidite (35) (FIG. 7)

3',5'-O-Bis(T-Butyldimethylsilyl)-2'-O-(Methoxycarbonylmethylene)Adenosine (30)

TBDMS-Cl (8.61 g, 57.1 mmoles) and imidazole (6.20 g, 91.4 mmoles) were added to a solution of 2'-O-(methoxycarbonylmethyl)adenosine (7.75 g, 22.8 mmoles) in 115 mL of pyridine. After stirring for 24 hours, the reaction was stopped with 30 mL of MeOH and evaporated to dryness. The resulting paste was dissolved in ethyl acetate and washed with 5% (w/v) hydrochloric acid, water and saturated aqueous sodium bicarbonate. The solution was dried by passage over anhydrous sodium sulfate and concentrated to dryness to leave a white solid that was used without further purification. The yield was 11.72 g (91%). $^1$H NMR δ (CDCl$_3$, 400 MHz) 8.33 (s, 1 H), 8.19 (s, 1 H), 6.21 (d, J=4.0 Hz, 1 H), 6.08 (b, 2 H), 4.58-4.56 (m, 2 H), 4.44 (q, J=17.6 Hz, 2 H), 4.154.13 (m, 1 H), 3.95 (dd, J=3.2 Hz, J=11.4 Hz, 1 H), 3.76 (dd, J=3.2 Hz, J=11.4 Hz, 1 H), 3.63 (s, 3 H), 0.92 (s, 9 H), 0.90 (s, 9 H), 0.13 (s, 3 H), 0.13 (s, 3 H), 0.08 (s, 3 H), 0.07 (s, 3 H); ESMS: (M+H) calculated 568.30, observed 568.42.

3',5'-O-Bis(T-Butyldimethylsilyl)-2'-O-[2-(2-Hydroxyethoxy)Ethylaminocarbonyl Methylene]Adenosine (31)

To a solution of compound 30 (11.72 g, 20.7 mmoles) in 80 mL of THF and 80 mL of MeOH was added a solution of lithium hydroxide (2.5 g, 103.6 mmoles) in 40 mL of water. After 20 minutes the reaction was neutralized by the addition of 2.4 M hydrochloric acid (43.2 mL, 103.6 mmoles) and solution was reduced to 50 mL by evaporation under reduced pressure. The solution was diluted with ethyl acetate and washed with water. The aqueous portion was back-extracted three times with ethyl acetate and the combined organic extracts were washed with saturated aqueous sodium chloride. The organic solution was dried by passage over anhydrous sodium sulfate and evaporated to dryness to afford a white foam that was used without further purification. The yield was 10.12 g (88%).

Activation of the intermediate acid (10.12 g, 18.3 mmoles) was accomplished by dissolving the above compound in 180 mL of DMF and stirring with BOP (9.70 g, 21.9 mmoles), HOBt (3.50 g, 25.6 mmoles), and TEA (3.70 g, 36.6 mmoles). After 30 min 2-(2-aminoethoxy)ethanol (4.82 g, 45.8 mmoles) was added and the reaction was allowed to proceed for 1 hour. The solvent was removed under reduced pressure and the resulting oil was dissolved in ethyl acetate and washed with water. The aqueous phase was back-extracted twice with ethyl acetate and the combined organic extracts were washed aqueous sodium chloride. The organic solution was dried by passage over anhydrous sodium sulfate and evaporated to dryness to afford a dark oil that was purified by flash chromatography on 400 mL of silica gel using a gradient of MeOH in DCM (2% to 5% (v/v)). Product fractions were pooled and evaporated to give a thick syrup that was contaminated by a small amount of residual HOBt. The yield was 8.71 g (74%). ESMS: (M+H) calculated 641.35, observed 641.36.

$N^6$-Isobutyryl-3',5'-O-Bis(T-Butyldimethylsilyl)-2'-O-[2-(2-Hydroxyethoxy) Ethylaminocarbonyl Methylene]Adenosine (32)

Compound 31 (8.99 g, 14.02 mmoles) was dissolved in 70 mL of pyridine, cooled to 0° C. (ice/water bath) and TMS-Cl (2.28 g, 21.0 mmoles) as added. After 1 hour isobutyryl chloride (2.99 g, 28.04 mmoles) was added and the solution was warmed to ambient temperature. The mixture was stirred overnight, then cooled to 0° C. (ice/water bath) and water (30 mL) was added. After stirring for 20 minutes, concentrated ammonium hydroxide (30 mL) was added and stirred for an additional 30 minutes. The solution was then evaporated to dryness and purified by flash chromatography to afford a white foam. The yield was 5.01 g (50%). $^1$H NMR δ (CDCl$_3$, 400 MHz) 8.75 (s, 1 H), 8.34 (s, 1 H), 7.26 (m, 1 H), 6.26 (d, J=5.2 Hz, 1 H), 4.50-4.48 (m, 1 H), 4.32-4.29 (m, 1 H), 4.19-4.12 (m, 2 H), 4.00-3.95 (m, 2 H), 3.80-3.77 (m, 1 H), 3.75-3.72 (m, 2 H), 3.57-3.55 (m, 3 H), 3.49-3.46 (m, 2 H), 3.36-3.29 (m, 1 H), 3.17-3.13 (m, 1 H), 1.30 (d, J=6.8 Hz, 6 H), 0.93 (s, 9 H), 0.90 (s, 9 H), 0.12 (s, 3 H), 0.11 (s, 3 H), 0.11 (s, 3 H), 0.11 (s, 3 H); ESMS: (M+H) calculated 711.39, observed 711.41.

$N^6$-Isobutyryl-2'-O-[2-(2-(4-Oxopentanoate)Oxyethoxy)Ethylaminocarbonyl-Methylene]Adenosine (33)

Levulinic acid (2.45 g, 21.1 mmoles) was added to a solution of DCC (2.20 g, 10.6 mmoles) in 60 mL of DCM. After 30 minutes the white precipitate was filtered away and the clear solution was evaporated to dryness. To this flask was added compound 32 (5.01 g, 7.05 mmoles) in 70 mL of DCM, TEA (2.85 g, 28.2 mmoles), and DMAP (0.02 g, 0.16 mmoles). After 3 hours the mixture was diluted with DCM and washed with saturated aqueous sodium bicarbonate. The organic phase was further washed with aqueous sodium chloride and dried by passage over anhydrous sodium sulfate. Evaporation of the solvent afforded a light yellow paste that was used without further purification. The yield was 6.04 g.

TBAF (5.6 g, 17.63 mmoles) was added to the above material in 70 mL of THF. After 16 hours the solution is evaporated to dryness and purified by flash chromatography on 250 mL of silica gel using a gradient of MeOH in 100% DCM (0% to 4% (v/v)). Product fractions were pooled and evaporated to afford a white foam. The yield is 2.4 g (59%). $^1$H NMR δ (CDCl$_3$, 400 MHz) 8.84 (s, 1 H), 8.68 (s, 1 H), 8.16 (s, 1 H), 7.18-7.16 (m, 1 H), 6.06 (d, J=7.6 Hz, 1 H), 4.71 (dd, J=4.0 Hz, J=7.6 Hz, 1 H), 4.50-4.48 (m, 1 H), 4.39-4.38 (m, 1 H), 4.27-4.24 (m, 2 H), 4.23-4.19 (m, 1 H), 3.99-3.91 (mn, 2 H), 3.78-3.75 (m, 1 H), 3.64-3.61 (m, 2 H), 3.55-3.39 (m, 4 H), 3.23-3.18 (m, 1 H), 2.77-2.74 (m, 2 H), 2.58-2.55 (m, 2 H), 2.16 (s, 3 H), 1.30 (d, J=6.8 Hz, 6 H); ESMS: (M+H) calculated 581.26, observed 581.27.

N$^6$-Isobutyryl-5'-O-[Benzyhydryloxy-Bis(Trimethylsilyloxy)Silyl]-2'-O-[2-(2-(4-Oxopentanoate)Oxyethyoxy)Ethylaminocarbonylmethylene]Adenosine (34)

To a solution of compound 33 (2.40 g, 4.13 mmoles) in 30 mL of DCM was added diisopropylamine (0.42 g, 4.13 mmoles), and the solution was cooled to 0° C. (ice/water bath). In a separate flask, BZH-Cl (2.64 g, 6.20 mmoles) was diluted in 20 mL of DCM. Diisopropylamine (0.75 g, 7.44 mmoles) was added dropwise to the silylating solution over 1 minute. The silylating solution was then added dropwise to the solution of compound 33 at 0° C. until TLC analysis showed complete consumption of starting material. The reaction was stopped by the addition of 10 mL of MeOH and evaporated to dryness. The crude material was purified by flash chromatography on 150 mL of silica gel using a gradient of ethyl acetate and acetone in hexanes (2:2:6 to 3:2:5 (v/v/v)) containing 0.1% (v/v) TEA. Product fractions were pooled and evaporated to afford a colorless oil. The yield was 3.39 g (85%). $^1$H NMR δ (CDCl$_3$, 400 MHz) 8.70 (s, 1 H), 8.43 (s, 1 H), 8.32 (m, 1 H), 7.35-7.18 (m, 10 H), 6.23 (d, J=4.0 Hz, 1 H), 5.93 (s, 1 H), 4.28-4.24 (m, 3 H), 4.18-4.13 (m, 2 H), 4.05-4.01 (m, 1 H), 3.97-3.92 (mn, 1 H), 3.82-3.79 (m, 1 H), 3.64-3.62 (m, 2 H), 3.56-3.53 (m, 2 H), 3.44-3.30 (m, 2 H), 2.76-2.73 (m, 2 H), 2.59-2.57 (m, 2 H), 2.16 (s, 3 H), 1.31 (d, J=6.0 Hz, 6 H), 0.08 (s, 18 H); ESMS: (M+H) calculated 991.37, observed 991.54.

N$^6$-Isobutyryl-5'-O-[Benzyhydryloxy-Bis(Trimethylsilyloxy)Silyl]-2'-O-[2-(2-(4-Oxopentanoate)Oxyethoxy)Ethylaminocarbonylmethylene]Adenosine (3'-O-(N,N,-Diisopropylamino)Methoxy Phosphoramidite (35)

Bis(diisopropylamino)methoxy phosphine (1.40 g, 5.25 mmoles) was dissolved in 10 mL of DCM and a 0.45 M solution of 5-ethylthio-1H-tetrazole in anhydrous acetonitrile (3.9 mL, 1.75 mmoles) was added. Diisopropylamine (0.35 g, 3.50 mmoles) was then added and the phosphine solution was allowed to stir for 5 minutes at ambient temperature. In a separate flask compound 34 (3.39 g, 3.50 mmoles) and diisopropylamine (0.35 g, 3.50 mmoles) were dissolved in 25 mL of DCM. The activated phosphine solution was added into the nucleoside solution and the reaction was stirred at room temperature. After 16 hours the reaction was quenched with 10 mL of absolute ethanol and concentrated to dryness. The resulting paste was purified by flash chromatography on 150 mL of silica gel using a mixture of DCM in hexanes (5:95 (v/v)) containing 1% (v/v) TEA followed by acetone in hexanes (3:7 (v/v)) containing 0. 1% (v/v) TEA. Product fractions were pooled and evaporated to afford a colorless oil. The yield was 3.63 g (92%).

5'-O-[Cyclododecyloxy-Bis(Trimethylsilyloxy)Silyl]-2'-O-[2-(2-(4-Oxopentanoate)Oxyethoxy)Ethylaminocarbonyl Methylene]Uridine 3'-O-(N,N,-Diisopropylamino)Methoxy Phosphoramidite (41)

The method for the synthesis of this compound was similar to that for the adenosine compound described above and is illustrated in FIG. 8. The preparation of the starting material for the synthesis, 2'-O-(methoxycarbonylmethylene)-3',5'-O-(tetraisopropyldisiloxane-1,3-diyl)uridine, is given in the following reference: Dobson, N., McDowell, D. G., French, D. J., Brown, L. J., Mellor, J. M., and Brown, T. (2003) "Synthesis of HyBeacons and dual-labeled probes containing 2'-fluorescent groups for use in genetic analysis" *Chem. Commun.*, 1234-1235.

3',5'-O-Bis(T-Butyldimethylsilyl)-2'-O-[Methoxycarbony-Methylene]Uridine (36)

To a solution of TEMED (6.1 mL, 40.8 mmoles) in 75 mL of acetonitrile at 0° C. (ice/water bath) was added dropwise 48% aqueous hydrofluoric acid (1.03 mL, 28.6 mmoles). This solution was allowed to stir for 5 minutes and added to 2'-O-(methoxycarbonylmethylene)-3',5'-O-(tetraisopropyldisiloxane-1,3-diyl)uridine (4.56 g, 8.16 mmoles) in a separate flask. The reaction was stirred for 2 hours and concentrated to dryness. The crude material was purified by flash chromatography on 150 mL silica gel using a gradient of MeOH in ethyl acetate (0 to 3% (v/v)) containing 0.1% TEMED (v/v). Product fractions were pooled and evaporated to afford 2'-O-(methoxycarbonyl methylene) uridine as a white foam after drying in vacuo. The yield was 2.23 g (86%). $^1$H NMR δ (DMSO, 400 MHz) 11.35 (s, 1 H), 7.87 (d, J=8.0 Hz, 1 H), 5.91 (d, J=5.5 Hz, 1 H), 5.66 (d, J=8.5 Hz, 1 H), 5.19 (d, J=5.0 Hz, 1 H), 5.12 (t, J=5.0 Hz, 1 H), 4.25 (dd, J=16.5 Hz, J=51.8 Hz, 2 H), 4.13-4.10 (m, 1 H), 4.07-4.05 (m, 1 H), 3.89-3.87 (m, 1 H), 3.62 (s, 3 H), 3.61-3.58 (m, 1 H), 3.56-3.52 (m, 1 H); ESMS: (M+Na) calculated 339.08, observed 339.15.

To the above material (2.23 g, 7.1 mmoles) in 70 mL of DMF was added TBDMS-Cl (2.66 g, 17.6 mmoles), imidazole (1.92 g, 28.2 mmoles), and DMAP (0.09 g, 0.7 mmoles). The reaction was stirred for 4 hours and quenched with 10 mL of MeOH. The solution was evaporated to dryness and partitioned between ethyl acetate and 5% (v/v) aqueous hydrochloric acid. The aqueous phase was extracted twice with ethyl acetate and the combined organics were further washed with water, and then saturated aqueous sodium bicarbonate. The organic phase was dried by passage over anhydrous sodium sulfate and evaporated to dryness to leave a white foam that was used without additional purification. The yield was 3.15 g (83%). $^1$H NMR δ (CDCl$_3$, 500 MHz) 8.62 (b, 1 H), 8.00 (d, J=8.0 Hz, 1 H), 6.01 (d, J=3.0 Hz, 1 H), 5.68 (d, J=8.0 Hz, 1 H), 4.X3 (dd, J=16.5 Hz, J=39.0 Hz, 2 H), 4.25 (dd, J=5.0 Hz, J=11.5 Hz, 1 H), 4.12-4.10 (m, 1 H), 4.01 (dd, J=2.5 Hz, J=14.0 Hz, 1 H), 3.94 (dd, J=3.0 Hz, J=4.5 Hz, 1 H), 3.76 (dd, f=1.5 Hz,-J=12.0 Hz, 1 H), 3.73 (s, 3 H), 0.93 (s, 9 H), 0.90 (s, 9 H), 0.13 (s, 3 H), 0.13 (s, 3 H), 0.12 (s, 3 H), 0.11 (s, 3 H); ESMS: (M+Na) calculated 567.25, observed 567.38.

3',5'-O-Bis(T-Butyldimethylsilyl)-2'-O-[2-(2-Hydroxyethoxy)Ethylamino-Carbonyl Methylene]Uridine (37)

To a solution of 36 (3.17 g, 5.8 mmoles) in 15 mL of THF and 15 mL of MeOH was added a suspension of lithium hydroxide (0.42 g, 17.5 mmoles) in 7.5 mL of water. After 20 min the reaction was neutralized by the addition of 2.4 M hydrochloric acid (7.3 mL, 17.5 mmoles) and solution was reduced to 10 mL by evaporation under reduced pressure. The solution was diluted with ethyl acetate and washed with water. The aqueous portion was back-extracted three times with ethyl acetate and the combined organic extracts were washed with saturated aqueous sodium chloride. The organic solution was dried by passage over anhydrous sodium sulfate and evaporated to dryness to leave afford a white foam that was used without further purification. The yield was 2.85 g (92%).

Activation of the intermediate acid (2.85 g, 5.4 mmoles) was accomplished by dissolving the above compound in 50 mL of DMF and stirring with BOP (2.85 g, 6.4 mmoles), HOBt (1.02 g, 7.6 mmoles), and TEA (1.09 g, 10.8 mmoles). After 30 minutes 2-(2-aminoethoxy)ethanol (1.42 g, 13.5 mmoles) was added and the reaction was allowed to proceed for 4.5 hours. The solvent was removed under reduced pressure and the resulting oil was dissolved in ethyl acetate and washed with water. The aqueous phase was back-extracted twice with ethyl acetate and the combined organic extracts were washed with aqueous saturated sodium chloride. The organic solution was dried by passage over anhydrous sodium sulfate and evaporated to afford a light-yellow oil that was purified by flash chromatography on 200 mL silica gel using a gradient of MeOH in DCM (0.5% to 5% (v/v)). Product fractions were pooled and evaporated to give a colorless oil that was contaminated by a small amount of residual HOBt. The yield was 3.17 g (95%). $^1$H NMR δ (CDCl$_3$, 500 MHz) 9.39 (b, 1H), 7.89 (d, J=8.0 Hz, 1 H), 7.18 (m, 1 H), 6.05 (d, J=4.0 Hz, 1 H), 5.69 (d, J=8.0 Hz, 1 H), 4.25-4.22 (m, 1 H), 4.16 (d, J=15.0 Hz, 1 H), 4.104.08 M, 1 H), 4.05 (d, J=15.0 Hz, 1 H), 3.97 (dd, J=2.0 Hz, J=11.5 Hz, 1 H), 3.81-3.79 (m, 1 H), 3.76-3.73 (m, 3 H), 3.62-3.57 (m, 5 H), 3.43-3.38 (m, 1 H), 0.92 (s, (H), 0.90 (s, 9 H), 0.12 (s, 3 H), 0.11 (s, 3 H), 0.10 (s, 3 H), 0.09 (s, 3 H); ESMS: (M+Na) calculated 640.31, observed 640.32.

3',5'-O-Bis(T-Butyldimethylsilyl)-2'-O-[2-(4-Oxo-pentanoate)Oxyethoxy)Ethylaminocarbonyl-Methylene]Uridine (38)

Levulinic acid (1.78 g, 15.3 mmoles) was added to a solution of DCC (1.59 g, 7.7 mmoles) in 75 mL of DCM. After 30 minutes the white precipitate was filtered away and the clear solution was evaporated to dryness. To this flask was added compound 37 (3.17 g, 5.1 mmoles) in 20 mL of DCM, TEA (2.06 g, 20.4 mmoles), and DMAP (0.06 g, 0.5 mmoles). After 30 minutes the mixture was diluted with DCM and washed with saturated aqueous sodium bicarbonate. The organic phase was further washed with aqueous sodium chloride and dried by passage over anhydrous sodium sulfate. Evaporation of the solvent afforded a paste that was purified by flash chromatography on 200 mL silica gel using a gradient of MeOH in DCM (0% to 3% (v/v)). Product fractions were pooled and evaporated to give a colorless oil. The yield was 3.0 g (82%). $^1$H NMR δ (CDCl$_3$, 500 MHz) 8.98 (b, 1 H), 7.95 (d, J=8.0 Hz, 1 H), 6.99 (m, 1 H), 5.98 (d, J=2.5 Hz, 1 H), 5.67 (d, J=8.0 Hz, 1 H), 4.28-4.25 (m, 3 H), 4.24-4.18 (m, 2 H), 4.08-4.02 (m, 1 H), 4.01 (dd, J=2.5 Hz, J=12.0 Hz, 1 H), 3.81-3.79 (m, 1 H), 3.77-3.75 (m, 1 H), 3.66-3.64 (mn, 2 H), 3.58-3.53 (m, 3 H), 2.78-2.75 (m, 2 H), 2.62-2.61 (m, 2 H), 2.20 (s, 3 H), 0.92 (s, 9 H), Q.90 (s, 9 H), 0.12 (s, 3 H), 0.11 (s, 3 H), 0.11 (s, 3 H), 0.09 (s, 3 H).

2'-O-[2-(4-Oxopentanoate)Oxyethoxy)Ethylaminocarbonyl-Methylene]Uridine (39)

TBAF (3.30 g, 10.46 mmoles) was added to 38 (3.0 g, 4,18 mmoles) in 42 mL of THF. After 16 hours the solution was evaporated to dryness and purified by flash chromatography on 80 mL of silica gel using a gradient of MeOH in DCM (3% to 7% (v/v)). Product fractions were pooled and evaporated to afford a white foam. The yield was 1.42 g (69%). $^1$H NMR δ (CDCl$_3$, 500 MHz) 9.68 (b, 1 H), 8.03 (d, J=8.0 Hz, 1 H), 7.77-7.74 (m, 1 H), 5.80 (d, J=2.5 Hz, 1 H), 5.70 (d, J=8.0 Hz, 1 H), 4.37-4.34 (m, 2 H), 4.27-4.22 (m, 3 H), 4.13-4.11 (m, 1 H), 4.054.04 (m, 1 H), 4.00-3.98 (m, 1 H), 3.88-3.85 (m, 1 H), 3.66-3.65 (m, 2 H), 3.59-3.56 (m, 2 H), 3.49-3.45 (m, 2 H), 2.78 (t, J=6.0 Hz, 2 H), 2.58 (s, J=6.0 Hz, 2 H), 2.20 (s, 3 H); ESMS: (M+Na) calculated 510.17, observed 510.20.

5'-O-[Cyclododecyloxy-Bis(Trimethysilyloxy)Silyl]-2'-O-[2-(2-(4-Oxopentanoate)Oxyethoxy)Ethyleaminocarbonylmethylene]Uridine (40)

To a solution of compound 39 (1.42 g, 2.91 mmoles) in 20 mL of DCM was added diisopropylamine (0.29 g, 2.91 mmoles), and the solution was cooled to 0° C. (ice/water bath). In a separate flask, DOD-Cl (1.90 g, 4.40 mmoles) was diluted in 10 mL of DCM. Diisopropylamine (0.54 g, 5.30 mmoles) was added dropwise to the silylating solution over 1 minute. The silylating solution was then added dropwise to the solution of compound 39 at 0° C. until TLC analysis showed complete consumption of starting material. The reaction was stopped by the addition of 10 mL of MeOH and evaporated to dryness. The crude material was purified by flash chromatography on 100 mL of silica gel using a gradient of ethyl acetate and acetone in hexanes (0:2:8 to 6:2:2 (v/v/v)) containing 0.1% (v/v) TEA. Product fractions were pooled and evaporated to afford a colorless oil. The yield was 1.67 g (65%). $^1$H NMR δ (CDCl$_3$, 500 MHz) 8.59(b, 1 H), 7.97 (d, J=8.5 Hz, 1 H), 6.00 (d, J=3.5 Hz, 1 H), 5.68 (d, J=17.5 Hz, 1 H), 4.294.22 (m, 5 H), 4.17-4.13 (m, 1 H), 4.12-4.09 (m, 1 H), 4.07-3.99 (m, 3 H), 3.93-3.90 (mn, 2 H), 3.67-3.66 (m, 2 H), 3.59-3.52 (m, 3 H), 3.47-3.42 (m, 1 H), 2.79 (t, J=6.5 Hz, 2 H), 2.62 (t, J=6.5 Hz, 2 H), 2.21 (s, 1 H), 1.47-1.29 (m, 23 H), 0.15 (s, 18 H); ESMS: (M+H) calculated 876.42, observed 876.42.

5'-O-[Cyclododecyloxy-Bis(Trimethysilyloxy)Silyl]-2'-O-[2-(2-(4-Oxopentanoate)Oxyethoxy)Ethylaminocarbonyl Methylene]Uridine 3'-O-(N,N,-Diisopropylamino)Methoxy Phosphoramidite (41)

Bis(diisopropylamino)methoxy phosphine (0.75 g, 2.85 mmoles) was dissolved in 10 mL of DCM and a 0.5 M solution of 5-ethylthio-1H-tetrazole in anhydrous acetonitrile (1.90 mL, 0.95 mmoles) was added. Diisopropylamine (0.19 g, 1.90 mmoles) was then added and the phosphine solution was allowed to stir for 5 minutes at ambient temperature.

In a separate flask compound 40 (1.67 g, 1.90 mmoles) and diisopropylamine (0.19 g, 1.90 mmoles) were dissolved in 10 mL of DCM. The activated phosphine solution was added into the nucleoside solution and the reaction was stirred at room temperature. After 16 hours the reaction was quenched with 10 mL of absolute ethanol and concentrated to dryness. The resulting paste was purified by flash chromatography on 60 mL of silica gel using a mixture of DCM in hexanes (5:95 (v/v)) containing 1% (v/v) TEA followed by acetone in hexanes (3:7 (v/v)) containing 0.1% (v/v) TEA. Product fractions were pooled and evaporated to afford a colorless oil. The yield was 1.76 g (92%).

N⁴-Acetyl-5'-O-[Benzhydryloxy-Bis(Trimethylsilyloxy)Silyl]-2'-O-[2-(2-(4-Oxopentanoate)Oxyethoxy)Ethylaminocarbonyl Methylene]Cytidine 3'-O-(N,N,-Diisopropylamino)Methoxy Phosphoramidite (49) [Prophetic]

The method for the synthesis of this compound would be similar to that for the adenosine compound described above and is illustrated in FIG. 9. The starting material for the synthesis, 2'-O-(methoxycarbonylmethylene)cytidine, is prepared in a manner similar to that of the uridine compound above.

N²-Isobutyryl-5'-O-[Benzhydryloxy-Bis(Trimethylsilyloxy)Silyl]-2'-O-[2-(2-(4-Oxopentanoate)Oxyethoxy)Ethylaminocarbonyl Methylene]Guanosine 3'-O-(N,N,-Diisopropylamino)Methoxy Phosphoramidite (55) [Prophetic]

The method for the synthesis of this compound would be similar to that for the adenosine compound described above and is illustrated in FIG. 10. The preparation of the starting material for the synthesis, N²-isobutyryl-2'-O-bis(acetoxyethyl)orthoformate guanosine, is given in the following reference: Scaringe, S. A., Kitchen, D., Kaiser, R., and Marshall, W. M., (2004) "Preparation of 5'-Silyl-2'-Orthoester Ribonucleosides for the Use in Oligoribonucleotide Synthesis" *Current Protocols in Nucleic Acid Chemistry* vol. 1. (Beaucage, S. L., ed; New York: John Wiley & Sons, Inc.), 2.10.11-15.

Example 3

Synthesis of a Nucleoside Phosphoramidite with a Linker Protected by a Levulinyl Moiety at the 2'-Position of the Ribosyl Moiety—Method 2

A nucleoside phosphoramidite comprising a linker protected by a levulinyl moiety, or derivative thereof, attached to the 2'-position of the ribosyl moiety was prepared in the manner described below.

In general, a ribonucleoside was first prepared having its 3' and 5' hydroxyl groups and nitrogenous base protected. The 2'-hydroxyl was then modified with a reactive carbonyl derivative, and an amino alcohol linker was subsequently attached, forming a 2'-carbamate. The linker was modified with a levulinyl moiety. The protecting groups on the 3'- and 5'-hydroxyl groups were removed and the 5'-hydroxyl was protected in a manner appropriate to the polynucleotide synthesis chemistry to be employed (for example, with DMTr-Cl in pyridine or with benzhydryloxy-bis(trimethylsilyloxy) chlorosilane in dichloromethane and diisopropylamine). Finally, the free 3'-hydroxyl was reacted with an appropriate phosphine (for example, bis(diisopropylamino)methoxy phosphine in the presence of a tetrazole catalyst) to produce the desired nucleoside phosphoramidite. The methods are illustrated in FIGS. 11, 12, 13 and 14, and detailed below for the particular examples given.

Figure 11:
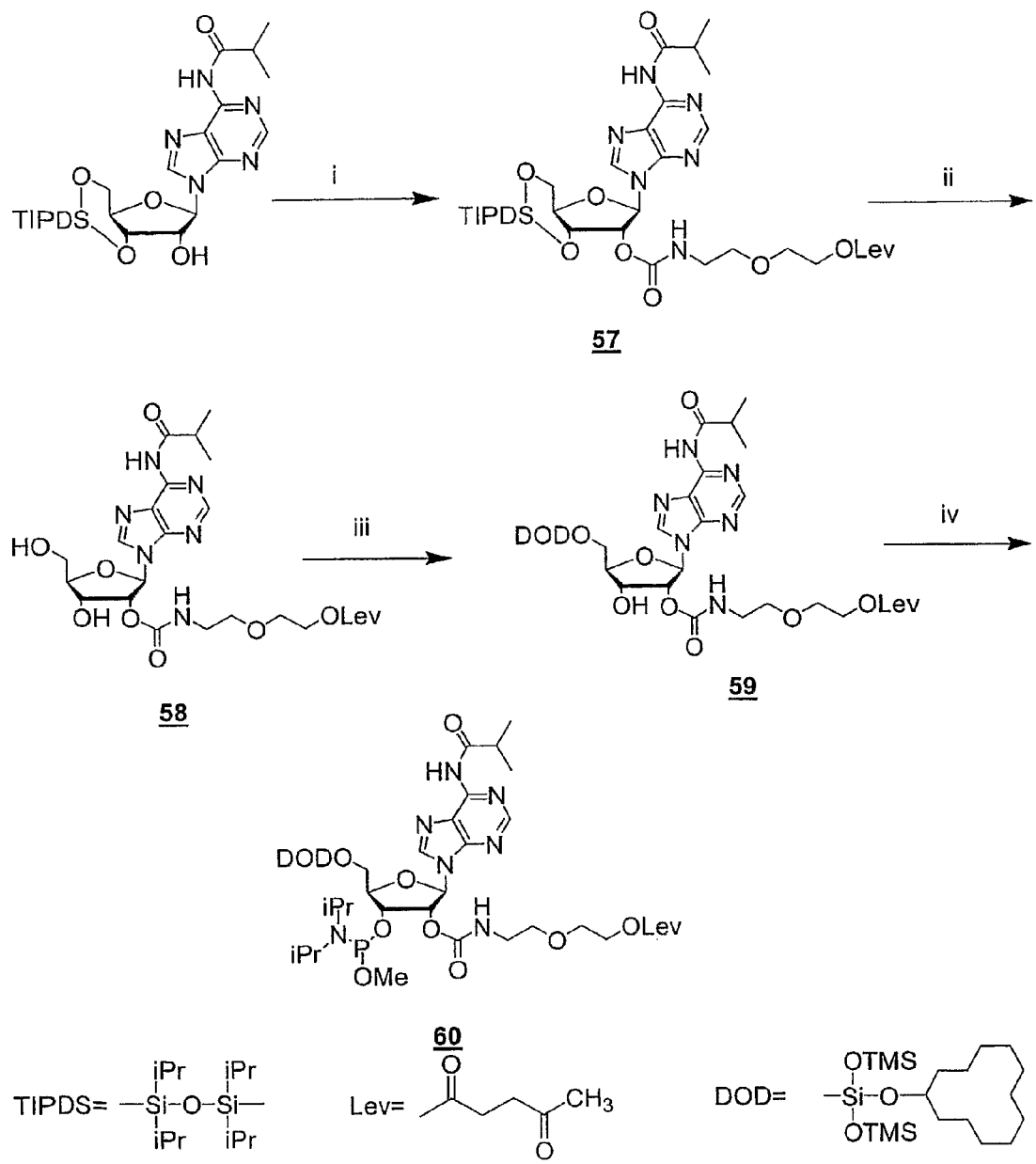
FIG. 11 is a schematic representation of the synthesis of one embodiment of a protected nucleoside phosphoramidite having a linker protected by a levulinyl moiety. In this case the nucleotide base is adenine, and the linker is attached to the 2'-hydroxyl by a carbamate linkage. The reaction conditions include: (i) a) CDI/DCM; b) 2-(2-aminoethoxy)ethanol; c) levulinic anhydride/TEA/DMAP/DCM; (ii) TEMED/hydrofluoric acid/acetonitrile; (iii) DOD-Cl/diisopropylamine/DCM; (iv) bis(diisopropylamino)methoxy phosphine/5-ethylthio-1H-tetrazole/diisopropylamine/DCM.

Synthesis of N⁶-Isobutyryl-5'-O-[Cyclododecyloxy-Bis(Trimethylsilyloxy)Silyl]-2'-O-[2-(2-(4-Oxopentanoate)Oxyethoxy)Ethylamino Carbonyl]Adenosine 3'-O-(N,N,-Diisopropylamino)Methoxy Phosphoramidite (60) (FIG. 11)

N⁶-isobutyryl-2'-O-[2-(2-(4-Oxopentanoate)Oxyethoxy)Ethylaminocarbonyl]-3', 5'-O-(Tetraisopropyldisiloxane-1,3-Dilyl)Adenosine (57)

CDI (3.9 g, 23.9 mmoles) was added to a solution of N⁶-isobutyryl-3',5'-O-(tetraisopropyldisiloxane-1,3-diyl)adenosine (13.2 g, 22.8 mmoles) in 220 mL of DCM. After 3 hours the reaction was cooled to 0° C. (ice/water bath) and 2-(2-aminoethoxy)ethanol (3.6 g, 34.2 mmoles) was added. The reaction was stopped after 3 hours. The crude reaction mixture was purified by flash chromatography on 300 mL of silica gel using a mixture of DCM in ethyl acetate (2:3 (v/v)) then a mixture of MeOH in ethyl acetate (2% (v/v)). Product fractions were pooled and evaporated to afford a white foam. The product was contaminated with small amounts of imidazole and 2-(2-aminoethoxy)ethanol. The yield was 15.3 g (94%). ¹H NMR δ (CDCl₃, 400 MHz) 8.64 (s, 1 H), 8.16 (s, 1 H), 6.05 (s, 1 H), 5.63 (d, J=5.2 Hz, 1 H, 5.59-5.58 (m, 1 H), 5.08-5.06 (m, 1 H), 4.194.15 (m, 1 H), 4.06-3.99 (m, 2 H), 3.78-3.76 (m, 2 H), 3.60-3.55 (m, 4 H), 3.50-3.30 M, 2 H), 3.17-3.12 (m, 1 H), 1.29 (d, J=6.8 Hz, 6 H), 1.13-0.95 (m, 28 H); ESMS: (M+H) calculated 711.35, observed 711.31.

Levulinic acid (10.0 g, 86.2 mmoles) was added to a solution of DCC (8.9 g, 43.1 mmoles) in 400 mL of DCM. After 30 minutes the white precipitate was filtered away and the clear solution was evaporated to dryness. To this flask was added the material from the above reaction (15.3 g, 21.5 mmoles) dissolved in 430 mL of DCM, TEA (8.7 g, 86.0 mmoles), and DMAP (0.5 g, 4.3 mmoles). After stirring for 16 hours, another 2 equivalents of levulinic anhydride (prepared in the same fashion as above) were added to the reaction in 200 mL of DCM. The reaction was complete after 1 hour. The mixture was then diluted with DCM and washed with saturated aqueous sodium bicarbonate. The organic solution was further washed with saturated aqueous sodium chloride and dried by passage over anhydrous sodium sulfate. Evaporation of the solvent afforded a white foam that was used without further purification. The yield was 22.0 g.

N⁶-Isobutyryl-2'-O-[2-(2-(4-Oxopentanoate)Oxyethoxy)Ethylaminocarbonyl]Adenosine (58)

48% aqueous hydrofluoric acid (3.4 mL, 95.2 mmoles) was added dropwise to a solution of TEMED (20.4 mL, 136.0 mmol) in 55 1mL of acetonitrile at 0° C. (ice/water bath). This solution was allowed to stir for 10 minutes and was then added to compound 57 (22.0 g, 27.2 mmoles) in a separate flask. The reaction was stirred for 3 hours and concentrated to dryness. The crude material was purified by flash chromatography on 400 mL of silica gel using a gradient of MeOH in ethyl acetate (0% to 15% (v/v)) containing 0.1% (v/v) TEMED. Product fractions were pooled and evaporated to afford a white foam. The yield was 7.2 g (56%). ¹H NMR δ (CDCl₃, 500 MHz) 8.91 (b, 1 H), 8.67 (s, 1 H), 8.18 (s, 1 H), 6.11 (d, J=6.5 Hz, 1 H), 5.82 (m, 1 H), 5.77 (m, 1 H), 4.75-4.73 (m, 1 H), 4.32 (m, 1 H), 4.32-4.23 (m, 1 H), 4.18-4.14 (m, 1 H), 4.00-3.97 (m, 1 H), 3.82-3.80 (m, 1 H), 3.64-3.57 (m, 2 H), 3.48-3.42 (m, 2 H), 3.29-3.17 (m, 3 H), 2.79-2.73 (m, 2 H), 2.60-2.56 (m, 2 H), 2.21 (s, 3 H), 1.28 (d, J=5.5 Hz, 6 H); ESMS: (M+H) calculated 567.24, observed 567.21.

N⁶-Isobutyryl-5'-O-[Cyclododecyloxy-Bis(Trimethylsilyloxy)Silyl]-2'-O-[2-(2-(4-Oxopentanoate)Oxyethoxy)Ethylaminocarbonyl]Adenosine (59)

Diisopropylamine (0.27 g, 2.65 mmoles) was added to a solution of compound 58 (1.50 g, 2.65 mmoles) in 10.6 mL of DCM, and the solution was cooled to 0° C. (ice/water bath). In a separate flask, DOD-Cl (2.25 g, 5.30 mmoles) was diluted in 5 mL of DCM. Diisopropylamine (0.64 g, 6.36 mmoles) was added dropwise to the silylating solution over 1 minute. The silylating solution was added dropwise to the starting material at 0° C. until TLC analysis showed complete consumption of starting material. The reaction was stopped by the addition of 5 mL of MeOH and evaporated to dryness. The crude material was purified by flash chromatography on 60 mL of silica gel using a gradient of ethyl acetate and acetone in hexanes (0:2:8 to 4:2:4 (v/v/v)) containing 0.1% (v/v) TEA to afford a white foam. The yield was 1.90 g (75%). $^1$H NMR δ (CDCl$_3$, 500 MHz) 8.72 (s, 1 H), 8.48 (s, 1 H), 6.32 (d, J=5.0 Hz, 1 H), 5.69 (m, 1 H), 5.54 (m, 1 H), 4.67 (m, 1 H), 4.37-4.32 (mn, 1 H), 4.24-4.21 (mn, 1 H), 4.18-4.13 (mn, 1 H), 4.06-4.02 (m, 2 H), 3.94-3.92 (m, 1 H), 3.66-3.58 (m, 2 H), 3.54-3.46 (m, 2 H), 3.36-3.30 (m, 1 H), 3.27-3.20 (m, 1 H), 2.81-2.79 (m, 2 H), 2.64-2.60 (m, 2 H), 2.24 (s, 3 H), 1.67-1.64 (m, 2 H), 1.46-1.28 (m, 28 H), 0.13 (s, 18 H); ESMS: (M+H) calculated 955.47, observed 955.44.

N$^6$-Isobutyryl-5'-O-[Cyclododecyloxy-Bis(Trimethylsilyloxy)Silyl]-2'-O-[2-(2-(4-Oxopentanoate)Oxyethoxy)Ethylamino Carbonyl]Adenosine 3'-O-(N,N,-Diisopropylamino)Methoxy Phosphoramidite (60)

Bis(diisopropylamino)methoxy phosphine (0.78 g, 2.98 mmoles) was dissolved in 4 mL of DCM and a 0.45 M solution of 5-ethylthio-1H-tetrazole in anhydrous acetonitrile (2.2 mL, 1.0 mmoles) was added. Diisopropylamine (0.20 g, 1.99 mmoles) was then added and the phosphine solution was allowed to stir for 5 minutes at ambient temperature. In a separate flask compound 59 (1.90 g, 1.99 mmoles) and diisopropylamine (0.20 g, 1.99 mmoles) were dissolved in 4 mL of DCM. The activated phosphine solution was added into the nucleoside solution and the reaction was stirred at room temperature. After 16 hours the reaction was quenched with 5 mL of absolute ethanol and concentrated to dryness. The resulting paste was purified by flash chromatography on 100 mL of silica gel using a mixture of DCM in hexanes (5:95 (v/v)) containing 1% (v/v) TEA followed by acetone in hexanes (3:7 (v/v)) containing 0.1% (v/v) TEA. Product fractions were pooled and evaporated to afford a colorless oil. The yield was 2.00 g (90%).

Figure 12:
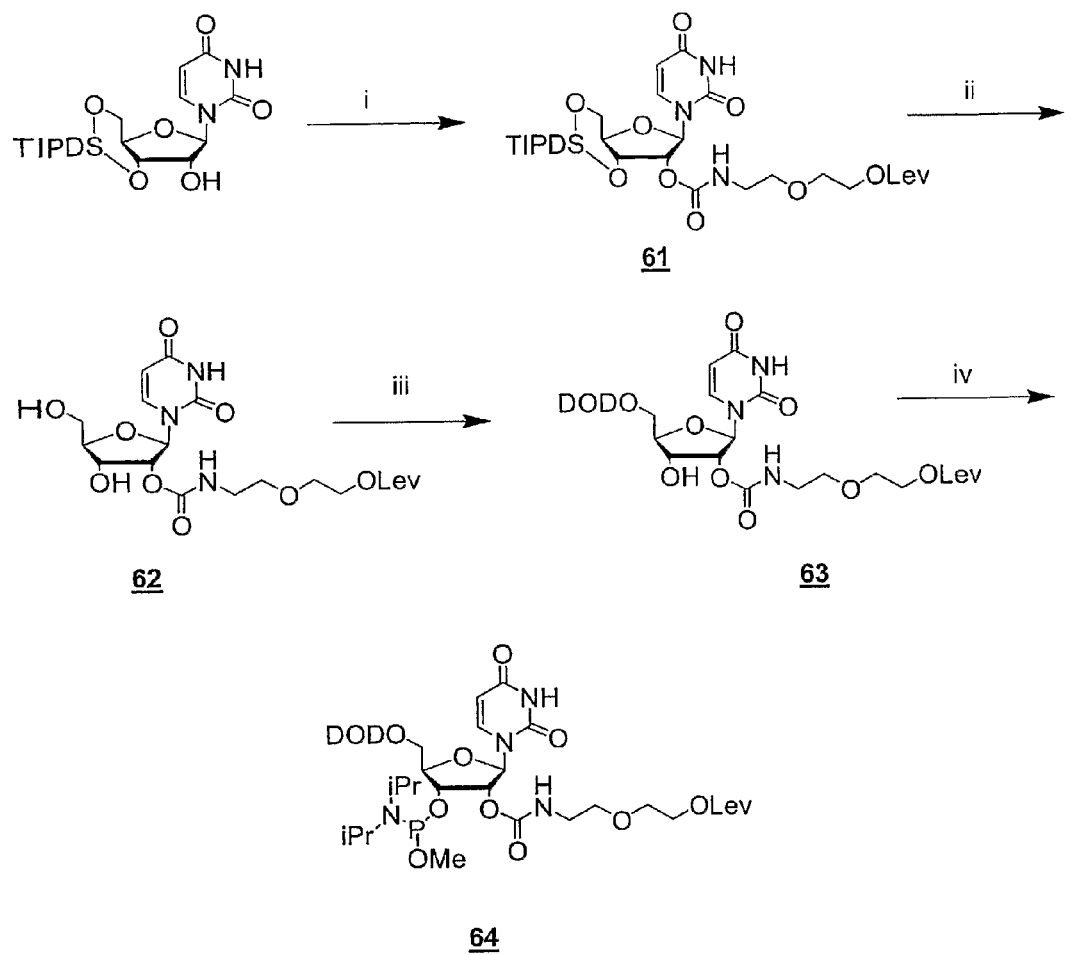
FIG. 12 is a schematic representation of the synthesis of one embodiment of a protected nucleoside phosphoramidite having a linker protected by a levulinyl moiety. In this case the nucleotide base is uracil, and the linker is. attached to the 2'-hydroxyl by a carbamate linkage. The reaction conditions include: (i) a) CDI/DCM; b) 2-(2-aminoethoxy)ethanol; c) levulinic anhydride/TEA/DMAP/DCM; (ii) TEMED/hydrofluoric acid/acetonitrile; (iii) DOD-Cl/diisoproplylamine/DCM; (iv) bis(diisopropylamino)methoxy phosphine/5-ethylthio-1H-tetrazole/diisopropylamine/DCM.
Figure 12:
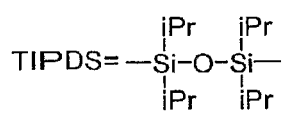
Figure 12:
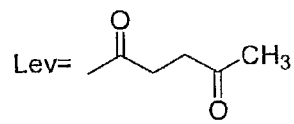
Figure 12:
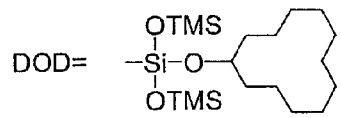

Synthesis of 5'-O-[Cyclododecyloxy-Bis(Trimethylsilyloxy)Silyl]-2'-O-[2-(2-(4-Oxopentanoate)Oxyethoxy)Ethylaminocarbonyl]Uridine 3'-O-(N,N,-Diisopropylamino)Methoxy Phosphoramidite (64) (FIG. 12)

2'-O-[2-(2-(4-Oxopentanoate)Oxyethoxy)Ethylaminocarbonyl]-3',5'-O-(Tetraisopropyldisiloxane-1,3-Diyl)Uridine (61)

CDI (3.9 g, 23.8 mmoles) was added to a solution of 3',5'-O-(tetraisopropyldisiloxane-1,3-diyl)uridine (11.1 g, 22.7 mmoles) in 200 mL of DCM. After 2 hours the reaction was cooled to 0° C. (ice/water bath) and 2-(2-aminoethoxy) ethanol (7.2 g, 68.1 mmoles) was added. The reaction was stopped after 2 hours and partitioned between ethyl acetate and water. The organic phase was dried by passage over anhydrous sodium sulfate and evaporated to dryness. The crude material was purified by flash chromatography on 300 mL silica gel using a gradient of ethyl acetate in hexane (50% (v/v) to 100%). Product fractions were pooled and evaporated to afford a white foam. The yield was 11.2 g (80%). $^1$H NMR δ (CDCl$_3$, 400 MHz) 9.38 (b, 1 H), 7.66 (d, J=8.4 Hz, 1 H), 5.85 (s, 1 H), 5.76 (b, 1 H), 5.69 (d, J=8.0 Hz, 1 H), 5.25 (d, J=4.8 Hz, 1 H), 4.38-4.33 (m, 1 H), 4.21-4.18 (m, 1 H), 3.99-3.96 (m, 2 H), 3.76-3.72 (m, 2 H), 3.61-3.51 (m, 4 H), 3.39 (m, 2 H), 2.78 (b, 1 H), 1.10-0.94 (m, 28 H); ESMS: (M+Na) calculated 640.27, observed 640.22.

Levulinic acid (5.46 g, 47.1 mmoles) was added to a solution of DCC (4.90 g, 23.5 mmoles) in 100 mL of DCM. After 30 minutes the white precipitate was filtered away and the clear solution was evaporated to dryness. To this flask was added the product of the above reaction (11.2 g, 18.1 mmoles) dissolved in 150 mL of DCM, TEA (7.3 g, 72.4 mmoles), and DMAP (0.22 g, 1.81 mmoles). After 30 minutes the mixture was diluted with DCM and washed with saturated aqueous sodium bicarbonate. The organic phase was further washed with saturated aqueous sodium chloride and dried by passage through anhydrous sodium sulfate. Evaporation of the solvent afforded a white foam that was purified by flash chromatography on 300 mL of silica gel using a gradient of ethyl acetate in hexanes (50% to 75% (v/v)). Product fractions were pooled and evaporated to afford a white foam. The yield was 12.2 g (95%). $^1$H NMR δ (CDCl$_3$, 400 MHz) 8.96 (b, 1 H), 7.65 (d, J=8.0 Hz, 1 H), 5.82 (s, 1 H), 5.68 (dd, J=2.0 Hz, J=8.0 Hz, 1 H), 5.44 (m, 1 H), 5.26 (d, J=4.8 Hz, 1 H), 4.38-4.34 (m, 1 H), 4.24-4.22 (m, 2 H), 4.19-4.16 (m, 1 H), 4.00-3.96 (m, 2 H), 3.66-3.63 (m, 2 H), 3.56-3.52 (m, 2 H), 3.40-3.37 (m, 2 H), 2.78-2.75 (m, 2 H), 2.62-2.59 (m, 2 H), 2.19 (s, 3 H), 1.08-0.94 (m, 28 H); ESMS: (M+Na) calculated 738.31, observed 738.26.

2'-O-[2-(2-(4-Oxopentanoate)Oxyethoxy)Ethylaminocarbonyl]Uridine (62)

48% aqueous hydrofluoric acid (2.1 mL, 59.3 mmoles) was added dropwise to a solution of TEMED (12.7 mL, 84.8 mmoles) in 85 mL of acetonitrile at 0° C. (ice/water bath). This solution was allowed to stir for 5 minutes and was then added to compound 61 (12.1 g, 17.0 mmoles) in a separate flask. The reaction was stirred for 3 hours and concentrated to dryness. The crude material was purified by flash chromatography on 300 mL of silica gel using a gradient of MeOH in ethyl acetate (0% to 5% (v/v)) containing 0.1% (v/v) TEMED. Product fractions were pooled and evaporated to afford a white foam. The yield was 7.2 g (90%). $^1$H NMR δ (CDCl$_3$, 400 MHz) 9.82 (b, 1 H), 7.75 (d, J=7.6 Hz, 1 H), 6.22 (b, 1 H), 5.91 (s, 1 H), 5.75 (d, J=8.0 Hz, 1 H), 5.21 (m, 1 H), 4.45 (m, 1 H), 4.27-4.17 (m, 2 H), 4.11-4.06 (m, 1 H), 3.94-3.90 (m, 1 H), 3.84-3.78 (m, 1 H), 3.67-3.55 (m, 6 H), 3.33 (m, 2 H), 2.79-2.76 (m, 2 H), 2.60-2.57 (m, 2 H), 2.20 (s, 3 H); ESMS: (M+Na) calculated 496.15, observed 496.13.

5'-O-[Cyclododecyloxy-Bis(Trimethylsilyloxy)Silyl]-2'-O-[2-(2-(4-Oxopentanoate)Oxyethoxy)Ethylaminocarbonyl]Uridine (63)

Diisopropylamine (0.34 g, 3.40 mmoles) was added to a solution compound 62 (1.60 g, 3.40 mmoles) in 20 mL of DCM and the solution was cooled to 0° C. (ice/water bath). In a separate flask, DOD-Cl (2.20 g, 5.10 mmoles) was diluted in 15 mL of DCM. Diisopropylamine (0.62 g, 6.10 mmoles) was added dropwise to the silylating solution over 1 minute. The silylating solution was added dropwise to the starting material at 0° C. until TLC analysis showed complete consumption of starting material. The reaction was stopped by the addition of 10 mL of MeOH and evaporated to dryness. The crude material was purified by flash chromatography on 150 mL of silica gel using a gradient of ethyl acetate and acetone in hexanes (0:2:8 to 2:2:6 (v/v/v)) containing 0.1%(v/v) TEA to afford a white foam. The yield was 2.31 g (79%). $^1$H NMR δ (CDCl$_3$, 500 mHz) 9.82 (b, 1 H), 7.84 (d, J=8.5 Hz, 1 H), 6.17 (d, J=6.0 Hz, 1 H), 5.79 (b, 1 H), 5.70 (d, J=8.0 Hz, 1 H), 5.07 (m, 1 H), 4.44-4.42 (m, 1 H), 4.38-4.32 (m, 1 H), 4.19-4.15 (m, 1 H), 4.12 (m, 1 H), 4.06-3.99 (m, 1 H), 3.98-3.96 (m, 1 H), 3.88-3.86 (m, 1 H), 3.70-3.61 (m, 2 H), 3.69-3.53 (m, 2 H), 3.42-3.30 (m, 2 H), 2.82-2.79 (m, 2 H), 2.63-2.60 (m, 2 H), 2.23 (s, 3 H), 1.68-1.63 (m, 2 H), 1,46-1.29 (m, 22 H), 0.14 (s, 18 H); ESMS: (M+Na) calculated 884.38, observed 884.34.

5'-O-[Cyclododecyloxy-Bis(Trimethylsilyloxy)Silyl]-2'-O-[2-(2-(4-Oxopentanoate)Oxyethoxy)Ethylaminocarbonyl]Uridine 3'-O-(N,N,-Diisopropylamino)Methoxy Phosphoramidite (64)

Bis(diisopropylamino)methoxy phosphine (0.98 g, 3.75 mmoles) was dissolved in 10 mL of DCM and a 0.45 M solution of 5-ethylthio-1H-tetrazole in anhydrous acetonitrile (2.8 mL, 1.25 mmoles) was added. Diisopropyl amine (0.25 g, 2.50 mmoles) was then added and the phosphine solution was allowed to stir for 5 minutes at ambient temperature. In a separate flask compound 63 (2.16 g, 2.50 mmoles) and diisopropylamine (0.25 g, 2.50 mmoles) were dissolved in 10 mL of DCM. The activated phosphine solution was added into the nucleoside solution and the reaction was stirred at room temperature After 16 hours the reaction was quenched with 5 mL of absolute ethanol and concentrated to dryness. The resulting paste was purified by flash chromatography on 50 mL of silica gel using a mixture of DCM in hexanes (5:95 (v/v)) containing 1% (v/v) TEA followed by acetone in hexanes (2:8 (v/v)) containing 0.1%o (v/v) TEA. Product fractions were pooled and evaporated to afford a colorless oil. The yield was 2.41 g (94%).

Figure 13:
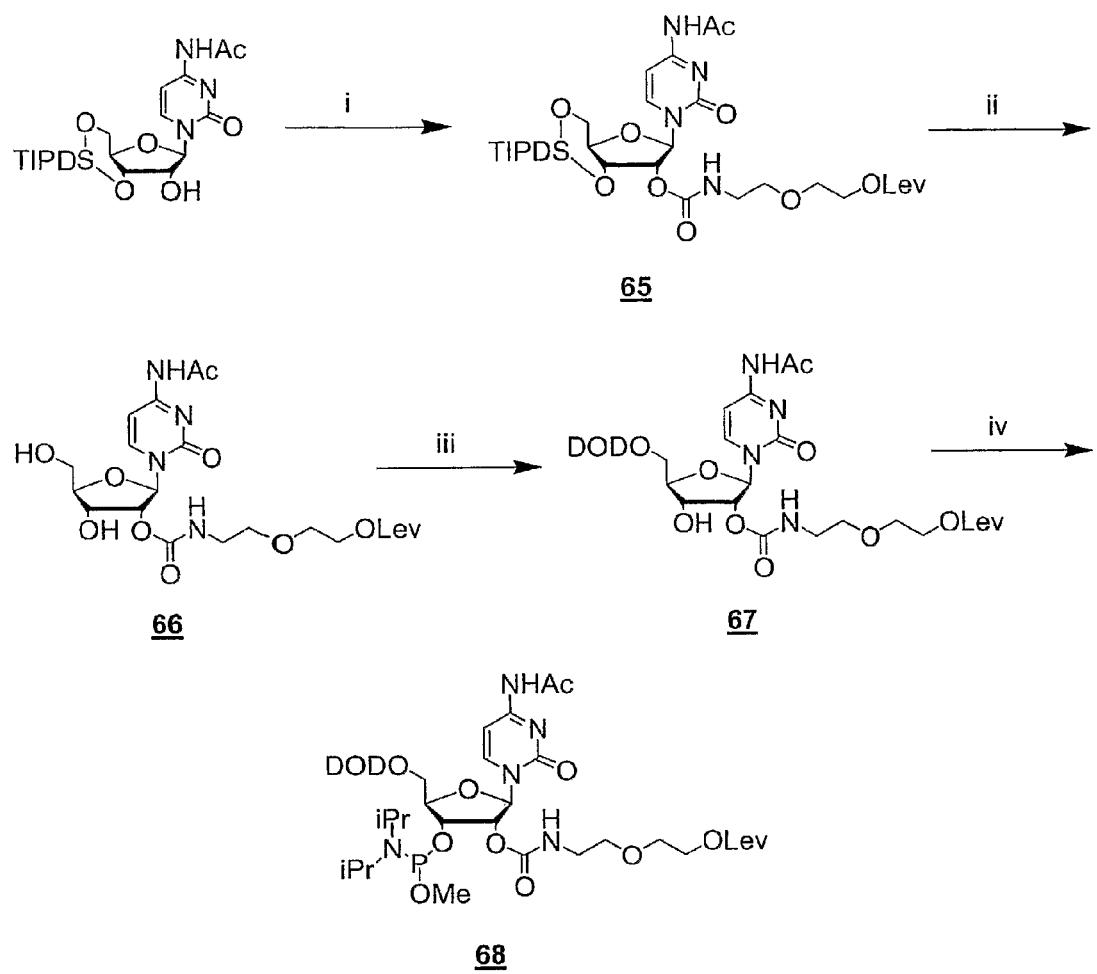
FIG. 13 is a schematic representation of the synthesis of one embodiment of a protected nucleoside phosphoramidite having a linker protected by a levulinyl moiety. In this case the nucleotide base is cytosine, and the linker is attached to the 2'-hydroxyl by a carbamate linkage. The reaction conditions include: (i) a) CDI/DCM; b) 2-(2-aminoethoxy)ethanol; c) levulinic anhydride/TEA/DMAP/DCM; (ii) TEMED/hydrofluoric acid/acetonitrile; (iii) DOD-Cl/diisopropylamine/DCM; (iv) bis(diisopropylamino)methoxy phosphine/5-ethylthio-1H-tetrazole/diisopropylamine/DCM.
Figure 13:
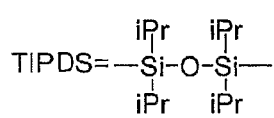
Figure 13:
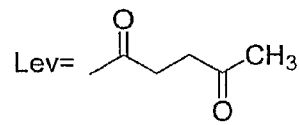
Figure 13:
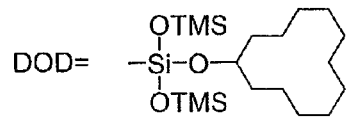

Synthesis of $N^4$-Acetyl-5'-O-[Cyclododecyloxy-Bis(Trimethysilyloxy)Silyl]-2'-O-[2-(2-(4-Oxopentanoate)Oxyethoxy)Ethylamino Carbonyl]Cytidine 3'-O-(N,N,-diisopropylamino)methoxy phosphoramidite 68 (FIG. 13)

$N^4$-Acetyl-2'-O-[2-(2-(4-Oxopentanoate)Oxyethoxy)ethylaminocarbonyl]-3',5'-O-(Tetraisopropyldisiloxane-1,3-Diyl)Cytidine (65)

CDI (4.1 g, 25.5 mmoles) was added to a solution of $N^4$-acetyl-3',5'-O-(tetraisopropyldisiloxane-1,3-diyl)cytidine (12.8 g, 24.2 mmoles) in 240 mL of DCM. After 3 hours the reaction was cooled to 0° C. (ice/water bath) and 2-(2-aminoethoxy)ethanol (3.8 g, 36.3 mmoles) was added. The reaction was stopped after 16 hours and loaded directly onto silica gel for column purification. The crude material was purified by flash chromatography on 300 mL of silica gel using first a mixture of DCM in ethyl acetate (40% (v/v)) and then a mixture of MeOH in ethyl acetate (5% (v/v)). Product fractions were pooled and evaporated to afford a white foam. The yield was 10.83 g (68%). The product was contaminated with a small amount of imidazole and 2-(2-aminoethoxy) ethanol. $^1$H NMR δ (CDCl$_3$, 400 MHz) 8.18 (d, J=7.6 Hz, 1 H), 7.47 (d, J=7.2 Hz, 1 H), 5.88 (s, 1 H), 5.74-5.70 (m, 1 H), 4.32-4.22 (m, 2 H), 4.09-3.94 (m, 2 H), 3.81-3.74 (m, 2 H), 3.60-3.50 (m, 4 H), 3.46-3.32 (m, 2 H), 2.26 (s, 3 H), 1.09-0.091 (m, 28 H); ESMS: (M+H) calculated 659.31, observed 659.28.

Levulinic acid (7.6 g, 65.2 mmoles) was added to a solution of DCC (6.7 g, 32.6 mmoles) in 100 mL of DCM. After 30 minutes the white precipitate was filtered away and the clear solution was evaporated to dryness. To this flask was added the product from the above reaction (10.8 g, 16.3 mmoles) dissolved in 160 mL of DCM, TEA (6.6 g, 65.2 mmoles), and DMAP (0.2 g, 1.6 mmoles). After stirring for 16 hours another 2 equivalents of levulinic anhydride (prepared in the same fashion as above) in 100 mL of DCM were added to the reaction. The reaction was complete after 2 hours. The mixture was diluted with DCM and washed with saturated aqueous sodium bicarbonate. The organic phase was further washed with saturated aqueous sodium chloride and dried by passage through anhydrous sodium sulfate. Evaporation of the solvent left a crude product that was purified by flash chromatography on 400 mL of silica gel -using a gradient of ethyl acetate and acetone in hexanes (0:2:8 to 6:2:2 (v/v/v)). Product fractions were pooled and evaporated to afford a white foam. The yield was 6.23 g (50%). NH NMR δ (CDCl$_3$, 400 mHz) 9.81 (b, 1 H), 8.17 (d, J=7.5 Hz, 1 H), 7.42 (d, J=1 H), 5.89 (s, 1 H), 5.41-5.39 (m, 1 H), 5.30 (m, 1 H), 4.31-4.29 (m, 1 H), 4.26-4.21 (m, 3 H), 4.07-4.05 (m, 1 H), 4.01-3.98 (m, 1 H), 3.67-3.62 (m, 2 H), 3.58-3.51 (m, 2 H), 3.43-3.34 (m, 2 H), 2.78-2.75 (m, 2 H), 2.63-2.60 (m, 1 H), 2.27 (s, 3 H), 2.20 (s, 3 H), 1.12-0.89 (m, 28 H); ESMS: (M+H) calculated 757.35, observed 757.33.

$N^4$-Acetyl-2'-O-[2-(2-(4-Oxopentanoate)Oxyethoxy) Ethylaminocarbonyl]Cytidine (66)

48% aqueous hydrofluoric acid (1.02 mL, 28.2 mmoles) was added dropwise to a solution of TEMED (6.0 mL, 40.2 mmoles) in 50 mL of acetonitrile at 0° C. (ice/water bath). This solution was allowed to stir for 10 minutes and was then added to compound 65 (6.1 g, 8.06 mmoles) in a separate flask. The reaction was stirred for 2.5 hours and concentrated to dryness. The crude material was purified by flash chromatography on 150 mL of silica gel using first DCM containing 0.1% (v/v) TEMED then MeOH in ethyl acetate (3% (v/v)) containing 0.1% (v/v) TEMED. Product fractions were pooled and evaporated to afford a white foam. The yield was 2.19 g (53%). $^1$H NMR δ (d$_6$-DMSO, 400 MHz) 10.94 (s, 1 H), 8.39 (d, J=7.6 Hz, 1H), 7.19 (d, J=7.6 Hz, 1 H), 5.95 (d, J=4.0 Hz, 1 H), 5.05-5.03 (m, 1 H), 4.20-4.17 (m, 1 H), 4.10-4.08 (m, 2 1 H), 3.91-3.89 (m, 1 H), 3.75-3.71 (m, 1 H), 3.61-3.55 (m, 3 H), 3.43-3.36 (m, 5 H), 3.13-3.10 (m, 2 H), 2.71-2.68 (m, 2 H), 2.49-2.45 (m, 2 H), 2.10(s, 3 H), 2.09 (s, 3 H); ESMS: (MPH) calculated 515.20, observed 515.16.

N'-Acetyl-5'-O-[Cyclododecyloxy-Bis(Trimethylsilyloxy)Silyl]-2'-O-[2-(2-(4-Oxopentanoate)Oxyethoxy)Ethylaminocarbonyl]Cytidine (67)

Diisopropylamine (0.44 g, 4.30 mmoles) was added to a solution compound 66 (2.19 g, 4.30 mmoles) in 30 mL of DCM and the solution was cooled to 0° C. (ice/water bath). In a separate flask, DOD-Cl (2.75 g, 6.45 mmoles) was diluted in 10 mL of DCM. Diisopropylamine (0.78 g, 7.74 mmoles) was added dropwise to the silylating solution over 1 minute. The silylating solution was added dropwise to the starting material at 0° C. until TLC analysis showed complete consumption of starting material. The reaction was stopped by the addition of 5 mL of MeOH and evaporated to dryness. The crude material was purified by flash chromatography on 200 mL of silica gel using a gradient of ethyl acetate and acetone in hexanes (0:2:8 to 6:2:2 (v/v/v)) containing 0.1%(v/v) TEA. Product fractions were pooled and evaporated to afford a white foam. The yield was 2.99 g (77%). $^1$H NMR δ (CDCl$_3$, 500 mHz) 9.41 (b, 1 H), 8.36 (d, J=7.5 Hz, 1 H), 7.43 (d, J=7.5 Hz, 1 H), 6.19 (d, J=3.5 Hz, 1 H), 5.85 (m, 1 H), 5.11 (m, 1 H), 4.42-4.39 (m, 1 H), 4.32-4.28 (m, 1H), 4.21-4.17 (m, 1 H), 4.15-4.12 (m, 1 H), 4.20-4.00 (m, 2 H), 3.92-3.87 (m, 1 H), 3.69-3.61 (m, 2 H), 3.55-3.52 (m, 2 H), 3.38-3.32 (m, 2 H), 2.80-2.77 (m, 2 H), 2.63-3.60 (m, 2 H), 2.24 (s, 3 H), 2.21 (s, 3 H), 1.68-1.64 (m, 2 H), 1.45-1.26 (m, 22 H), 0.14 (s, 18 H); ESMS: (M+H) calculated 903.43, observed 903.36.

N$^4$-Acetyl-5'-O-[Cyclododecyloxy-Bis(Trimethylsilyloxy)Silyl]-2'-O-[2-(2-(4-Oxopentanoate)Oxyethoxy)Ethylamino Carbonyl]Cytidine 3'-O-(N,N,-Diisopropylamino)Methoxy Phosphoramidite (68)

Bis(diisopropylamino)methoxy phosphine (1.30 g, 4.95 mmoles) was dissolved in 10 mL of DCM and a 0.45 M solution of 5-ethylthio-1H-tetrazole in anhydrous acetonitrile (3.3 mL, 1.65 mmoles) was added. Diisopropylamine (0.33 g, 3.30 mmoles) was then added and the phosphine solution was allowed to stir for 5 minutes at ambient temperature. In a separate flask compound 67 (2.99 g, 3.30 mmoles) and diisopropylamine (0.33 g, 3.30 mmoles) were dissolved in 15 mL of DCM. The activated phosphine solution was added into the nucleoside solution and the reaction was stirred at room temperature. After 16 hours the reaction was quenched with 5 mL of absolute ethanol and concentrated to dryness. The resulting paste was purified by flash chromatography on 150 mL of silica gel using a mixture of DCM in hexanes (5:95 (v/v)) containing 1% (v/v) TEA followed by acetone in hexanes (3:7 (v/v)) containing 0.1% (v/v) TEA. Product fractions were pooled and evaporated to afford a colorless oil. The yield was 2.62 g (75%).

Figure 14:
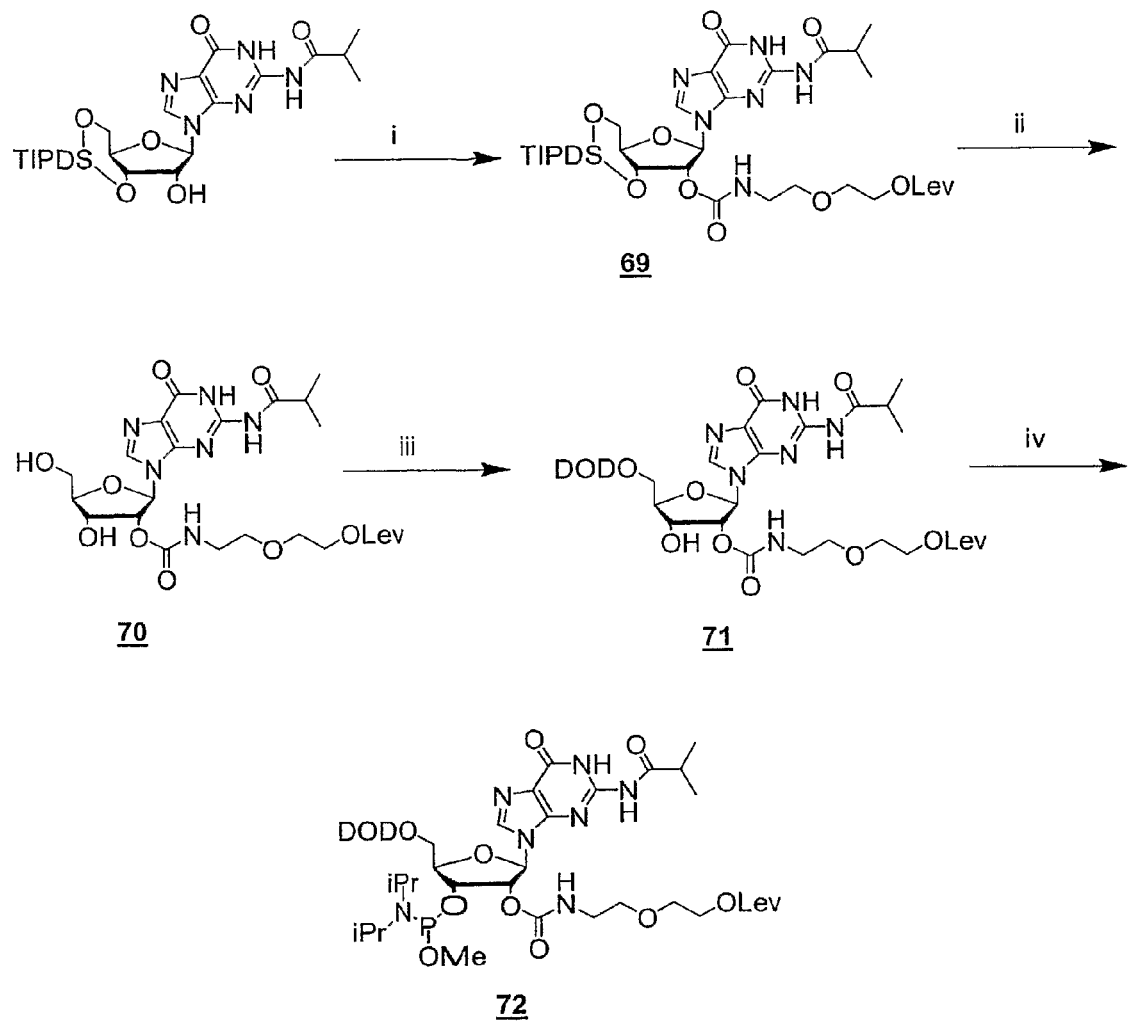
FIG. 14 is a schematic representation of the synthesis of one embodiment of a protected nucleoside phosphoramidite having a linker protected by a levulinyl moiety. In this case the nucleotide base is guanine, and the linker is attached to the 2'-hydroxyl by a carbamate linkage. The reaction conditions include: (i) a) CDI/DCM; b) 2-(2-aminoethoxy)ethanol; c) levulinic anhydride/TEA/DMAP/DCM; (ii) TEMED/hydrofluoric acid/acetonitrile; (iii) DOD-Cl/diisopropylamine/DCM; (iv) bis(diisopropylamino)methoxy phosphine/5-ethylthio-1H-tetrazole/diisopropylamine/DCM.
Figure 14:
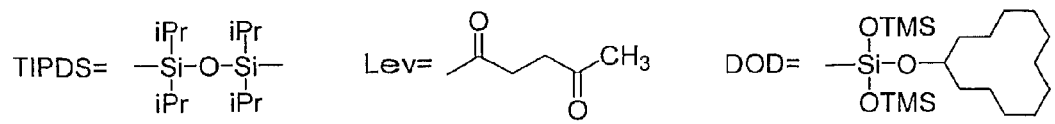

Synthesis of N$^2$-Isobutyryl-5'-O-[Cyclododecyloxy-Bis(Trimethylsilyloxy)Silyl]-2'-O-[2-(2-(4-Oxopentanoate)Oxyethoxy)Ethylamino Carbonyl]Guanosine 3'-O-(N,N,-Diisopropylamino)Methoxy Phosphoramidite (72) (FIG. 14)

N$^2$-Isobutyryl-2'-O-[2-(2-(4-Oxopentanoate)Oxyethoxy)Ethylaminocarbonyl]-3',5'-O-(Tetraisopropyldisiloxane-1,3-Diyl)Guanosine (69)

CDI (4.0 g, 24.5 mmoles) was added to a solution of N$^2$-isobutyryl-3',5'-O-(tetraisopropyldisiloxane-1,3-diyl) guanosine (13.9 g, 23.3 mmoles) in 200 mL of DCM. After 2 hours the reaction was cooled to 0° C. (ice/water bath) and 2-(2-aminoethoxy)ethanol (4.9 g, 46.6 mmoles) was added. The reaction was stopped after 1 hour and loaded directly onto silica gel for column purification. The crude material was purified by flash chromatography on 300 mL of silica gel using first a gradient of MeOH in DCM (5 to 5% (v/v)). Product fractions were pooled and evaporated to afford a white foam. The yield was 16.2 g (96%). The product was contaminated with a small amount of imidazole arid 2-(2-aminoethoxy)ethanol. $^1$H NMR δ (CDCl$_3$, 400 mHz) 8.06 (s, 1 H), 7.85 (s, 1 H), 5.91 (s, 1 H), 5.76-5.73 (m, 1 H), 5.35 (d, J=4.4 Hz, 1 H), 4.52-4.49 (m, 1 H), 4.264.22 (m, 1 H), 4.07-3.98 (m, 2 H), 3.86-3.78 (m, 2 H), 3.72-3.64 (m, 4 H), 3.19-3.14 (m, 1 H), 2.700-2.64 (m, 1 H), 1.27-1.23 (m, 6 H), 1.09-0.89 (m, 28 H); ESMS: (M+H) calculated 727.34, observed 727.31.

Levulinic acid (6.7 g, 58.0 mmoles) was added to a solution of DCC (6.0 g, 29.0 mmoles) in 100 mL of DCM. After 30 minutes the white precipitate was filtered away and the clear solution was evaporated to dryness. To this flask was added the product from the above reaction (16.2 g, 22.3 mmoles) dissolved in 220 mL of DCM, TEA (9.0 g, 89.2 mmoles), and DMAP (0.3 g, 2.2 mmoles). After stirring for 2 hours another 0.5 equivalents of levulinic anhydride (prepared in the same fashion as above) in 100 mL of DCM was added to the reaction. The reaction was complete after 30 minutes. The mixture was diluted with DCM and washed with saturated aqueous sodium bicarbonate. The organic phase was further washed with saturated aqueous sodium chloride and dried by passage through anhydrous sodium sulfate Evaporation of the solvent left a crude product that was purified by flash chromatography on 300 mL of silica gel using a gradient of MeOH in DCM (0% to 1% (v/v)). Product fractions were pooled and evaporated to afford a white foam. The yield was 13.0 g (71%). $^1$H NMR δ (CDCl$_3$, 400 MHz) 12.10 (b, 1 H), 9.34 (s, 1 H), 7.92 (s, 1 H), 5.87 (s, 1 H), 5.63-5.61 (m, 1 H), 5.42 (d, J=5.2 Hz, 1 H), 4.60-4.57 (m, 1 H), 4.29-4.13 (m, 3 H, 4.03-3.97 (m, 2 H), 3.67-3.64 (m, 2 H), 3.61-3.54 (m, 2 H), 3.48-3.41 (m, 1 H), 3.36-3.28 (m, 1 H), 2.80-2.74 (m, 2 H), 2.65-2.59 (m, 2 H), 2.20 (s, 1 H), 1.23 (d, J=6.8 Hz, 6 H), 1.08-0.93 (m, 28 H); ESMS: (M+H) calculated 825.38, observed 825.36.

N$^2$-Isobutyryl-2'-O-[2-(2-(4-Oxopentanoate)Oxyethoxy)Ethylaminocarbonyl]Guanosine (70)

48% aqueous hydrofluoric acid (2.0 mL, 55.0 mmoles) was added dropwise to a solution of TEMED (12.0 mL, 79.0 mmoles) in 100 mL of acetonitrile at 0° C. (ice/water bath). This solution was allowed to stir for 10 minutes and was then added to compound 69 (13.0 g, 15.8 mmoles) in a separate flask. The reaction was stirred for 3 hours and concentrated to dryness. The crude material was purified by flash chromatography on 300 mL of silica gel using first DCM containing 0.1% (v/v) TEMED then MeOH in DCM (5% (v/v)) containing 0.1% (v/v) TEMED. Product fractions were pooled and evaporated to afford a white foam. The yield was 10.8 g. The product was contaminated with a small amount of TEMED. $^1$H NMR δ (CDCl$_3$, 500 MHz) 7.94 (s, 1 H), 6.06-6.05 (m, 1 H), 5.92 (d, J=5.0 Hz, 1 H), 5.61-5.59 (m, 1 H), 4.30-4.24 (m, 2 H), 4.18-4.16 (m, 2 H), 3.95-3.92 (m, 1 H), 3.84-3.78 (m, 1 H), 3.70-3.58 (m, 3 H), 3.53-3.49 (m, 2 H), 3.36-3.26 (m, 3 H), 3.10-3.05 (m, 3 H), 2.80-2.74 (m, 2 H), 2.62-2.59 (m, 2 H), 2.20 (s, 3 H), 1.24 (d, J=5.0 Hz, 6 H); ESMS: (M+H) calculated 583.24, observed 583.19.

N$^2$-Isobutyryl-5'-O-[Cyclododecyloxy-Bis(Trimethylsilyloxy)Silyl]-2'-O-[2-(2-(4-Oxopentanoate)Oxyethoxy)Ethylamino Carbonyl]Guanosine (71)

Diisopropylamine (4.6 g, 15.8 mmoles) was added to a solution compound 70 (9.20 g, 15.8 mmoles) in 32 mL of DCM and the solution was cooled to 0° C. (ice/water bath). In a separate flask, DOD-Cl (10.1 g, 23.7 mmoles) was diluted in 28 mL of DCM. Diisopropylamine (2.88 g, 28.4 mmoles) was added dropwise to the silylating solution over 1 minute. The silylating solution was added dropwise to the starting material at 0° C. until TLC analysis showed complete consumption of starting material. The reaction was stopped by the addition of 30 mL of MeOH and evaporated to dryness. The crude material was purified by flash chromatography on 500 mL of silica gel using a gradient of MeOH in DCM (0% to 4% (v/v)) containing 0.1% (v/v) TEA. Product fractions were pooled and evaporated to afford a white foam. The yield was 12.8 g (83%). $^1$H NMR δ (CDCl$_3$, 500 MHz) 12.12 (s, 1 H), 9.69 (s, 1 H), 9.02 (s, 1 H), 8.08 (s, 1 H), 6.08 (b, 1 H), 6.05 (d, J=5.5 Hz, 1 H), 5.55 (m, 1 H), 4.67 (m, 1 H), 4.24-4.18 (m, 4 H), 4.04-3.99 (m, 1 H), 3.92-3.86 (m, 2 H), 3.64-3.60 (m, 2 H), 3.53-3.50 (m, 1 H), 3.48-3.40 (m, 1 H), 3.37-3.32 (m, 1 H), 3.29-3.24 (m, 1 H), 2.81-2.78 (m, 2 H), 2.63-2.61 (m, 2 H), 2.22 (s, 3 H), 1.66-1.62 (m, 2 H), 1.48-1.22 (m, 28 H), 0.13 (s, 18 H); ESMS: (M+H) calculated 971.47, observed 971.38.

N²-Isobutyryl-5'-O-[Cyclododecyloxy-Bis(Trimethylsilyloxy)Silyl]-2'-O-[2-(2-(4-Oxopentanoate)Oxyethoxy)Ethylamino Carbonyl]Guanosine 3'-O-(N,N,-Diisopropylamino)Methoxy Phosphoramidite (72)

Bis(diisopropylamino)methoxy phosphine (2.76 g, 10.54 mmoles) was dissolved in 50 mL of DCM and a 0.45 M solution of 5-ethylthio-1H-tetrazole in anhydrous acetonitrile (7.80 mL, 3.51 mmoles) was added. Diisopropylamine (0.71 g, 7.02 mmoles) was then added and the phosphine solution was allowed to stir for 5 minutes at ambient temperature. In a separate flask compound 71 (6.82 g, 7.02 mmoles) and diisopropylamine (0.71 g, 7.02 mmoles) were dissolved in 50 mL of DCM. The activated phosphine solution was added into the nucleoside solution and the reaction was stirred at room temperature. After 16 hours the reaction was quenched with 25 mL of absolute ethanol and concentrated to dryness. The resulting paste was purified by flash chromatography on 250 mL of silica gel using a mixture of DCM in hexanes (5:95 (v/v)) containing 1% (v/v) TEA followed by acetone in hexanes (3:7 (v/v)) containing 0.5% (v/v) TEA. Product fractions were pooled and evaporated to afford a colorless oil. The yield was 7.1 g (90%).

Example 4

Figure 15:
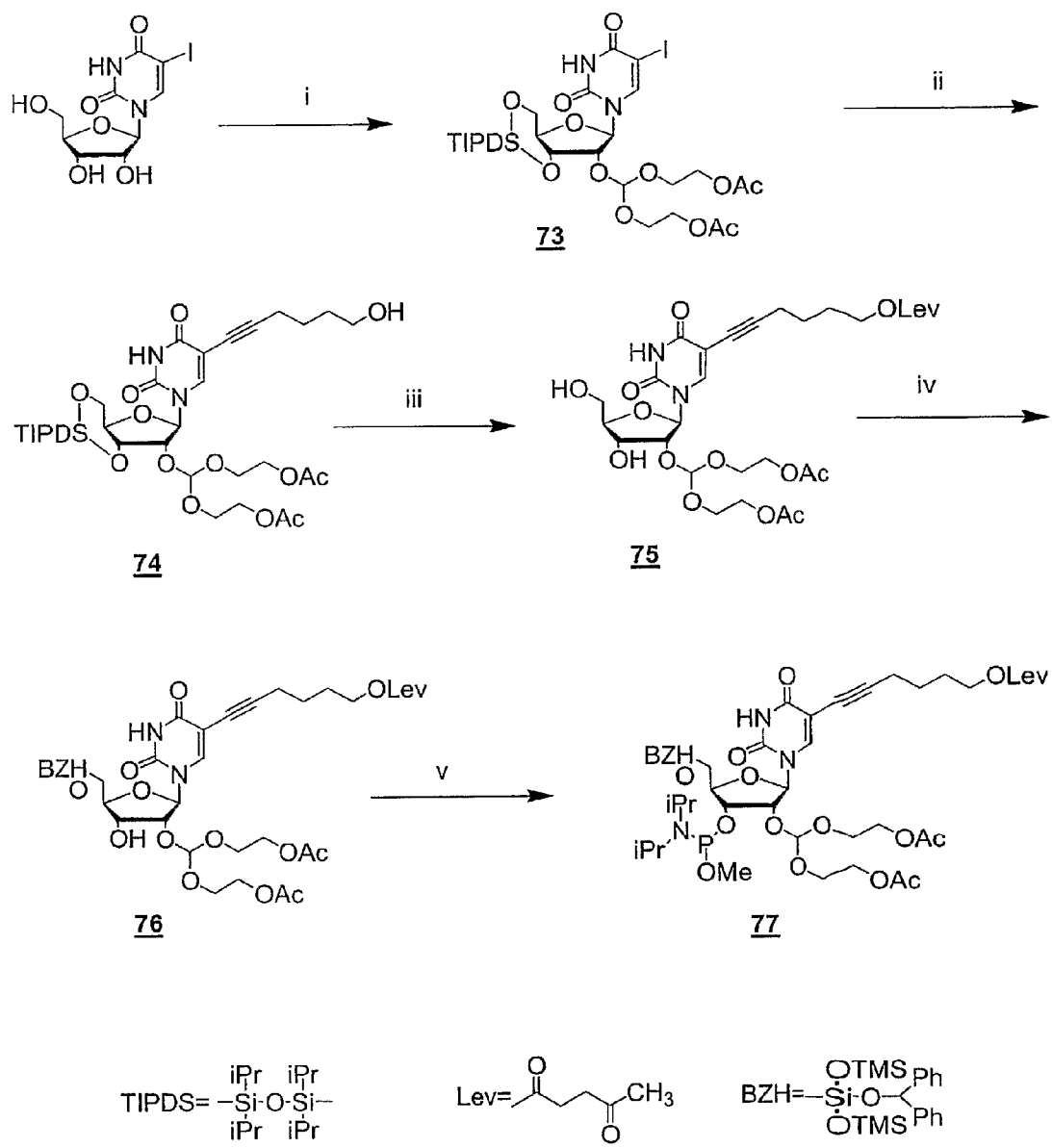
FIG. 15 is a schematic representation of the synthesis of one embodiment of a protected nucleoside phosphoramidite having a linker protected by a levulinyl moiety. In this case, the linker is attached to the 5-position of the uracil base. The reaction conditions include: (i) a) TIPDS-Cl$_2$/pyridine; b) tris(acetoxyethyl)orthoformate/TBDMS-pentanedione/pyridinium p-toluenesulfonate/DCM; (ii) tetrakis(triphenylphosphine)palladium(0)/copper(I) iodide/5-hexyn-1-ol/DMF; (iii) a) levulinic anhydride/TEA/DMAP/DCM; b) TEMED/hydrofluoric acid/acetonitrile; (iv) BZH-Cl/diisopropylamine/DCM; (v) bis(diisopropylamine)methoxy phosphine/5-ethylthio-1H-tetrazole/diisopropylamine/DCM.

Synthesis of a Nucleoside Phosphoramidite with a Linker Protected by a Levulinyl Moiety at the Nitrogenous Base and Having a 5'-Silyl Protecting Group A nucleoside phosphoramidite comprising a linker protected by a levulinyl moiety, or derivative thereof, at the nitrogenous base and having a 5'-silyl protecting group was prepared in the manner described below. The methods are illustrated in FIG. 15 and are detailed below for the particular example given.

In general, the initial step of the procedure was the attachment of the linker group to the nitrogenous base of the desired nucleoside. Methods for forming carbon-carbon bonds at the 5-position of uridine and cytidine (for example, palladium-catalyzed couplings of allyl or vinyl derivatives to 5-mercuriuridine or 5-mercuricytidine, or of propargyl derivatives to 5-iodouridine, 5-iodocytidine, 7-iodo-7-deazaadenosine and 7-iodo-7-deazaguanosine) and for forming carbon-nitrogen bonds at the 4-position of cytidine (for example, bisulfite-catalyzed transamination or conversion of 4-triazolyl- or 4-arylsulfonyluridine) and the 6-position of adenosine (for example, amination of 6-choropurineriboside) are well known to those skilled in the art. Incorporation of a linker protected by a levulinyl moiety was accomplished by selecting an appropriate alcohol derivative (for example, allyl alcohol, propargyl alcohol, 6-amino-1-hexanol or 2-(2-aminoethoxy)ethanol), reacting the hydroxyl group with levulinic anhydride in a manner similar to that in the previous examples, and then utilizing the appropriate coupling chemistry.

If the desired nucleoside phosphoramidite was a ribonucleoside, the linker-modified nucleoside was protected at the nitrogenous base using standard reactions similar to those described in the previous examples. The 3'- and 5'-hydroxyl groups were then simultaneously protected with 1,3-dichloro-1,1,3,3-tetraisopropyldisiloxane in pyridine solution. The free 2'-hydroxyl was protected as its ACE derivative using tris(acetoxyethyl)orthoformate in the presence of pyridinium p-toluenesulfonate and t-butyldimethylsilyl-pentanedione in dichloromethane. The silyl protection on the 3'- and 5'-hydroxyl groups was removed with fluoride ion in an appropriate solvent (for example, tetrahydrofuran or acetonitrile). The 5'-hydroxyl was protected with, for example, benzhydryloxy-bis(trimethylsilyloxy)chlorosilane in dichloromethane and diisopropylamine. Finally, the free 3'-hydroxyl was reacted with, for example, bis(diisopropylamino)methoxy phosphine in the presence of a tetrazole catalyst to produce the desired nucleoside phosphoramidite.

If the desired nucleoside phosphoramidite did not have a free 2'-hydroxyl (for example, 2'-deoxy, 2'-O-methyl, or 2'-fluoro), the linker-modified nucleoside was protected at the nitrogenous base using standard reactions similar to those described in the previous examples. The 5'-hydroxyl was protected with, for example, benzhydryloxy-bis(trimethylsilyloxy)chlorosilane in dichloromethane and diisopropylamine. Finally, the free 3'-hydroxyl was reacted with, for example, bis(diisopropylamino)methoxy phosphine in the presence of a tetrazole catalyst to produce the desired nucleoside phosphoramidite.

Synthesis of 5'-O-[Benzhydryloxy-Bis(Trimethylsiloxy)Silyl]-2'-O-Bis(2-Acetoxyethoxy)Methyl-5-[6-(4-Oxopentanoate)Oxy-1-Hexynyl]Uridine 3'-O-(N,N,-Diisopropylamino)Methoxy Phosphoramidite (77)

2'-O-Bis(2-Acetoxyethoxy)Methyl-5-Iodo-3',5'-O-(Tetraisopropyldisiloxane-1,3-Diyl)Uridine (73)

TIPDS-Cl$_2$ (14.38 g, 45.6 mmoles) was added dropwise over 1 hour at 0° C. (ice/water bath) to a solution of 5-iodouridine (15.4 g, 41.5 mmoles) in 160 mL of pyridine. The reaction was allowed to gradually warm to room temperature and was quenched with 30 mL of MeOH after 16 hours. The solution was concentrated to dryness and partitioned between DCM and water. The organic phase was washed with saturated aqueous sodium bicarbonate, dried by passage over anhydrous sodium sulfate and evaporated to leave a white paste. The crude material was purified by flash chromatography on 750 mL of silica gel using a gradient of MeOH in DCM (0% to 0.5% (v/v)). Product fractions were pooled and evaporated to afford a white foam. The yield was 24.2 g (95%).

The product from the preceding reaction (24.2 g, 39.5 mmoles) was combined with tis(acetoxyethyl)orthoformate (30.8 g, 95.5 mmoles) and pyridinium p-toluenesulfonate (2.1 g, 8.3 mmoles) in 100 mL of DCM. The solution was stirred for 1 hour and tert-butyldimethylsilyl-pentanedione (16.0 g, 74.7 mmoles) was added. The reaction was stirred for 4 days and quenched with TEMED (2.4 g, 20.8 mmoles). The solution was diluted with 500 mL of hexanes and this solution was purified directly by flash chromatography on 1500 mL of silica gel using first a mixture of ethyl acetate in hexanes (25% (v/v)) containing 0.05% (v/v) TEA and then a mixture of ethyl acetate and MeOH in hexanes (45:1:54 (v/v)). Product fractions were pooled and evaporated to afford a colorless oil. The yield was 27.0 g (82%).

2'-O-Bis(2-Acetoxyethoxy)Methyl-5-(6-Hydroxy-1-Hexynyl)-3',5'-O-(Tetraisopropyldisiloxane-1,3-Diyl)Uridine (74)

Tetrakis(triphenylphosphine)palladium(0) (0.81 g, 0.70 mmoles), copper(I) iodide (0.27 g, 1.40 mmoles), TEA (1.41 g, 14.0 mmoles), and 5-hexyn-1-ol (2.05 g, 20.9 mmoles) were added to a solution of compound 73 (5.80 g, 7.0 mmoles) in 70 mL of DMF. The reaction was stirred for 20 hours and then diluted with ethyl acetate. The organic solution was washed with saturated aqueous sodium bicarbonate. The aqueous phase was extracted two more times with ethyl acetate and the pooled organics were washed with saturated aqueous sodium chloride. The organic phase was dried by passage over anhydrous sodium sulfate and evaporated to dryness. The resulting brown paste was purified by flash chromatography on 250 mL of silica gel using a gradient of ethyl acetate in hexanes (50% to 60% (v/v)) containing 0.05% (v/v) TEA. Product fractions were pooled and evaporated to afford a brown oil that contained excess 5-hexyn-1-ol. Yield was 6.11 g. ESMS: (M+TEA-H) calculated 902.48, observed 902.41.

2'-O-Bis(2-Acetoxyethoxy)Methyl-5-[6-(4-Oxopentanoate)Oxy-1-Hexynyl]Uridine (75)

Levulinic acid (4.88 g, 42.0 mmoles) was added to a solution of DCC (4.33 g, 21.0 mmoles) in 70 mL of DCM. After 30 minutes the white precipitate was filtered away and the clear solution was evaporated to dryness. To this flask was added compound 74 (6.11 g, 7.0 mmoles) in 70 mL of DCM, TEA (3.54 g, 35.0 mmoles), and DMAP (0.09 g, 0.70 mmoles). After 1 hour the mixture was diluted with DCM and washed with saturated aqueous sodium bicarbonate. The organic phase was further washed with saturated aqueous sodium chloride and dried by passage over anhydrous sodium sulfate. Evaporation of the solvent left a light brown paste that was purified by flash chromatography on 200 mL of silica gel using a gradient of MeOH in DCM (0% to 0.5% (v/v)) containing 0.05% (v/v) TEA. Product fractions were pooled and evaporated to afford a light yellow oil. The yield was 6.08 g (97%). ESMS: (M+Na) calculated 921.38, observed 921.28.

48% aqueous hydrofluoric acid (0.85 mL, 23.7 mmoles) was added dropwise to a solution of TEMED (5.1 mL, 33.8 mmoles) in 40 mL of acetonitrile at 0° C. (ice/water bath). This solution was allowed to stir for 5 minutes and added to product of the above reaction (6.08 g, 6.76 mmoles) in a separate flask. The reaction was stirred for 1 hour and concentrated to dryness. The crude material was purified by flash chromatography on 200 mL of silica gel using a gradient of ethyl acetate in hexanes (50% to 100% (v/v)) containing 0.1% (v/v) TEMED. Product fractions were pooled and evaporated to afford a light yellow oil. The yield was 2.56 g (58%). $^1$H NMR δ (CDCl$_3$, 400 MHz) 8.52 (s, 1 H), 8.14 (s, 1 H), 5.89 (d, J=4.8 Hz, 1 H), 5.47 (s, 1 H), 4.56-4.53 (m, 1 H), 4.36-4.34 (m, 1 H), 4.26-4.21 (m, 4 H), 4.16-4.06 (m, 4 H), 4.03-3.98 (m, 1 H), 3.84-3.75 (m, 5 H), 3.44-3.41 (m, 1 H), 3.00 (d, J=4.8 Hz, 1 H), 2.78-2.75 (m, 2 H), 2.47-2.44 (m, 2 H), 2.21 (s, 3 H), 2.08 (s, 6 H), 1.80-1.74 (m, 2 H), 1.64-1.60 (m, 2 H); ESMS: (M+TEA-H) calculated 758.37, observed 758.51.

5'-O-[Benzhydryloxy-Bis(Trimethylsilyloxy)Silyl]-2'-O-Bis(2-Acetoxyethoxy)Methyl-5-[6-(4-Oxopentanoate)Oxy-1-Hexynyl]Uridine (76)

Diisopropylamine (0.39 g, 3.9 mmoles) was added to a solution compound 75 (2.56 g, 3.9 mmoles) in 30 mL of DCM and the solution was cooled to 0° C. (ice/water bath). In a separate flask, BZH-Cl (2.50 g, 5.85 mmoles) was diluted in 20 mL of DCM. Diisopropylamine (0.71 g, 7.0 mmoles) was added dropwise to the silylating solution over 1 minute. The silylating solution was added dropwise to the starting material at 0° C. until TLC analysis showed complete consumption of starting material. The reaction was stopped by the addition of 10 mL of MeOH and evaporated to dryness. The crude material was purified by flash chromatography on 150 mL of silica gel using a gradient of ethyl acetate and acetone in hexanes (0:2:8 to 2:2:6 (v/v)) containing 0.1%(v/v) TEA. Product fractions were pooled and evaporated to afford a colorless oil. The yield was 3.34 g (82%). $^1$H NMR δ (CD$_3$CN, 500 MHz) 7.66 (s, 1 H), 7.41-7.39 (m, 4 H), 7.33-7.29 (m, 4 H), 7.24-7.22 (m, 2 H), 6.00 (s, 1 H), 5.87 (d, J=5.5 Hz, 1 H), 5.35 (s, 1 H), 4.22 (t, J=5.5 Hz, 1 H), 4.16-4.12 (m, 3 H), 4.01-3.99 (m, 3 H), 3.90 (q, J=3.5 Hz, 1 H), 3.75-3.36 (m, 5 H), 2.69 (t, J=6.0 Hz, 2 H), 2.44 (t, J=7.0 Hz, 2 H), 2.32 (t, J=7.5 Hz, 2 H), 2.09 (s, 3 H), 2.00 (s, 6 H), 1.70-1.65 (m, 2 H), 1.59-1.54 (m, 2 H), 0.08 (s, 9 H), 0.07 (s, 9 H); ESMS: (M+Na) calculated 1067.37, observed 1067.21.

5'-O-[Benzhydryloxy-Bis(Trimethylsilyloxy)Silyl]-2'-O-Bis(2-Acetoxyethoxy)methyl-5-[6(4-Oxopentanoate)Oxy-1-Hexynyl]Uridine 3'-O-(N,N,-Diisopropylamino)Methoxy Phosphoramidite (77)

Bis(diisopropylamino)methoxy phosphine (1.10 g, 4.2 mmoles) was dissolved in 10 mL of DCM and a 0.45 M solution of 5-ethylthio-1H-tetrazole in anhydrous acetonitrile (3.1 mL, 1.4 mmoles) was added. Diisopropylamine (0.28 g, 2.8 mmoles) was then added and the phosphine solution was allowed to stir for 5 minutes at ambient temperature. In a separate flask compound 76 (2.94 g, 2.8 mmoles) and diisopropylamine (0.28 g, 2.8 mmoles) were dissolved in 10 mL of DCM. The activated phosphine solution was added into the nucleoside solution and the reaction was stirred at room temperature. After 16 hours the reaction was quenched with 10 mL of absolute ethanol and concentrated to dryness. The resulting paste was purified by flash chromatography on 150 mL of silica gel using a mixture of DCM in hexanes (5:95 (v/v)) containing 1% (v/v) TEA followed by acetone in hexanes (3:7 (v/v)) containing 0.5% (v/v) TEA. Product fractions were pooled and evaporated to afford a colorless oil. The yield was 2.36 g (70%).

Example 5

Synthesis of a Solid Support with a Linker Protected by a Levulinyl Moiety

Solid supports comprising a linker protected by a levulinyl moiety, or derivative thereof, were prepared in the manner described below. The methods are illustrated in FIG. 16 and are detailed below for the particular example given.

Common solid supports for polynucleotide synthesis are controlled pore glass, polystyrene, and polymethacrylate. Typically the supports are relatively rigid and non-swelling, properties that are advantageous for flow-based synthetic processes employing solvents of widely differing polarity. The surface was generally chemically functionalized with a primary amine to enable covalent attachment of the 3'-terminal moiety to the support. Common linkages between the support and the 3'-terminal moiety are, by way of example, succinate, glutarate and oxalate, which provide a stable bond to the support during the chain assembly process but are readily cleaved post-assembly to release the polynucleotide into solution.

In general, a protected branched triol (for example, glycerol or 1,2,6-hexanetriol) was reacted at a single specific hydroxyl with levulinic anhydride in a manner similar to that described in the previous examples. The remaining hydroxyl groups were deprotected. One of the liberated hydroxyl groups was then reacted with dimethoxytrityl chloride in pyridine. The remaining hydroxyl was treated with a reactive dicarboxylic acid derivative (for example, succinic anhydride, glutaric anhydride, or oxalyl chloride). This acid-modified linker was then activated (for example, with dicyclohexylcarbodiimide and 4-nitrophenol, or with 2-(1H-benzotriazole-1-yl)-1,1,3,3-tetramethyluronium tetrafluoroborate and 1-hydroxybenzotriazole) and reacted with the amine-functionalized solid support, forming a covalent amide bond. The amount of linker bound to the support (the "loading") can be regulated by the amount of linker-acid derivative used in this reaction, and by the length of time the reaction was allowed to proceed. The loading of the support was conveniently estimated by cleaving the DMTr group from the linker with anhydrous acid (using, for example, 3% dichloroacetic acid in dichloromethane or 0.1 M p-toluenesulfonic acid in acetonitrile), and measuring the quantity of the orange-colored DMTr cation present in the acid solution spectrophotometrically.

Figure 16:
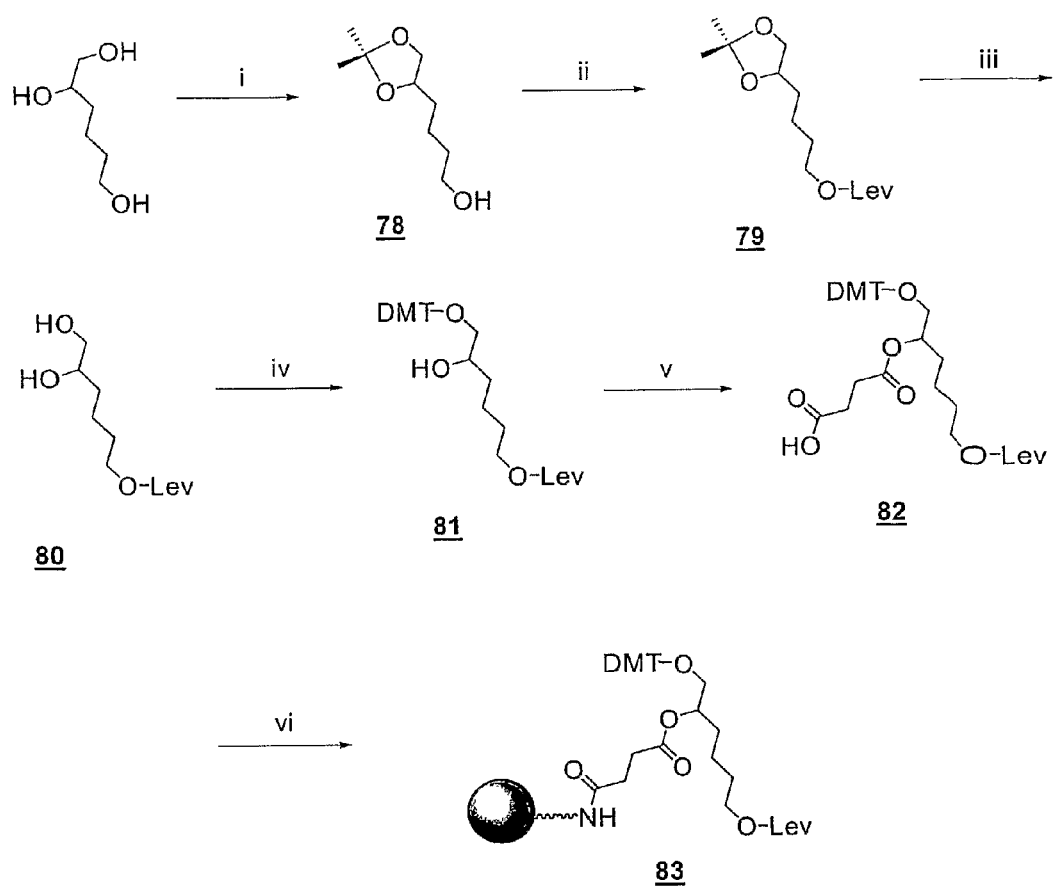
FIG. 16 is a schematic representation of the synthesis of one embodiment of a solid synthesis support having a linker protected by a levulinyl moiety. Reaction conditions include: (i) 2,2,-dimethoxypropane/p-toluenesulfonic acid monohydrate; (ii) levulinic anhydride/DMAP/pyridine; (iii) Dowex 50WX8 (H+form)/MeOH/water; (iv) DMTr-Cl/TEA/DMAP/pyridine; (v) succinic anhydride/N-methylimidazole/TEA/DCM; (vi) aminomethyl-polystyrene/BOP/HOBt/TEA/DMF.
Figure 16:
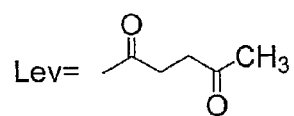

Synthesis of a Polystyrene Synthesis Support Derivatized with 1-(4,4'-Dimethoxytrityl)-6-(4-Oxopentanoyl)-1,2,6-Hexanetriol 2-Hemisuccinate (83) (FIG. 16)

1,2-Isopropylidene-1,2,6-Hexanetriol (78)

1,2,6-trihydroxyhexane (67.5 g, 503 mmoles), 2,2-dimethoxypropane (280 mL, 2.28 mmoles) and p-toluenesulfonic acid monohydrate (9.5 g, 50 mmoles) were combined and stirred at room temperature for 20 hours. At this time, all of the triol had dissolved and TLC (95:5 (v/v) DCM: MeOH, visualized using 5% (w/v) phosphomolybdic acid in ethanol) indicated no residual triol present. Anhydrous potassium carbonate (10.0 g, 72.3 mmoles) was added and the mixture was stirred until it was no longer acidic to pH paper. The mixture was filtered and the solid washed with a little acetone. The filtrate and acetone washings were evaporated to remove the volatile solvents. The residual oil was dissolved in 500 mL of cyclohexane, filtered, and the cyclohexane was evaporated. The remaining pale yellow liquid was distilled under vacuum (2-3 torr) at an oil bath temperature of 145-155° C. and a vapor temperature of 108-113° C. The yield was 90.5 g of a clear, viscous liquid. TLC in the above solvent system showed two species in the distillate, a slower-moving (major) species (the desired product) and a faster-moving (minor) species. The desired product was purified from the mixture (25 g) by flash chromatography on 600 mL of silica gel using a gradient of ethyl acetate in hexanes (0% to 100% (v/v)). Product fractions were pooled and evaporated to afford a colorless liquid. The yield was 11.5 g. $^1$H NMR (400 MHz, CDCl$_3$): 4.03 (m, 1 H), 3.96 (t, 1 H, J=6.0 Hz), 3.54 (q, 2 H, J=5.9 Hz), 3.43 (t, 1 H, J=7.4 Hz), 2.62 (t, 1 H, J=5.0 Hz), 1.59-1.43 (m, 5 H), 1.36-1.29 (m, 1 H), 1.34 (s, 3 H), 1.28 (s, 3 H).

1,2-Isopropylidene-6-(4-Oxopentanoyl)-1,2,6-Hexanetriol (79)

Levulinic acid (14-6 g, 125.2 mmoles) was added to a solution of DCC (12.9 g, 62.6 mmoles) in 200 mL of DCM. After 15 minutes the white precipitate was filtered away and the clear solution was evaporated to dryness. To this flask was added compound 78 (10 g, 57.4 mmoles) in 50 mL of pyridine and DMAP (1.5 g, 12.3 mmoles). The reaction mixture darkened. After 16 hours the reaction was stopped with 20 mL of MeOH. Evaporation of the solvent left a brown oil that was dissolved in 400 mL of ethyl acetate. The organic solution was washed three times with saturated aqueous sodium bicarbonate followed by one wash with saturated aqueous sodium chloride. The organic extract was dried over anhydrous sodium sulfate, filtered and evaporated to a yellow oil. The crude product was purified by flash chromatography on 300 mL of silica gel using a gradient of ethyl acetate in hexanes (0% to 25% (v/v)). Product fractions were pooled and evaporated to afford a pale yellow liquid. The yield was 15.1 g (96%). $^1$H NMR (400 MHz, CDCl$_3$): 4.02 (t, 2 H, J=6.8 Hz), 4.00 (m, 1 H), 3.98 (t, 1 H, J=5.6 Hz), 3.45 (t, 1 H, J=7.2 Hz), 2.70 (t, 2 H, J=6.4 Hz), 2.51 (t, 2 H, J=6.4 Hz), 2.14 (s, 3 H), 1.66-1.54 (m, 2 H), 1.54-1.37 (m, 4 H), 1.35 (s, 3 H), 1.29 (s, 3 H).

6-(4-Oxopentaonyl)-1,2,6-Hexanetriol (80)

Compound 79 (15.1 g, 55.4 mmoles) was dissolved in 100 mL of MeOH:water (9:1 (v/v)), and 10 g of MeOH-washed, air-dried DOWEX 50WX8-100 ion exchange resin (H$^+$ form) was added. After 6 hours at room temperature, TLC (1:1 (v/v) ethyl acetate:hexanes) indicated the reaction was complete. The resin was removed by filtration and washed well with MeOH. The combined filtrates were evaporated to a pale yellow liquid. The crude product was purified by flash chromatography on 300 mL of silica gel using a gradient of ethanol in ethyl acetate (0% to 1% (v/v)) Product fractions were pooled and evaporated to afford a colorless liquid. The yield was 10.8 g (84%). $^1$H NMR (400 MHz, CDCl$_3$): 4.06 (t, 2 H, J=6.6 Hz), 4.05 (m, 1 H), 3.65 (m, 1 H), 3.60 (dd, 1 H, J=8.0 Hz), 3.41 (dd, 1 H, J=7.6 Hz), 3.06 (br s, 2H), 2.74 (t, 2 H, J=6.4 Hz), 2.54 (t, 2 H, J=6.4 Hz), 2.17 (s, 3 H), 1.66-1.40 (m, 5 H).

1-(4,4'-Dimethoxytrityl)-6-(4-Oxopentanoyl)-1,2,6-Hexanetriol (81)

Compound 80 (5.0 g, 21.5 mmoles) was dissolved in 50 mL of dry pyridine. TEA (4.2 mL, 30.1 mmoles), DMAP (0.3 g, 2-5 mmoles) and DMTr-Cl (7.6 g, 22.4 mmoles) were added and the reaction was stirred at ambient temperature. After 30 minutes, a precipitate had thickened the reaction, and 50 mL of DCM were added. After 3 hours, TLC (1:1 (v/v) ethyl acetate:hexanes) indicated reaction was complete. Ethanol (10 mL) was added, and the mixture was evaporated to a dark yellow syrup. The crude product was purified by flash chromatography on 400 mL of silica gel using a gradient of ethyl acetate in hexanes (1:4 to 1:2 (v/v)) containing 2% (v/v) TEA. Product fractions were pooled and evaporated to afford a yellow syrup. The yield was 10.3 g (89%).

1-(4,4'-Dimethoxytrityl)-6-(4-Oxopentanoyl)-1,2,6-Hexanetriol 2-Hemisuccinate (82)

Compound 81 (10.3 g, 19.3 mmoles) was dissolved in 200 mL of DCM. TEA (8.1 mL, 57.9 mmoles), N-methylimidazole (0.8 mL, 9.7 mmoles) and succinic anhydride (2.1 g, 21.2 mmoles) were added, and the solution was stirred at ambient temperature. After 2 days the reaction mixture was evaporated to a dark brown syrup. The crude product was purified by flash chromatography on 400 mL of silica gel using a gradient of methanol in DCM (0% to 5% (v/v)) containing 5% (v/v) TEA. Product fractions were pooled and evaporated to afford a light brown glassy foam. The yield was 8.9 g (62%).

1-(4,4'-Dimethoxytrityl)-6-(4-Oxopentanoyl)-1,2,6-Hexanetriol 2-Hemisuccinate Derivatized Polystyrene Synthesis Support (83)

10 g of aminomethyl-polystyrene synthesis support was placed in a 250 mL round bottom flask and 75 mL of DMF were added. The flask was capped with a rubber septum and placed on a wrist-action shaker to vigorously agitate the support Compound 82 (88 mg, 0.12 mmoles) was dissolved in 25 mL of DMF in a 100 mL round bottom flask. TEA (33 µL, 0.24 mmoles), BOP (58 mg, 0.13 mmoles) and HOBt (19 mg, 0.14 mmoles) were added, and the flask was capped with a rubber septum. The flask was swirled to dissolve the solids, and allowed to sit at ambient temperature for 15 minutes. 14 mL (0.067 mmoles) of this solution was then added to the flask containing the support, and reaction was allowed to proceed at ambient temperature for 4.5 hours. The support was then washed well on a glass-fritted funnel with DMF, acetone, methanol and acetonitrile. The support was then dried over night under vacuum. The next day, the support was suspended in a mixture of 50 mL of 10% (v/v) N-methylimidazole in acetonitrile and 50 mL of 10% (v/v) acetic anhydride in acetonitrile to cap residual surface-bound amines. The capping reaction was allowed to proceed for 2 hours at ambient temperature. The support was then washed well on a glass-fritted funnel with acetonitrile and dried overnight under vacuum. The loading of the dried support was found to be 6.1 moles/gram, as determined spectrophotometrically from the orange DMTr cation released by treatment of the support with 0.1 M p-toluenesulfonic acid in acetonitrile ($A_{498}$, $\epsilon_{498}$=70,000 M$^{-1}$cm$^{-1}$).

Example 6

Figure 17:
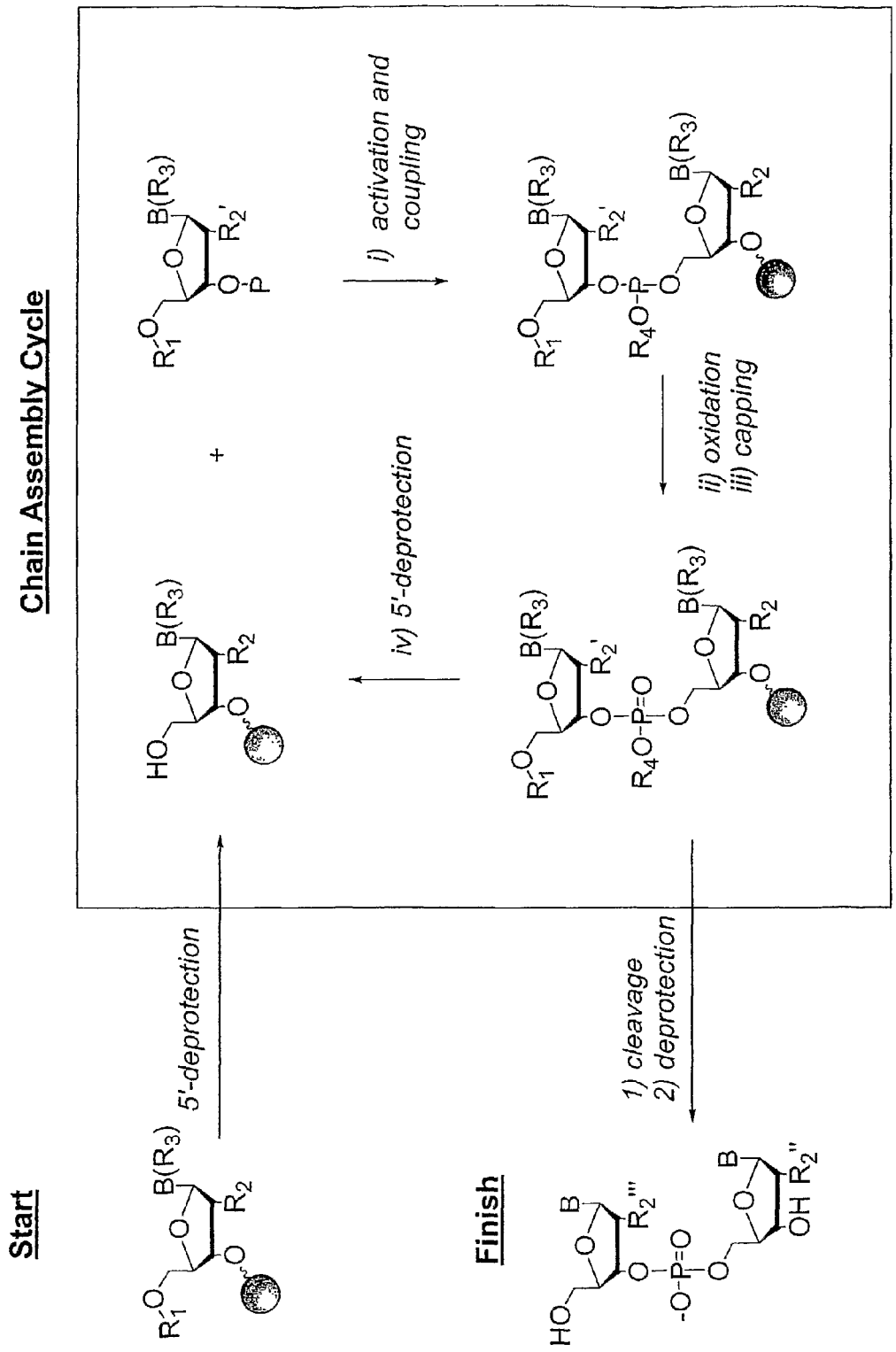

Synthesizing Polynucleotides Comprising a Linker Moiety Covalently Attached to a Levulinyl Moiety Polynucleotides (DNA or RNA) can efficiently be synthesized in a stepwise fashion using the nucleotide addition reaction cycle illustrated in FIG. 17 and well known to those of ordinary skill in the art. The synthesis is preferably carried out as an automated process on an appropriate instrument. Several instruments appropriate for the automated synthesis of polynucleotides are known to those of skill in the art. Typically, each nucleotide is added sequentially (3'- to 5'-direction) to a solid support-bound polynucleotide. The first nucleoside at the 3'-end of the chain is covalently attached to a solid support. The nucleotide precursor—a reactive nucleotide derivative such as a phosphoramidite or H-phosphonate—and an activator such as a tetrazole, for example, 5-ethylthio-1H-tetrazole (although any other suitable activator can be used), are added (step i in FIG. 17) to the couple the second base onto the 5'-end of the first nucleoside. The support is washed and any unreacted 5'-hydroxyl groups are capped with an acylating reagent such as but not limited to acetic anhydride or phenoxyacetic anhydride to yield unreactive 5'-acyl moieties (step ii). The phosphite [P(III)] internucleotide linkage is then oxidized to the more stable and ultimately desired phosphate [P(V)] internucleotide linkage (step iii), using a suitable oxidizing agent such as, for example, t-butyl hydroperoxide or iodine and water. At the end of the nucleotide addition cycle, the 5'-protecting group is cleaved (step iv) using a suitable reagent (for example, 3% dichloroacetic acid in dichloromethane if the protecting group is DMTr, or triethylammonium trihydrogen fluoride, if the protecting group is silyl). The cycle is repeated for each subsequent nucleotide until the desired sequence is obtained. It should be emphasized that although FIG. 17 illustrates a phosphoramidite having an alkoxy protecting group, any suitable group may be used to protect or replace the oxygen of the phosphoramidite moiety. For example, a methyl group, a cyanoethyl group, or a thio derivative can be employed at this position. Further, the incoming activated nucleoside in step i can be a different kind of activated nucleoside, for example, an H-phosphonate, methyl phosphonamidite or a thiophosphoramidite.

Following synthesis, the polynucleotide is cleaved from the support and the various remaining protecting groups are removed. If, for example, a methyl group has been used to protect the phosphorous, it is most preferably removed prior to cleavage from the solid support. This is accomplished utilizing 1 M disodium-2-carbamoyl-2-cyanoethylene-1,1-dithiolate trihydrate in dimethylformamide. Alternatively, if the protecting group on the phosphorous is 2-cyanoethyl, it can be removed concomitantly with cleavage. Cleavage and removal of remaining protecting groups on the nucleoside bases and phosphate linkage is typically performed using concentrated aqueous ammonia or methylamine, initially at room temperature (cleavage) and then at 55-65° C. (deprotection); however, certain combinations of protecting groups can be removed under milder conditions, such as concentrated aqueous ammonia at room temperature or potassium carbonate in methanol.

If the polynucleotide contains ribonucleotide units within its sequence, the protecting groups on any 2'-hydroxyls are retained at this point in the synthetic process. This is necessary because exposure of ribonucleotides bearing a phosphate on the 3'-hydroxyl and containing a free 2'-hydroxyl to the basic conditions of cleavage and deprotection will cause 3'- to 2'-phosphate migration and cyclization, resulting in non-biologically active or truncated products. Two classes of 2'-protecting groups are typically used in polynucleotide synthesis. The first class is composed of silyl ether-containing protecting groups (for example, tert-butyldimethylsilyl [TBDMS] and triisopropylsilyloxymethyl [TOM]). These are removed using fluoride ion in a non- or partially aqueous solvent. The fluoride salts are then removed from the reaction using filtration and/or ethanol precipitation to produce fully deprotected polynucleotide. The second class is composed of orthoester protecting groups (for example, ACE). These groups are removed using mild aqueous acid, and fully deprotected polynucleotide is obtained following lyophilization of the reaction mixture.

For automated procedures, polymeric columns containing the solid support having the initial nucleoside are installed on the synthesizing instrument. Bottles are affixed to the instrument containing all of the necessary ancillary reagents and reactive nucleotide monomers needed for synthesis. Reagents are maintained under a dry inert gas, typically argon, since the monomers are sensitive to both water and oxygen. The instrument is primed so as to fill all lines with each reagent. A synthesis cycle is designed that defines the delivery of the reagents in the proper order according to the synthesis cycle, delivering the reagents in the order specified in FIG. 17. Once a cycle (i.e., the sequence of reagent additions, the amount of each reagent to be added, and the time between steps) is defined, and the support columns are installed, the polynucleotide synthesis is ready to proceed.

For the nucleotide analogs described herein, modification was achieved through three different general methods. The first, which was implemented for sugar and base modifications, as well as for introduction of certain linkers and conjugates, employed modified phosphoramidites in which the modification is pre-existing. An example of such a modification would be species modified at the 2'-position of the sugar ring (for example, 2'-fluoro, 2'-amino, 2'-O-alkyl, etc.), wherein the 2'-protected hydroxyl was replaced with the desired modification. 3'- or 5'-terminal modifications can be similarly introduced (for example, fluorescein and rhodamine derivatives, dabsyl derivatives, acridine derivatives, cholesterol, cyanine derivatives or polyethylene glycol). Certain internucleotide bond modifications may also be introduced via the incoming reactive nucleoside intermediate. Examples of the resultant internucleotide bond modification include but are not limited to methylphosphonates, phosphoramidates, or phosphorodithioates.

A variety of modifiers can be employed using the same or similar cycles. Examples in this class would include, for example, 2-aminopurine, 5-methylcytidine, 5-aminoallyluridine, 2,6-diaminopurine, 2-O-alkylnucleosides, multi-atom spacers, functionalized linkers, 2'-aminonucleosides, 2'-fluoronucleosides, 5-iodouridine, 4-thiouridine, 5-bromouridine, 5-fluorocytidine, 5-fluorouridine, 5-iodouridine, 5-iodocytidine, 5-biotin-thymidine, 5-fluoroscein-thymidine, inosine, pseudouridine, abasic derivatives, nebularine, deazanucleosides, azanucleosides, etc. Often the rest of the steps in the synthesis will remain the same with the exception of modifications that introduce substituents that are labile to standard deprotection conditions. Here modified deprotection conditions are employed that do not affect sensitive substituent as mentioned earlier. Second, certain internucleotide bond modifications require an alteration of the oxidation step to allow for their introduction. Examples in this class include phosphorothioates and phosphorodithioates wherein oxidation with elemental sulfur or another suitable sulfur transfer agent is required.

The following guidelines are provided for synthesis of modified polynucleotides, and can readily be adapted to use on any of the automated synthesizers known in the art.

3' Terminal Modifications

There are several methods for incorporating 3'-modifications. As described previously, the 3'-modification can be attached to a solid support of choice using methods known in the art. Alternatively, the 3'-modification may be available as a phosphoramidite. The phosphoramidite may be coupled to a "universal" support using standard synthesis methods. In this instance, the universal support provides a hydroxyl at which the 3'-terminal modification is created by introduction of the activated phosphoramidite of the desired modification. Alternatively, the 3'-modification may be introduced post-synthetically after the polynucleotide is removed from the solid support. In general, the polynucleotide has been synthesized to incorporate a 3'-terminal reactive functionality, such as amino, thio, or haloalkyl, that reacts with an appropriately activated form of the modification of choice. Examples of such activated forms include but are not limited to N-hydroxysuccinimidyl ester, N-hydroxysulfosuccinimidyl ester, sulfotetrafluorophenyl ester, amino, hydrazine, carbonyl, disulfide, pyridyl disulfide, or haloalkyl. This modification now becomes the 3'-terminus of the polynucleotide. Non-limiting examples of modifications that can be incorporated post-synthetically are fluoresceins, rhodamines, acridines, dabsyl, cyanines, polyethylene glycols, multi-atom hetero- and homo-bifunctional spacers, carbohydrates, fatty acids, steroids, peptides, or polypeptides.

5' Terminal Modifications

There are several methods for incorporating 5'-modifications. For example, a phosphoramidite having the desired 5'-modification can be synthesized and employed in the polynucleotide assembly cycle similar to an unmodified nucleoside phosphoramidite. Alternatively, the 5'-modification may be introduced post-synthetically after the polynucleotide is removed from the solid support. In general, the polynucleotide has been synthesized to incorporate a 5'-terminal reactive functionality, such as amino, thio, or haloalkyl, that reacts with an appropriately activated form of the modification of choice. Examples of such activated forms include but are not limited to N-hydroxysuccinimidyl ester, N-hydroxysulfosuccinimidyl ester, sulfotetrafluorophenyl ester, amino, hydrazine, carbonyl, disulfide, pyridyl disulfide, or haloalkyl. This modification now becomes the 5'-terminus of the polynucleotide. Non-limiting examples of modifications that can be incorporated post-synthetically are fluoresceins, rhodamines, acridines, dabsyl, cyanines, polyethylene glycols, multi-atom hetero- and homo-bifunctional spacers, carbohydrates, fatty acids, steroids, peptides, or polypeptides.

Internal Modifications

Modifications internal to the polynucleotide sequence are introduced either during polynucleotide chain assembly, or post-synthetically. In general, such modifications must contain both a protected hydroxyl (the same as or similar to that found in a normal nucleotide) and an activated phosphorous. These are required so that incorporation of the modification allows for further elaboration of the polynucleotide chain. Both nucleoside and non-nucleoside derivatives may be used, and the derivative may carry the modification directly (for incorporation using the previously describe polynucleotide synthesis cycle) or a reactive functionality that may be used to introduce the desired modification post-synthetically (as described for 3'- and 5'-terminal modifications).

For certain modifications, the steps of the synthesis cycle need to be modified somewhat from the conditions useful with standard nucleosides in order to provide high efficiency reactions. For example, for polynucleotides in which the 3'-terminus is an "inverse dT" (wherein the first base is thymidine attached to the solid support through the 5'-hydroxyl, and the first coupling results in a 3'-3' linkage), the 3'-hydroxyl deprotection and coupling occur more slowly than normal, so that the deprotection and coupling times must be increased. Some 5'- and internal modifications also require extended coupling times. Examples include certain phosphoramidite derivatives of cholesterol, cyanine fluorophores, biotin, dabsyl, amino linkers, thio linkers, spacers, polyethylene glycols, chemical phosphorylating reagents, and photocleavable linkers.

Thioates

Polynucleotides having one or more thioate moieties, such as phosphorothioate linkages, are prepared in accordance with the synthesis cycle described above and illustrated in FIG. 17. However, in place of the normal oxidation step to convert the phosphite linkage to a phosphate linkage, elemental sulfur or another sulfurizing agent is used to oxidize the phosphite to a phosphorothioate linkage.

Figure 18:
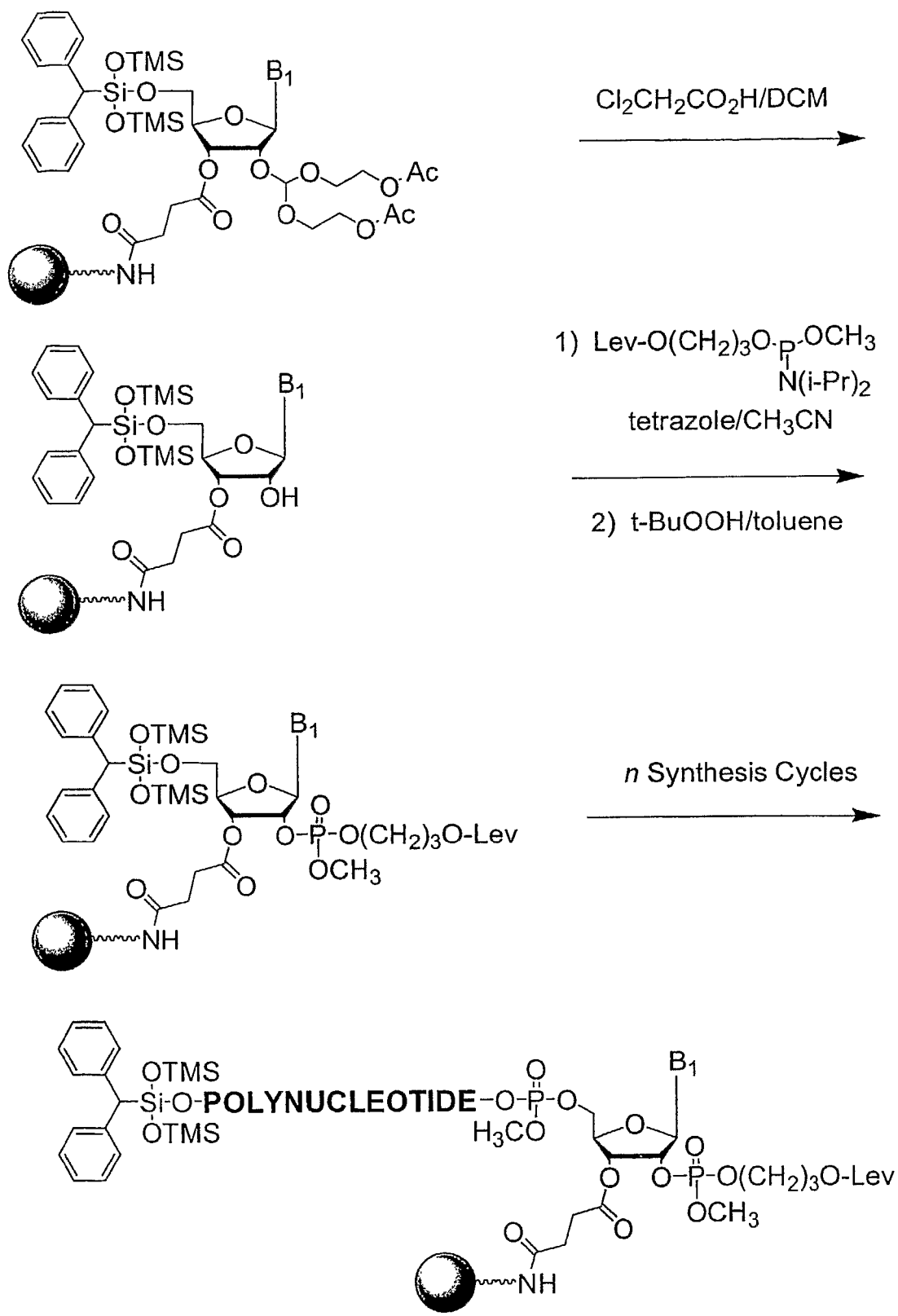
FIG. 18 is a schematic representation of the synthesis of one embodiment of a polynucleotide on a solid support, wherein the polynucleotide comprises a linker protected by a levulinyl moiety at the 2'-position.

Synthesis of a Polynucleotide Comprising a Linker Covalently Attached to a Levulinyl Moiety Using a Linker Phosphoramidite Compositions of the type described in Example 1 can be used to incorporate a linker covalently attached to a levulinyl moiety into either the 5'-terminus or the 3'-terminus of a polynucleotide. Incorporation at the 5'-terminus is accomplished as described above. Incorporation at the 3'-terminus can be accomplished as follows. A solid support having an appropriately protected ribonucleoside covalently appended thereto is prepared as described previously, either through a dicarboxylic acid linkage or by virtue of the reaction of a phosphoramidite derivative with a universal support. The 2'- and 5'-protecting groups are chosen such that the 2'-protecting group may be removed without concomitant removal of the 5'-protecting group (for example, 5'-DMTr and 2'-TBDMS, or 5'-silyl and 2'-ACE). The 2'-protecting group of the support-bound nucleoside is cleaved with an appropriate reagent (for example, fluoride ion for 2'-TBDMS or 3% dichloroacetic acid in DCM for 2'-ACE), resulting in a free 2'-hydroxyl. This hydroxyl can then be specifically reacted with the linker phosphoramidite using a standard synthesis cycle to install the linker covalently attached to a levulinyl moiety. Since the levulinyl moiety is stable to the conditions required for deprotection of the 5'-hydroxyl, the assembly of the desired polynucleotide synthesis can then be carried out. This process is depicted in FIG. 18.

Synthesis of a Polynucleotide Comprising a Linker Covalently Attached to a Levulinyl Moiety using a Nucleoside Phosphoramidite Comprising a Linker Protected by a Levulinyl Moiety at the 2'-Position of a Ribosyl Moiety Compositions of the type described in Examples 2 and 3 can be used to incorporate a linker covalently attached to a levulinyl moiety into any sequence position of a polynucleotide using the methods described above.

Synthesis of a Polynucleotide Comprising a Linker Covalently Attached to a Levulinyl Moiety using a Nucleoside Phosphoramidite Comprising a Linker Protected by a Levulinyl Moiety at the Nitrogenous Base and having a 5'-Silyl Protecting Group Compositions of the type described in Example 4 can be used to incorporate a linker covalently attached to a levulinyl moiety into any sequence position of a polynucleotide using the methods described above.

Synthesis of a Polynucleotide Comprising a Linker Covalently Attached to a Levulinyl Moiety using a Solid Support Comprising a Linker Protected by a Levulinyl Moiety Compositions of the type described in Example 5 can be used to incorporate a linker covalently attached to a levulinyl moiety into the 3'-terminal position of a polynucleotide using the methods described above.

Example 7

Figure 19:
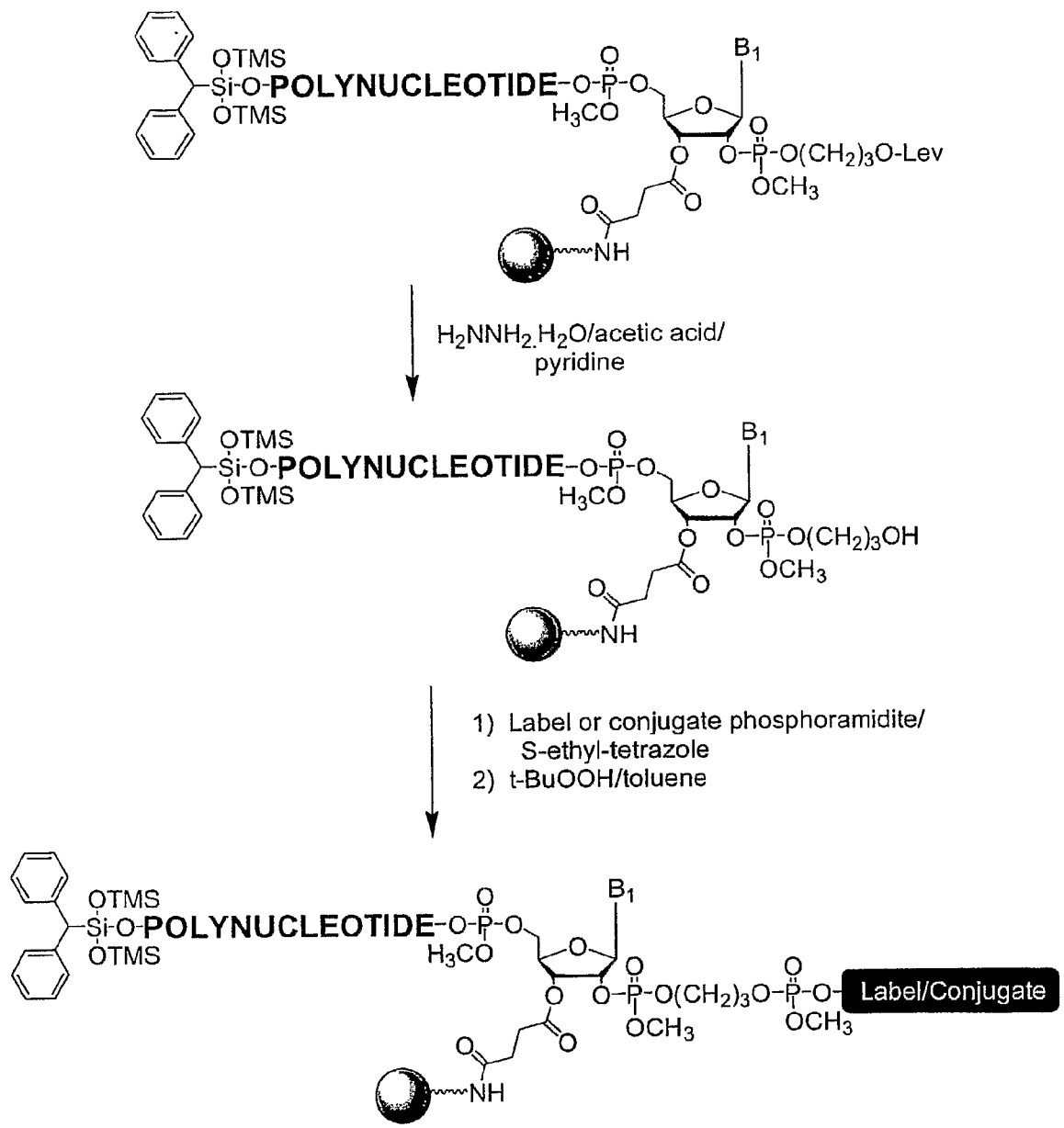
FIG. 19 is a schematic representation of the synthesis of one embodiment of a polynucleotide comprising a label or conjugate at the 3' terminus on a solid support, using a linker protected by a levulinyl moiety.

Attachment of a Label or Conjugate to a Polynucleotide Comprising a Linker Covalently Attached to a Levulinyl Moiety As described previously, following assembly of the desired sequence but prior to removal of the 5'-terminal protecting group, the polynucleotide exists in its fully protected form covalently attached to a solid support. The levulinyl moiety on the incorporated linker can be selectively removed under neutral conditions by using a mixture of hydrazine hydrate, pyridine and acetic acid. Briefly, a hydrazine cocktail is prepared, in, for example, a volume of 3 mL. The cocktail includes 47 microliters of hydrazine monohydrate, 1772 microliters of pyridine, and 1181 microliters of acetic acid. The pH of this mixture is 6-7. The support-bound polynucleotide of interest comprising the linker covalently attached to the levulinyl moiety is treated with the hydrazine cocktail for about 5-20 minutes at room temperature, preferably 5-10 minutes at room temperature. The hydrazine mixture is drained form the support, which is then rinsed thrice with acetonitrile. The result of the hydrazine treatment is a polynucleotide comprising a linker with a reactive functionality. Once the levulinyl moiety is removed, the linker can be used to attach any moiety of interest, for example, a conjugate or a label, as long as the conjugate or label comprises a group that can be covalently attached to the linker. Preferably, the reactive functionality on the linker is a free hydroxyl and the conjugate or label comprises a phosphoramidite. In such case the labeling can be performed on the automated instrument using the same or similar cycle to that described previously for normal nucleoside phosphoramidites. This procedure (see FIG. 19) takes advantage of the highly efficient chemistry inherent in phosphoramidite reactions as well as the positive aspects of solid support-based synthesis (i.e., use of excess solution phase reagents to drive reaction to completion, removal of excess reagents by washing).

Following label/conjugate incorporation, the 5'-protecting group is removed from the support-bound polynucleotide. The modified polynucleotide is then cleaved and deprotected using conditions suitable to the incorporated modification as described previously.

It should be noted that those skilled in the art would readily understand that the above procedure could be used to incorporate more than a single label into a polynucleotide. The number of labels incorporated is controlled by the number of linkers covalently attached to a levulinyl moiety present within the sequence. It may be necessary to adjust the incoming quantity of label or conjugate in this case to maintain a suitably large excess of label or conjugate over linkers.

Figure 20:
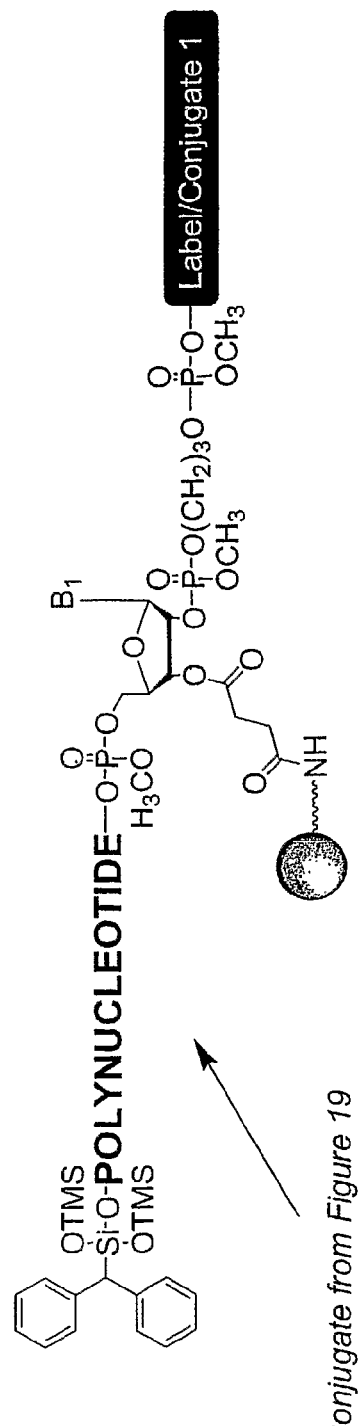
FIG. 20 is a schematic representation of the synthesis of one embodiment of a polynucleotide comprising a label or conjugate at the 3' terminus and at the 5' terminus on a solid support.
Figure 20:
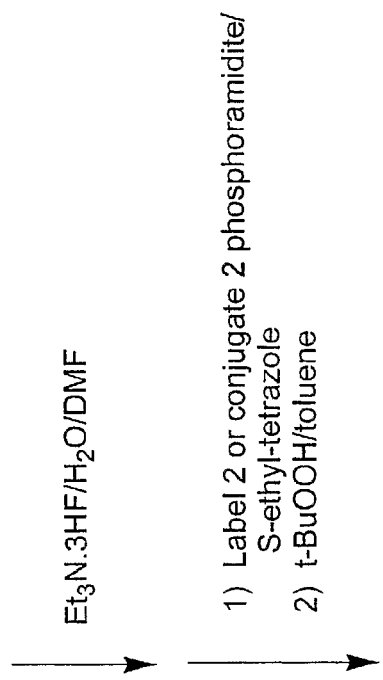
Figure 20:
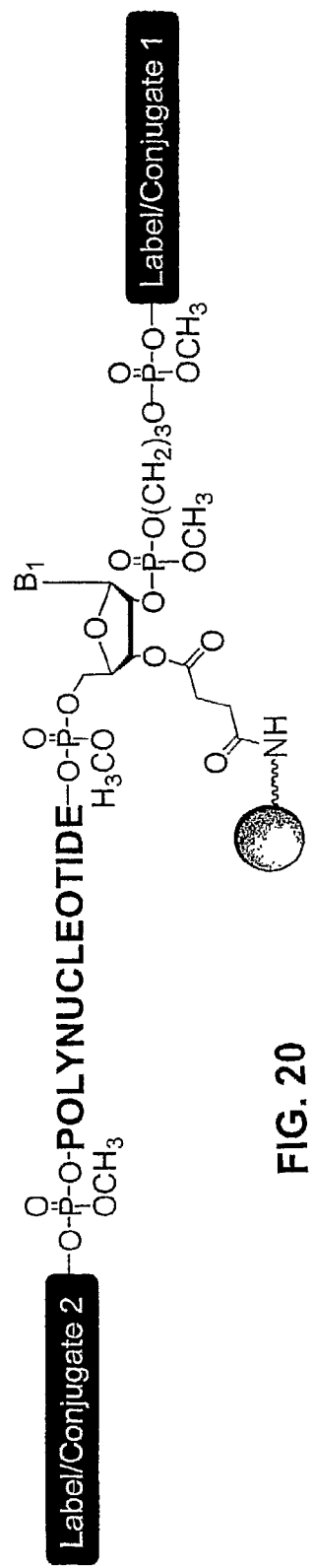

A particular advantage of the compositions and methods described herein is the simplification of efficiently preparing polynucleotides with two different labels or conjugates or a combination of each. A variety of applications (for example, molecular beacon technology) exist in which two different labels must be incorporated into precise sequence locations in a polynucleotide. Similarly, it is frequently necessary to incorporate both a label and a conjugate into a polynucleotide (for example, a biotin for polynucleotide immobilization and a fluorophore for visualization). Those skilled in the art will understand that the support-bound polynucleotide may be reacted specifically with one label/conjugate at either the 5'-hydroxyl or at the linker (due to the orthogonality of the 5'-hydroxyl protecting group and the levulinyl moiety), and subsequently with the other label/conjugate at the unmodified position (FIG. 20).

General Procedure for the Attachment of a Label or Conjugate to a Polyribonucleotide Comprising a Linker Covalently Attached to a Levulinyl Moiety Polyribonucleotides are synthesized using 5'-silyl-2'-ACE phosphoramidites as described in Scaringe, S. A., Kitchen, D., Kaiser, R., and Marshall, W. M. (2004) "Preparation of 5'-Silyl-2'-Orthoester Ribonucleosides for the Use in Oligoribonucleotide Synthesis" *Current Protocols in Nucleic Acid Chemistry* vol. 1. (Beaucage, S. L., ed; New York: John Wiley & Sons, Inc.), 2.10.11-15; and Hartsel, S. A., Kitchen, D. E., Scaringe, S. A. and Marshall, W. S. (2005) "RNA Oligonucleotide Synthesis Via 5'-Silyl-2'-Orthoester Chemistry" *Methods in Molecular Biology*, vol. 288 (Oligonucleotide Synthesis: Methods and Applications) (P. Herdewijn, ed.), 33-49. Levulinyl-modified amidites as described in the examples above (0.1 M in anhydrous acetonitrile) are coupled to the growing polyribonucleotide chain for 3 minutes using 5-ethylthio-1H-tetrazole (0.5 M in anhydrous acetonitrile) as the activator. Whenever possible, the levulinyl moiety is removed after the synthesis full-length polyribonucleotide is completed in order to maximize the integrity of the label or the conjugate. The levulinyl moiety is removed by treatment of the immobilized oligoribonucleotide with 0.32 M hydrazine monohydrate in 3:2 (v/v) pyridine:glacial acetic acid for 5 minutes. The hydrazine solution is washed away by delivery of acetonitrile to the synthesis column for 3 minutes and a phosphoramidite derivative of the desired label or conjugate is then coupled to the hydroxyl-terminated linker according to the manufacturer's specifications. Phosphate deprotection is effected by using disodium 2-carbamoyl-2-cyanoethylene-1,1-dithiolate trihydrate in DMF, and the crude oligonucleotide is typically cleaved from the support and fully deprotected using 40% (w/v) aqueous methylamine as described in the above reference (Hartsel et al.). Alternative cleavage and deprotection may need to be utilized depending upon the lability of the label or conjugate to the methylamine reagent.

Synthesis of a Polynucleotide Labeled at an Internal Nucleotide Position using a Nucleotide Comprising a Linker Covalently Attached to a Levulinyl Moiety Polynucleotide sequence:

```
                                          (SEQ. ID NO.: 1)
5'-CAGAUCGAAUGAC 77(Fl) CGCUUGUCAdT-3'
```

(Note: "77(FI)" indicates the position of incorporation of the linker covalently attached to a levulinyl moiety, and that a fluorescein label has been attached to the linker)

Figure 21:
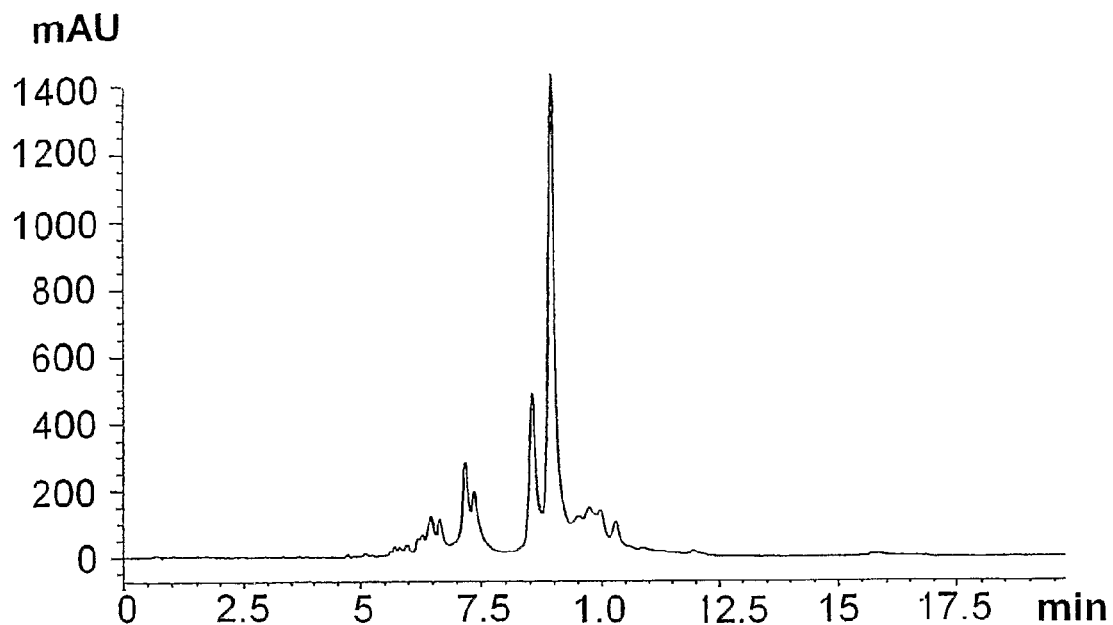
FIG. 21 is a reverse phase HPLC chromatogram of a crude labeled polynucleotide prepared using the methods of the invention. Compound 77 is used to introduce the linker to which the label is attached. The two major peaks at 8.6 and 9.0 minutes correspond to the two positional isomers of the label attached to the polynucleotide. The polynucleotide sequence is given in the text.
Figure 22:
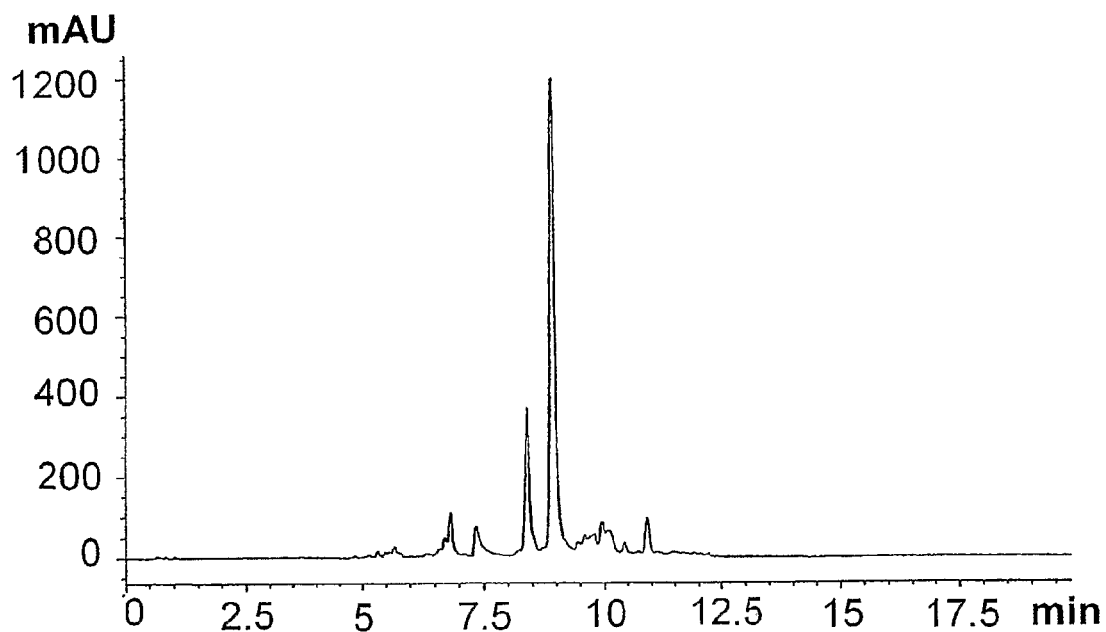
FIG. 22 is a reverse phase HPLC chromatogram of a crude labeled polynucleotide prepared using the methods of the invention. Compound 35 is used to introduce the linker to which the label is attached. The two major peaks at 8.4 and 8.8 minutes correspond to the two positional isomers of the label attached to the polynucleotide. The polynucleotide sequence is given in Table I.
Figure 23:
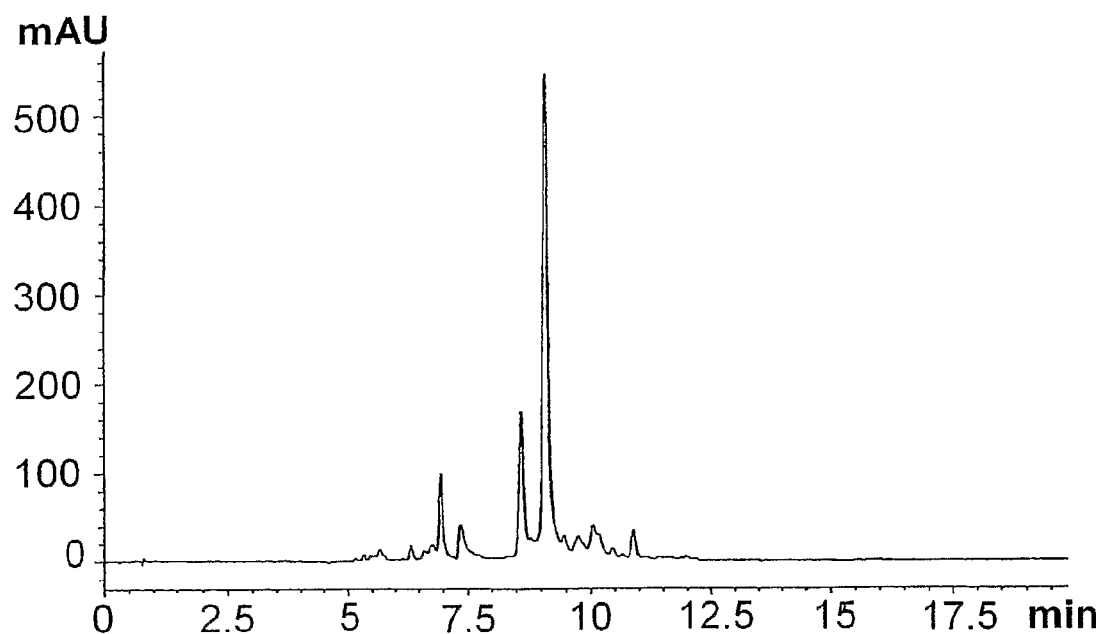
FIG. 23 is a reverse phase HPLC chromatogram of a crude labeled polynucleotide prepared using the methods of the invention. Compound 77 is used to introduce the linker to which the label is attached. The two major peaks at 8.6 and 9.2 minutes correspond to the two positional isomers of the label attached to the polynucleotide. The polynucleotide sequence is given in Table I.
Figure 24:
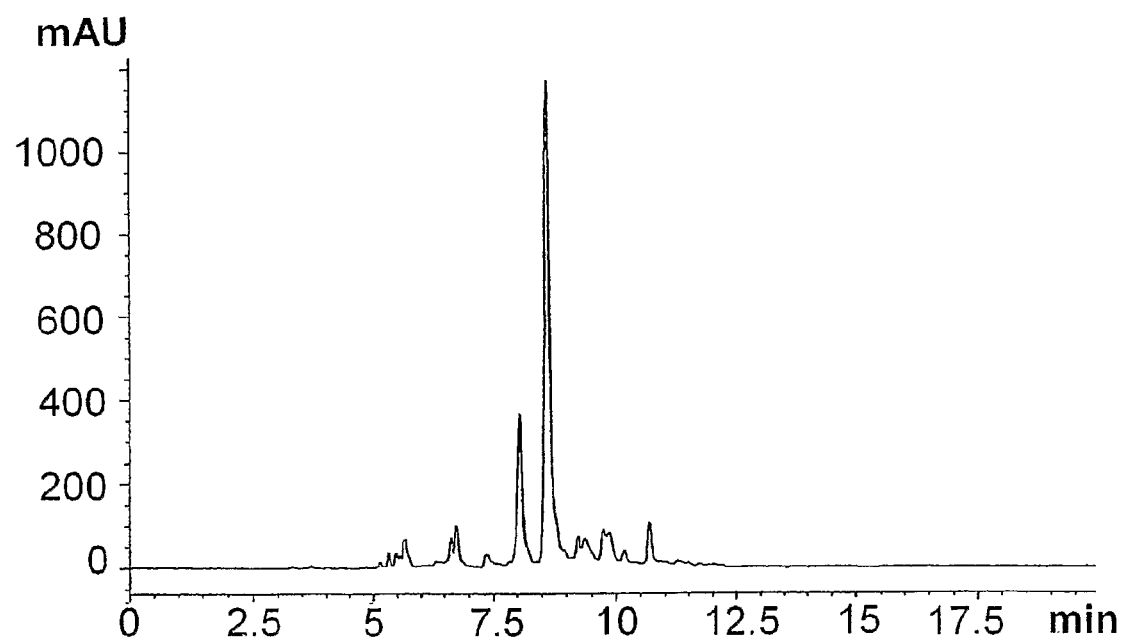
FIG. 24 is a reverse phase HPLC chromatogram of a crude labeled polynucleotide prepared using the methods of the invention. Compound 11 is used to introduce the linker to which the label is attached. The two major peaks at 8.0 and 8.6 minutes correspond to the two positional isomers of the label attached to the polynucleotide. The polynucleotide sequence is given in Table I.
Figure 25:
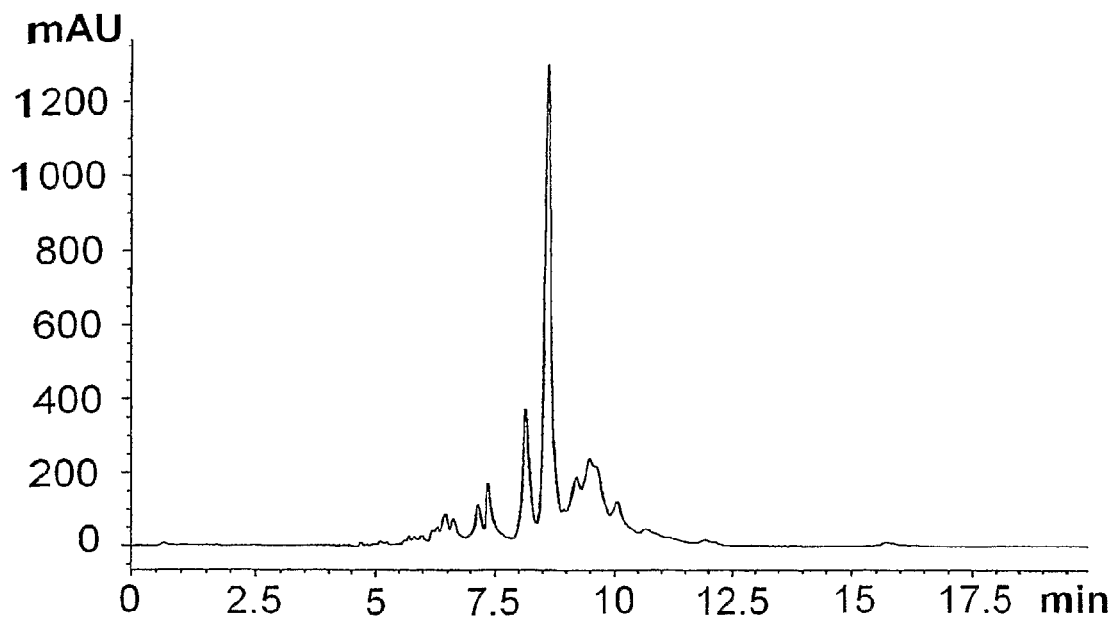
FIG. 25 is a reverse phase HPLC chromatogram of a crude labeled polynucleotide prepared using the methods of the invention. Compound 11 is used to introduce the linker to which the label is attached. The two major peaks at 8.2 and 8.7 minutes correspond to the two positional isomers of the label attached to the polynucleotide. The polynucleotide sequence is given in Table I.

The above sequence was programmed into the automated synthesis instrument and it was synthesized using the standard cycle in the 3' to 5' direction on a 0.2 µmole dT column. Compound 77 was used to introduce a linker covalently attached to a levulinyl moiety at position 11 in the sequence (counted from the 3'-terminus), and was coupled for 3 minutes as described above. The rest of the polyribonucleotide sequence was synthesized using the standard cycle. After the coupling of the last nucleotide, the 5'-BZH group was cleaved, the column was removed from the instrument, and the resulting 5'-OH was manually capped with a solution of 5% (v/v) acetic anhydride and 5% (v/v) N-methylimidazole in acetonitrile for 10 minutes. Manual treatment of the immobilized oligonucleotide with 0.32 M hydrazine monohydrate in 3:2 (v/v) pyridine:glacial acetic acid for 5 minutes removed the levulinyl group from the linker. The column was re-installed on the instrument and the support was washed with acetonitrile for 3 minutes to remove residual hydrazine solution. Commercial (5 and 6)-carboxyfluorescein-aminohexyl amidite (0.1 M in anhydrous acetonitrile) was coupled to the linker for 10 minutes on the instrument. Standard oxidation and capping steps were performed. The phosphate protecting groups were removed from the immobilized labeled polyribonucleotide by treatment with disodium 2-carbamoyl-2-cyanoethylene-1,1-dithiolate trihydrate in DMF for 10 minutes. The support was then washed extensively with water, and the labeled polyribonucleotide was cleaved from the support with 40% (w/v) aqueous methylamine for 5 minutes. Incubation of the methylamine solution at 60° C. for 11 minutes effected removal of the base-protecting groups. The sample was cooled to room temperature and lyophilized to obtain the crude polyribonucleotide (229 mmoles). The sample was suspended in water (1.0 mL) and a 50 µL aliquot was dried down and incubated in 100 µL of 300 mM acetic acid-TEMED buffer, pH 3.8, at 60° C. for 35 minutes to remove the orthoester protecting groups from the 2'-hydroxyls. This sample was analyzed by reverse phase HPLC (C18 column; linear gradient of acetonitrile in 0.1 M triethylammonium acetate, pH 7.0; flow rate 1.0 mL/minute; detector at 260 nm) and MALDI-TOF mass spectrometry. The chromatogram of the crude labeled polyribonucleotide is shown in FIG. 21. Mass spectrometric data: calculated 8551, observed 8551.

Table I provides further examples of polynucleotides labeled at an internal nucleotide position using the above-described general procedure. Each entry was analyzed by reverse phase HPLC and MALDI-TOF mass spectrometry. HPLC chromatograms of the crude labeled polyribonucleotides are provided in FIGS. 22-33.

Synthesis of a Polynucleotide Labeled at an Internal Nucleotide Position and a Terminal Nucleotide Position with Two Different Labels Polynucleotide sequence:

```
5'-(Fl) dAUdA 35(TAM)-3'
```

(Note: "35(TAM)" indicates the position of incorporation of the linker covalently attached to a levulinyl moiety, and that a TAMRA label has been attached to the linker. (FI) at the 5'-terminus indicates a fluorescein label attached to the 5'-hydroxyl).

The above sequence was programmed into the automated synthesis instrument and it was synthesized using the standard cycle in the 3' to 5' direction on a 1.0 mmole universal support column. Compound 35 was used to introduce the linker covalently attached to a levulinyl moiety at position 1 (the 3'-terminus) in the sequence, and was coupled for 3 minutes as described above. The rest of the polyribonucleotide sequence was synthesized using the standard cycle. After the coupling of the last nucleotide, the 5'-BZH group was cleaved and commercial (5 and 6)-carboxyfluorescein-aminohexyl amidite (0.1 M in anhydrous acetonitrile) was coupled to the linker for 10 minutes on the instrument. Standard oxidation and capping steps were performed. The column was removed from the instrument. Manual treatment of the immobilized oligonucleotide with 0.32 M hydrazine monohydrate in 3:2 (v/v) pyridine:glacial acetic acid for 5 minutes removed the levulinyl group from the linker. The column was re-installed on the instrument and the support was washed with acetonitrile for 3 minutes to remove residual hydrazine solution. The column was again removed from the instrument and commercial TAMRA-amidite (0.1 M in anhydrous acetonitrile) was coupled to the linker for 10 minutes. The column was reinstalled on the instrument and standard oxidation and capping steps were performed. The phosphate protecting groups were removed from the immobilized labeled polyribonucleotide by treatment with disodium 2-carbamoyl-2-cyanoethylene-1,1-dithiolate trihydrate in DMF for 10 minutes. The support was then washed extensively with water, and the labeled polyribonucleotide was cleaved from the support with 1:3 (v/v) tert-butylamine:water for 1 hour. Incubation of the tert-butylamine solution at 60° C. for 5 hours effected removal of the base-protecting groups without concomitant damage to the TAMRA chromophore. The sample was cooled to room temperature and lyophilized to obtain the crude polyribonucleotide. The sample was suspended in water (1.0 mL) and a 50 mL aliquot was dried down and incubated in 100 mL of 300 mM acetic acid-TEMED buffer, pH 3.8, at 60° C. for 35 minutes to remove the orthoester protecting groups from the 2'-hydroxyls. This sample was analyzed by reverse phase HPLC (C18 column; linear gradient of acetonitrile in 0.1 M triethylammonium acetate, pH 7.0; flow rate 1.0 mL/minute; detector at 260 nm) and MALDI-TOF mass spectrometry. The chromatogram of the crude labeled polyribonucleotide is shown in FIG. 34. Mass spectrometric data: calculated 2457, observed 2457.

A similar procedure was used to incorporate a fluorescein label at position 45 and a Cy3 label at the 5'-terminus in the following polynucleotide:

Polynucleotide sequence:

(SEQ. ID NO.: 2)
5'-(Cy3) CCGGUAUAACCUCAAUAAUA 77(Fl) GGUUUGAGGGUGU

CUACCAGGAACCGUAAAAUCCUGAUUACCGG-3'

(Note: "77(Fl)" indicates the position of incorporation of the linker covalently attached to a levulinyl moiety, and that a fluorescein label has been attached to the linker. (Cy3) at the 5'-terminus indicates a Cy3 label attached to the 5'-hydroxyl)

The chromatogram of the crude labeled polyribonucleotide is shown in FIG. 35. Mass spectrometric data: calculated 21989, observed 21988.

Synthesis of a Polynucleotide Labeled at Two Internal Nucleotide Positions with Two Different Labels Polynucleotide sequence:

(SEQ. ID NO.: 3)
5'-AA 77(Fl) GCU 35(Dab) UUGGACUACGAUAGG CAUUA-3'

(Note: "35(Dab)" indicates the position of incorporation of a first linker covalently attached to a levulinyl moiety, and that a dabcyl label has been attached to the linker. "77(Fl)" indicates the position of incorporation of a second linker covalently attached to a levulinyl moiety, and that a fluorescein label has been attached to the linker.)

The above sequence was programmed into the automated synthesis instrument and it was synthesized using the standard cycle in the 3' to 5' direction on a 0.4 μmole rA column. Compound 35 was used to introduce a linker covalently attached to a levulinyl moiety at position 21 in the sequence (counted from the 3'-terminus), and was coupled for 3 minutes as described above. The next portion of the polyribonucleotide sequence (positions 22-24) was synthesized using the standard cycle. At this point, the 5'-BZH group was retained and the column was removed from the instrument. Manual treatment of the immobilized oligonucleotide with 0.32 M hydrazine monohydrate in 3:2 (v/v) pyridine:glacial acetic acid for 5 minutes removed the levulinyl group from the linker on compound 35. The column was re-installed on the instrument and the support was washed with acetonitrile for 3 minutes to remove residual hydrazine solution. Commercial dabcyl-amidite (0.1 M in anhydrous acetonitrile) was coupled to the linker for 10 minutes on the instrument. Standard oxidation and capping steps were performed. Compound 77 was then used to attach a linker covalently attached to a levulinyl moiety at position 25 in the sequence (counted from the 3'-terminus), and was coupled for 3 minutes as described above. The rest of the polynucleotide sequence was synthesized using the standard cycle. After the coupling of the last nucleotide, the 5'-BZH group was cleaved, the column was removed from the instrument, and the resulting 5'-OH was manually capped with a solution of 5% (v/v) acetic anhydride and 5% (v/v) N-methylimidazole in acetonitrile for 10 minutes. Manual treatment of the immobilized oligonucleotide with 0.32 M hydrazine monohydrate in 3:2 (v/v) pyridine:glacial acetic acid for 5 minutes removed the levulinyl group from the linker on compound 77. The column was re-installed on the instrument and the support was washed with acetonitrile for 3 minutes to remove residual hydrazine solution. Commercial (5 and 6)-carboxyfluorescein-aminohexyl amidite (0.1 M in anhydrous acetonitrile) was coupled to the linker for 10 minutes on the instrument. Standard oxidation and capping steps were performed. The phosphate protecting groups were removed from the immobilized labeled polyribonucleotide by treatment with disodium 2-carbamoyl-2-cyanoethylene-1,1-dithiolate trihydrate in DMF for 10 minutes. The support was then washed extensively with water, and the labeled polyribonucleotide was cleaved from the support with 40% (w/v) aqueous methylamine for 5 minutes. Incubation of the methylamine solution at 60° C. for 11 minutes effected removal of the base-protecting groups. The sample was cooled to room temperature and lyophilized to obtain the crude polyribonucleotide (220 mmoles). The sample was suspended in water (1.0 mL) and a 50 μL aliquot was dried down and incubated in 100 μL of 300 mM acetic acid-TEMED buffer, pH 3.8, at 60° C. for 35 minutes to remove the orthoester protecting groups from the 2'-hydroxyls. This sample was analyzed by reverse phase HPLC (C18 column; linear gradient of acetonitrile in 0.1 M triethylammonium acetate, pH 7.0; flow rate 1.0 mL/minute; detector at 260 nm) and MALDI-TOF mass spectrometry. The chromatogram of the crude labeled polyribonucleotide is shown in FIG. 36. Mass spectrometric data: calculated 9836, observed 9860.

A similar procedure was used to incorporate a Cy3 label at position 3 and a fluorescein label at position 12 in the following polynucleotide:

Polynucleotide sequence:

(SEQ. ID NO.: 4)
5'-CCAUUUGAUACACUA 77(Fl) UUAUCAAA 77(Cy3) GG-3'

(Note: "77(Cy3)" indicates the position of incorporation of a first linker covalently attached to a levulinyl moiety, and that a Cy3 label has been attached to the linker. "77(Fl)" indicates the position of incorporation of a second linker covalently attached to a levulinyl moiety, and that a fluorescein label has been attached to the linker.)

The chromatogram of the crude labeled polyribonucleotide is shown in FIG. 37. Mass spectrometric data: calculated 9761, observed 9761.

Synthesis of a Polynucleotide Labeled at the 3'-Terminal Nucleotide Position using a Solid Support Comprising a Linker Covalently Attached to a Levulinyl Moiety Polynucleotide sequence:

(SEQ. ID NO.: 5)
5'-AGAUCGAAUGACUACGCUUGUCAU (Cy3)-3'

(Note: "(Cy3)" indicates a linker covalently attached to a levulinyl moiety and that a Cy3 label has been attached to the linker.)

The above sequence was programmed into the automated synthesis instrument and it was synthesized using the standard cycle in the 3' to 5' direction on a 0.2 μmole column containing compound 83 as the synthesis support, which was used to introduce a linker covalently attached to a levulinyl moiety at position 1 in the sequence (the 3'-terminus). After the coupling of the last nucleotide, the 5'-BZH group was retained, and the column was removed from the instrument. Manual treatment of the immobilized oligonucleotide with 0.32 M hydrazine monohydrate in 3:2 (v/v) pyridine:glacial acetic acid for 10 minutes removed the levulinyl group from the linker on compound 83. The column was re-installed on the instrument and the support was washed with acetonitrile for 3 minutes to remove residual hydrazine solution. Commercial Cy3 amidite (0.1 M in anhydrous acetonitrile) was coupled to the linker for 10 minutes on the instrument. Standard oxidation and capping steps were performed. The phosphate protecting groups were removed from the immobilized labeled polyribonucleotide by treatment with disodium 2-carbamoyl-2-cyanoethylene-1,1-dithiolate trihydrate in DMF for 10 minutes. The support was then washed extensively with water, and the labeled polyribonucleotide was cleaved from the support with 40% (w/v) aqueous methylamine for 5 minutes. Incubation of the methylamine solution at 60° C. for 11 minutes effected removal of the base-protecting groups. The sample was cooled to room temperature and lyoplilized to obtain the crude polyribonucleotide (160 mmoles). The sample was suspended in water (1.0 mL) and a 50 µL aliquot was dried down and incubated in 100 µL of 300 mM acetic acid-TEMED buffer, pH 3.8, at 60° C. for 35 minutes to remove the orthoester protecting groups from the 2'-hydroxyls. This sample was analyzed by reverse phase HPLC (C18 column; linear gradient of acetonitrile in 0.1 M triethylammonium acetate, pH 7.0; flow rate 1.0 mL/minute; detector at 260 nm) and MALDI-TOF mass spectrometry. The chromatogram of the crude labeled polyribonucleotide is shown in FIG. 38. Mass spectrometric data: calculated 8341, observed 8336.

Example 8

Preparation of Polynucleotide Duplexes having one or more Labels or Conjugates to one or more Linkers Numerous applications of polynucleotides require that the polynucleotides be present in a double stranded form, or duplex. Such duplexes may comprise solely DNA, solely RNA, or mixtures of both, and are formed predominantly by hydrogen bonding between Watson-Crick base pairs (adenine with thymine or uracil and guanine with cytosine). Furthermore, the polynucleotides may contain various nucleoside and non-nucleoside analogs within their sequences. Such duplexes have been prepared by mixing equimolar amounts of each single strand comprising the duplex, optionally warming the mixture to eliminate any non-productive secondary structures in the single strands, and then slowly cooling the mixture to room temperature or below. Often the extent of duplex formation is assessed using non-denaturing polyacrylamide gel electrophoresis; this technique may also be used to purify duplexed polynucleotides away from the component single strands.

The labeled/conjugated polynucleotides of this invention have been used to form duplexes in the manner described above. Either or both of the component strands may be labeled or conjugated.

A particular type of duplex is the stem-loop hairpin. This is a single strand that, upon heating and cooling, forms a stable duplex between the ends of the polynucleotide (the stem) and remains single stranded in the region spanning the duplex (the loop). The labeled/conjugated polynucleotides of this invention have been used to form stem-loop hairpins in the manner described above.

Although the invention has been described and has been illustrated in connection with certain specific or preferred inventive embodiments, it will be understood by those of skill in the art that the invention is capable of many further modifications. This application is intended to cover any and all variations, uses, or adaptations of the invention that follow, in general, the principles of the invention and include departures from the disclosure that come within known or customary practice within the art and as may be applied to the essential features described in this application and in the scope of the appended claims.

TABLE I

Examples of polyribonucleotides labeled at an internal nucleotide position prepared using the methods and compositions of the invention.

| Polyribonucleotide Sequence | Label | MALDI-TOF Data | HPLC Chromatogram |
|---|---|---|---|
| 5'-GAUC 35(Fl) AUCGdT-3' (SEQ. ID NO.: 6) | (5 and 6)-carboxyfluorescein-aminohexyl amidite | calculated 3826 observed 3826 | FIG. 22 |
| 5'-GAUC 77(Fl) AUCGdT-3' (SEQ. ID NO.: 7) | (5 and 6)-carboxyfluorescein-aminohexyl amidite | calculated 3754 observed 3755 | FIG. 23 |
| 5'-GAUC 11(Fl) AUCGdT-3' (SEQ. ID NO.: 8) | (5 and 6)-carboxyfluorescein-aminohexyl amidite | calculated 3725 observed 3727 | FIG. 24 |
| 5'-CAGAUCGAAUGACU 11(Fl) CGCUUG UCAdT-3' (SEQ. ID NO. 9) | (5 and 6)-carboxyfluorescein-aminohexyl amidite | calculated 8522 observed 8524 | FIG. 25 |
| 5'-CAGAUCGAAUGACU 35(Fl) CGCUUGUCAdT-3' (SEQ. ID NO.: 10) | (5 and 6)-carboxyfluorescein-aminohexyl amidite | calculated 8623 observed 8628 | FIG. 26 |
| 5'-GACGUACCU 35(Fl)-3' (SEQ. ID NO.: 11) | (5 and 6)-carboxyfluorescein-aminohexyl amidite | calculated 3827 observed 3828 | FIG. 27 |

TABLE I-continued

Examples of polyribonucleotides labeled at an internal nucleotide position prepared using the methods and compositions of the invention.

| Polyribonucleotide Sequence | Label | MALDI-TOF Data | HPLC Chromatogram |
|---|---|---|---|
| 5'-G 77(Cy3) AGCGCUUCCCCGAUGAGAACUUUU-3' (SEQ. ID NO.: 12) | Cy3 amidite | calculated 9190<br>observed 9187 | FIG. 28 |
| 5'-GGAGCGCUUCCCCGAUGAGAACUU 77(Cy3)-3' (SEQ. ID NO.: 13) | Cy3 amidite | calculated 9190<br>observed 9189 | FIG. 29 |
| 5'-PO$_4$-A 35(Cy3)-3' | Cy5 amidite | calculated 1355<br>observed 1352 | FIG. 30 |
| 5'-AGCACCGUAAAGACG 17(Cy3)-3' (SEQ. ID NO.: 14) | Cy3 amidite | calculated 5678<br>observed 5679 | FIG. 31 |
| 5'-AGCACCGUAAAGACG 17(Cy5)-3' (SEQ. ID NO.: 15) | Cy5 amidite | calculated 5678<br>observed 5679 | FIG. 32 |
| 5'-UAGC 60(F1) AGCU-3' (SEQ. ID NO.: 16) | 6-carboxyfluorescein-aminohexyl amidite | calculated 3507<br>observed 3517 | FIG. 33 |

The number in bold print in each polyribonucleotide sequence refers to the compositions described in Examples 2, 3, or 4 in the text. "PO4" represents a chemically added phosphate moiety. Polynucleotides labeled at the 3'-terminus were prepared using a universal support.

---

What is claimed is:

1. A composition, comprising:

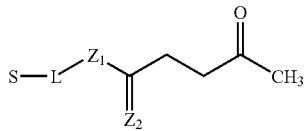

wherein L comprises a linker; $Z_1$ is an oxygen or a sulfur; $Z_2$ is an oxygen or a sulfur; and S comprises a solid support useful for the synthesis of nucleic acids, wherein the linker is attached to S through a covalent linkage, and the linker comprises a functional group through which the linker can attach to a polynucleotide, and the linker further comprises at least one of an alkane, an alkene, a polyether, a polyalcohol, a polyester, a polyamine, a polyalkylamine, a polyphosphodiester, a polyethylene glycol, a polypropylene, a propylene glycol, a mixture of ethylene and propylene glycols, or a combination thereof.

2. The composition according to claim 1, wherein the linker moiety comprises an alkene, a polyether, a polyalcohol, a polyester, a polyamine, a polyalkylamine, a polyphosphodiester, or a combination thereof.

3. An oligonucleotide attached to a solid synthesis support, wherein the solid synthesis support comprises a composition of claim 1.

4. An oligonucleotide attached to a solid synthesis support, wherein the solid synthesis support comprises a composition of claim 1, and the oligonucleotide comprises one or more compositions comprising:

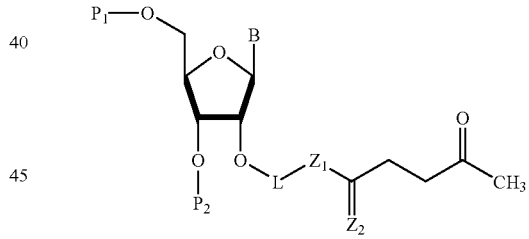

wherein B comprises a nitrogenous base that is modified or unmodified; L comprises a linker moiety; $Z_1$ is an oxygen or a sulfur; $Z_2$ is an oxygen or a sulfur; $P_1$ comprises a blocking group; and $P_2$ comprises a phosphorous moiety.

5. An oligonucleotide attached to a solid synthesis support, wherein the solid synthesis support comprises a composition of claim 1, and the oligonucleotide comprises one or more compositions comprising:

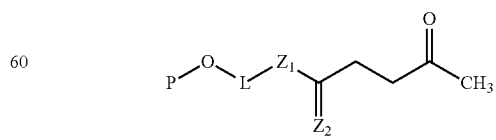

wherein L comprises a non-nucleosidic linker moiety; $Z_1$ is an oxygen or a sulfur; $Z_2$ is an oxygen or a sulfur; and P comprises a phosphorous moiety.

6. An oligonucleotide attached to a solid synthesis support, wherein the solid synthesis support comprises a composition of claim 1, and the oligonucleotide comprises one or more compositions comprising:

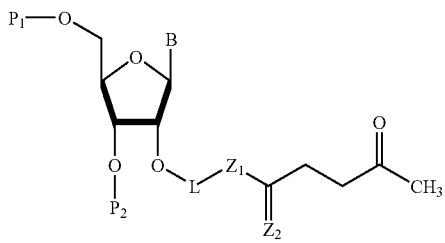

wherein B comprises a nitrogenous base that is modified or unmodified; L comprises a linker moiety; $Z_1$ is an oxygen or a sulfur; $Z_2$ is an oxygen or a sulfur; $P_1$ comprises a blocking group; and $P_2$ comprises a phosphorous moiety, and a composition comprising:

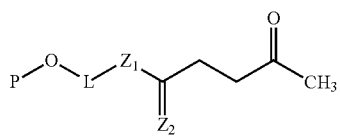

wherein L comprises a non-nucleosidic linker moiety; $Z_1$ is an oxygen or a sulfur; $Z_2$ is an oxygen or a sulfur; and P comprises a phosphorous moiety.

7. A method of synthesizing an oligonucleotide comprising adding one more nucleotides to the composition of claim 1.

8. The composition of claim 1 wherein the linker is attached to the solid support through a succinate, glutarate or oxalate linkage.

9. The composition of claim 1, wherein the solid support comprises controlled pore glass, polystyrene or polymethacrylate.

10. The composition of claim 1, wherein S and L are attached through a covalent amide bond.

11. The composition of claim 1, wherein the covalent linkage is through a converted hydroxyl group.

12. The composition of claim 1, wherein $Z_1$ is sulfur.

13. The composition of claim 1, wherein $Z_2$ is sulfur.

14. The composition of claim 12, wherein $Z_2$ is sulfur.

* * * * *